US009259233B2

(12) United States Patent
Gruber et al.

(10) Patent No.: US 9,259,233 B2
(45) Date of Patent: Feb. 16, 2016

(54) METHOD AND DEVICE FOR DISTENDING A GYNECOLOGICAL CAVITY

(75) Inventors: William H. Gruber, Southborough, MA (US); Ronald D. Adams, Holliston, MA (US); Michael A. Lorenz, Gahanna, OH (US); Ryan S. Crisp, Lewis Center, OH (US); Chris W. Clcenas, Pataskala, OH (US); Brent L. Burchfield, Powell, OH (US); Paul DiCesare, Easton, CT (US); Jeffrey Radziunas, Wallingford, CT (US); Daniel Vigliotti, Hamden, CT (US)

(73) Assignee: Hologic, Inc., Marlborough, MA (US)

( * ) Notice: Subject to any disclaimer, the term of this patent is extended or adjusted under 35 U.S.C. 154(b) by 417 days.

(21) Appl. No.: 11/951,853

(22) Filed: Dec. 6, 2007

(65) Prior Publication Data

US 2008/0249534 A1 Oct. 9, 2008

Related U.S. Application Data

(60) Provisional application No. 60/910,625, filed on Apr. 6, 2007, provisional application No. 60/910,618, filed on Apr. 6, 2007.

(51) Int. Cl.
*A61B 17/42* (2006.01)
*A61B 17/30* (2006.01)
(Continued)

(52) U.S. Cl.
CPC .............. *A61B 17/30* (2013.01); *A61B 1/0615* (2013.01); *A61B 1/0661* (2013.01); *A61B 1/303* (2013.01);
(Continued)

(58) Field of Classification Search
CPC .............. A61B 2017/4216; A61B 2017/4225; A61B 5/6875; A61B 17/30; A61B 1/303; A61B 17/0217; A61B 17/12045; A61B 17/12099; A61B 17/12136; A61B 17/32002; A61B 17/42; A61F 6/225
USPC ................... 606/191–193, 198; 600/201–204
See application file for complete search history.

(56) References Cited

U.S. PATENT DOCUMENTS 2,849,002 A 8/1958 Oddo et al.
3,561,429 A 2/1971 Jewett
(Continued)

FOREIGN PATENT DOCUMENTS

EP 0010650 5/1980
EP 0044877 2/1982
(Continued)

OTHER PUBLICATIONS

International Search Report and Written Opinion Received in PCT/US07/83982 Dated May 20, 2008.
(Continued)

*Primary Examiner* — Katherine M Shi
*Assistant Examiner* — Michael Mendoza
(74) *Attorney, Agent, or Firm* — Vista IP Law Group LLP

(57) ABSTRACT

Method and device for distending a gynecological cavity. According to one embodiment, a mechanical, non-fluid device is used to distend the gynecological cavity. Such devices include, for example, self-expanding members, such as resilient baskets, coils, whisks, prongs, and loops, or mechanically expanded members, such as inflatable balloons, mechanically-expanded cages and loops, and scissor jacks. The device may serve a purpose in addition to distension, such as illumination, imaging, irrigation, drug delivery, resection and cauterization.

19 Claims, 72 Drawing Sheets

(51) Int. Cl.

| | | |
|---|---|---|
| A61B 1/303 | (2006.01) | |
| A61B 17/02 | (2006.01) | |
| A61B 17/32 | (2006.01) | |
| A61F 6/20 | (2006.01) | |
| A61M 25/10 | (2013.01) | |
| A61M 37/00 | (2006.01) | |
| A61B 1/06 | (2006.01) | |
| A61B 5/00 | (2006.01) | |
| A61F 6/22 | (2006.01) | |
| A61M 25/09 | (2006.01) | |
| A61M 29/02 | (2006.01) | |
| A61M 31/00 | (2006.01) | |
| A61N 5/06 | (2006.01) | |
| A61N 7/02 | (2006.01) | |
| A61B 17/12 | (2006.01) | |
| A61B 17/3207 | (2006.01) | |
| A61B 17/00 | (2006.01) | |
| A61B 17/22 | (2006.01) | |
| A61B 19/00 | (2006.01) | |
| A61M 25/00 | (2006.01) | |

(52) U.S. Cl.
CPC ........... *A61B 5/6875* (2013.01); *A61B 17/0218* (2013.01); *A61B 17/12045* (2013.01); *A61B 17/12099* (2013.01); *A61B 17/12136* (2013.01); *A61B 17/22* (2013.01); *A61B 17/32002* (2013.01); *A61B 17/42* (2013.01); *A61B 17/4241* (2013.01); *A61F 6/20* (2013.01); *A61F 6/225* (2013.01); *A61M 25/09* (2013.01); *A61M 25/1002* (2013.01); *A61M 25/1011* (2013.01); *A61M 29/02* (2013.01); *A61M 31/002* (2013.01); *A61M 37/0092* (2013.01); *A61N 5/062* (2013.01); *A61N 5/0603* (2013.01); *A61N 7/022* (2013.01); *A61B 17/12013* (2013.01); *A61B 17/320068* (2013.01); *A61B 17/320783* (2013.01); *A61B 2017/00084* (2013.01); *A61B 2017/00278* (2013.01); *A61B 2017/00557* (2013.01); *A61B 2017/00862* (2013.01); *A61B 2017/00876* (2013.01); *A61B 2017/00893* (2013.01); *A61B 2017/12018* (2013.01); *A61B 2017/12127* (2013.01); *A61B 2017/22038* (2013.01); *A61B 2017/306* (2013.01); *A61B 2019/464* (2013.01); *A61B 2019/5206* (2013.01); *A61M 25/0026* (2013.01); *A61M 2025/105* (2013.01); *A61M 2025/1047* (2013.01)

(56) References Cited

U.S. PATENT DOCUMENTS

| | | | |
|---|---|---|---|
| 4,188,952 | A | 2/1980 | Loschilov et al. |
| 4,198,981 | A | 4/1980 | Sinnreich |
| 4,203,444 | A | 5/1980 | Bonnell et al. |
| 4,246,902 | A | 1/1981 | Martinez |
| 4,261,360 | A | 4/1981 | Perez |
| 4,598,698 | A | 7/1986 | Siegmund |
| 4,598,710 | A | 7/1986 | Kleinberg et al. |
| 4,650,462 | A | 3/1987 | DeSatnick et al. |
| 4,673,393 | A | 6/1987 | Suzuki et al. |
| 4,700,694 | A | 10/1987 | Shishido |
| 4,729,763 | A | 3/1988 | Henrie |
| 4,848,323 | A | 7/1989 | Marijnissen et al. |
| 4,895,565 | A | 1/1990 | Hillstead |
| 4,949,718 | A | 8/1990 | Neuwirth et al. |
| 4,998,527 | A | 3/1991 | Meyer |
| 5,078,725 | A | 1/1992 | Enderle et al. |
| 5,104,377 | A | 4/1992 | Levine |
| 5,108,414 | A | 4/1992 | Enderle et al. |
| 5,125,903 | A | 6/1992 | McLaughlin et al. |
| 5,163,433 | A | 11/1992 | Kagawa et al. |
| 5,163,949 | A | 11/1992 | Bonutti |
| 5,183,031 | A | 2/1993 | Rossoff |
| 5,195,541 | A | 3/1993 | Obenchain |
| 5,201,756 | A | 4/1993 | Horzewski et al. |
| 5,222,971 | A | 6/1993 | Willard et al. |
| 5,246,016 | A | 9/1993 | Lieber et al. |
| 5,259,836 | A * | 11/1993 | Thurmond et al. ........... 600/431 |
| 5,269,798 | A | 12/1993 | Winkler |
| 5,275,609 | A | 1/1994 | Pingleton et al. |
| 5,304,115 | A | 4/1994 | Pflueger et al. |
| 5,320,091 | A | 6/1994 | Grossi et al. |
| 5,334,183 | A | 8/1994 | Wuchinich |
| 5,361,752 | A | 11/1994 | Moll et al. |
| 5,377,668 | A | 1/1995 | Ehmsen et al. |
| 5,392,765 | A | 2/1995 | Muller |
| 5,402,772 | A | 4/1995 | Moll et al. |
| 5,423,844 | A | 6/1995 | Miller |
| 5,443,470 | A | 8/1995 | Stern et al. |
| 5,450,843 | A | 9/1995 | Moll et al. |
| 5,458,112 | A | 10/1995 | Weaver |
| 5,484,401 | A | 1/1996 | Rodriguez et al. |
| 5,503,626 | A | 4/1996 | Goldrath |
| 5,505,730 | A | 4/1996 | Edwards |
| 5,514,091 | A | 5/1996 | Yoon |
| 5,522,790 | A | 6/1996 | Moll et al. |
| 5,540,658 | A | 7/1996 | Evans et al. |
| 5,575,788 | A | 11/1996 | Baker et al. |
| 5,601,583 | A | 2/1997 | Donahue et al. |
| 5,602,449 | A | 2/1997 | Krause et al. |
| 5,618,296 | A | 4/1997 | Sorensen et al. |
| 5,624,395 | A | 4/1997 | Mikhail et al. |
| 5,624,399 | A | 4/1997 | Ackerman |
| 5,656,013 | A | 8/1997 | Yoon |
| 5,695,511 | A | 12/1997 | Cano et al. |
| 5,697,940 | A | 12/1997 | Chu et al. |
| 5,709,664 | A | 1/1998 | Vandenbroek et al. |
| 5,725,525 | A | 3/1998 | Kordis |
| 5,730,725 | A | 3/1998 | Yoon |
| 5,738,629 | A | 4/1998 | Moll et al. |
| 5,741,287 | A | 4/1998 | Alden et al. |
| 5,743,850 | A | 4/1998 | Moll et al. |
| 5,743,851 | A | 4/1998 | Moll et al. |
| 5,749,845 | A | 5/1998 | Hildebrand et al. |
| 5,749,889 | A | 5/1998 | Bacich et al. |
| 5,755,731 | A | 5/1998 | Grinberg |
| 5,782,800 | A | 7/1998 | Yoon |
| 5,800,493 | A | 9/1998 | Stevens et al. |
| 5,807,401 | A | 9/1998 | Grieshaber et al. |
| 5,823,945 | A | 10/1998 | Moll et al. |
| 5,843,046 | A | 12/1998 | Motisi et al. |
| 5,855,549 | A | 1/1999 | Newman |
| 5,857,585 | A | 1/1999 | Tolkoff et al. |
| 5,865,728 | A | 2/1999 | Moll et al. |
| 5,873,815 | A | 2/1999 | Kerin et al. |
| 5,891,134 | A | 4/1999 | Goble et al. |
| 5,899,915 | A | 5/1999 | Saadat |
| 5,902,251 | A | 5/1999 | vanHooydonk |
| 5,904,649 | A | 5/1999 | Andrese |
| 5,904,680 | A | 5/1999 | Kordis et al. |
| 5,911,739 | A | 6/1999 | Kordis et al. |
| 5,916,198 | A | 6/1999 | Dillow |
| 5,954,714 | A | 9/1999 | Saadat et al. |
| 5,954,715 | A | 9/1999 | Harrington et al. |
| 5,961,444 | A | 10/1999 | Thompson |
| 5,961,532 | A | 10/1999 | Finley et al. |
| 5,964,755 | A | 10/1999 | Edwards |
| 5,964,777 | A | 10/1999 | Drucker |
| 5,972,000 | A | 10/1999 | Beyar et al. |
| 6,002,968 | A * | 12/1999 | Edwards ....................... 607/101 |
| 6,032,673 | A | 3/2000 | Savage et al. |
| 6,039,748 | A | 3/2000 | Savage et al. |
| 6,042,590 | A | 3/2000 | Sporri et al. |
| 6,068,626 | A | 5/2000 | Harrington et al. |
| 6,080,129 | A | 6/2000 | Blaisdell |
| 6,086,544 | A | 7/2000 | Hibner et al. |
| 6,117,070 | A | 9/2000 | Akiba |
| 6,126,635 | A | 10/2000 | Simpson et al. |

(56) References Cited

U.S. PATENT DOCUMENTS

| | | | |
|---|---|---|---|
| 6,139,570 A | 10/2000 | Saadat et al. | |
| 6,149,632 A | 11/2000 | Landuyt | |
| 6,159,209 A | 12/2000 | Hakky | |
| 6,190,357 B1 | 2/2001 | Ferrari et al. | |
| 6,216,043 B1 | 4/2001 | Swanson et al. | |
| 6,216,044 B1 | 4/2001 | Kordis | |
| 6,221,007 B1 | 4/2001 | Green | |
| 6,293,952 B1 | 9/2001 | Brosens et al. | |
| 6,319,272 B1 | 11/2001 | Brenneman et al. | |
| 6,328,686 B1 | 12/2001 | Kovac | |
| 6,378,524 B1 | 4/2002 | Jones | |
| 6,387,110 B1 | 5/2002 | Drucker et al. | |
| 6,395,012 B1 | 5/2002 | Yoon et al. | |
| 6,428,498 B2 | 8/2002 | Uflacker | |
| 6,428,539 B1 | 8/2002 | Baxter et al. | |
| 6,432,116 B1 | 8/2002 | Callister et al. | |
| 6,440,061 B1 | 8/2002 | Wenner et al. | |
| 6,458,076 B1 | 10/2002 | Pruitt | |
| 6,471,644 B1 | 10/2002 | Sidor, Jr. | |
| 6,494,909 B2 | 12/2002 | Greenhalgh | |
| 6,537,207 B1 | 3/2003 | Rice et al. | |
| 6,547,784 B1 | 4/2003 | Thompson et al. | |
| 6,565,557 B1 | 5/2003 | Sporri et al. | |
| 6,605,037 B1 | 8/2003 | Moll et al. | |
| 6,607,545 B2 | 8/2003 | Kammerer et al. | |
| 6,612,977 B2 | 9/2003 | Staskin et al. | |
| 6,626,940 B2 | 9/2003 | Crowley | |
| 6,638,235 B2 | 10/2003 | Miller et al. | |
| 6,673,101 B1 | 1/2004 | Fitzgerald et al. | |
| 6,682,477 B2 | 1/2004 | Boebel et al. | |
| 6,709,667 B1 | 3/2004 | Lowe et al. | |
| 6,742,236 B1 | 6/2004 | Dion et al. | |
| 6,763,833 B1 | 7/2004 | Khera et al. | |
| 6,802,825 B2 | 10/2004 | Ackerman et al. | |
| 6,805,131 B2 | 10/2004 | Kordis | |
| 6,812,204 B1 | 11/2004 | McHale et al. | |
| 6,821,274 B2 | 11/2004 | McHale et al. | |
| 6,827,703 B1 | 12/2004 | Ackerman | |
| 6,858,024 B1 | 2/2005 | Berg et al. | |
| 6,896,682 B1 | 5/2005 | Mcclellan et al. | |
| 6,951,569 B2 | 10/2005 | Nohilly et al. | |
| 6,960,203 B2 | 11/2005 | Xiao et al. | |
| 6,979,332 B2 | 12/2005 | Adams | |
| 6,997,925 B2 | 2/2006 | Maguire et al. | |
| 7,037,321 B2 | 5/2006 | Sachdeva et al. | |
| 7,070,559 B2 | 7/2006 | Adams et al. | |
| 7,105,003 B2 | 9/2006 | Hiltebrandt | |
| 7,150,713 B2 | 12/2006 | Shener et al. | |
| 7,189,206 B2 | 3/2007 | Quick et al. | |
| 7,226,459 B2 | 6/2007 | Cesarini et al. | |
| 7,226,460 B2 | 6/2007 | Gibson et al. | |
| 7,249,602 B1 | 7/2007 | Emanuel | |
| 7,458,940 B2 | 12/2008 | Miller | |
| 7,462,187 B2 | 12/2008 | Johnston et al. | |
| 7,468,060 B2 | 12/2008 | Utley et al. | |
| 7,481,817 B2 | 1/2009 | Sauer | |
| 7,491,212 B2 | 2/2009 | Sikora et al. | |
| 7,497,833 B2 | 3/2009 | Miller | |
| 7,510,563 B2 | 3/2009 | Cesarini et al. | |
| 7,588,545 B2 | 9/2009 | Cohen et al. | |
| 7,611,474 B2 | 11/2009 | Hibner et al. | |
| 7,666,200 B2 | 2/2010 | Heisler | |
| 7,749,254 B2 | 7/2010 | Sobelman et al. | |
| 7,753,857 B2 | 7/2010 | Hibner | |
| 7,763,033 B2 | 7/2010 | Gruber et al. | |
| 7,785,250 B2 | 8/2010 | Nakao | |
| 7,806,835 B2 | 10/2010 | Hibner et al. | |
| 7,938,804 B2 | 5/2011 | Fischvogt | |
| 2001/0029371 A1 | 10/2001 | Kordis | |
| 2001/0041900 A1 | 11/2001 | Callister et al. | |
| 2001/0047183 A1 | 11/2001 | Privitera et al. | |
| 2001/0056222 A1 | 12/2001 | Rudischhauser et al. | |
| 2002/0010457 A1 | 1/2002 | Duchon et al. | |
| 2002/0013601 A1* | 1/2002 | Nobles et al. | 606/193 |
| 2002/0020417 A1 | 2/2002 | Nikolchev | |
| 2002/0068934 A1 | 6/2002 | Edwards et al. | |
| 2002/0082634 A1 | 6/2002 | Kammerer et al. | |
| 2003/0050639 A1 | 3/2003 | Yachia et al. | |
| 2003/0083684 A1 | 5/2003 | Cesarini et al. | |
| 2003/0114875 A1 | 6/2003 | Sjostrom | |
| 2003/0153940 A1 | 8/2003 | Nohilly et al. | |
| 2004/0002702 A1 | 1/2004 | Xiao et al. | |
| 2004/0002703 A1 | 1/2004 | Xiao et al. | |
| 2004/0049211 A1 | 3/2004 | Tremulis et al. | |
| 2004/0116955 A1* | 6/2004 | Foltz et al. | 606/193 |
| 2004/0127932 A1 | 7/2004 | Shah | |
| 2004/0152977 A1* | 8/2004 | Duchon et al. | 600/431 |
| 2004/0204682 A1 | 10/2004 | Smith | |
| 2004/0225187 A1 | 11/2004 | Kamrava et al. | |
| 2004/0255957 A1 | 12/2004 | Cafferata | |
| 2004/0267157 A1 | 12/2004 | Miller | |
| 2005/0027245 A1 | 2/2005 | Sachdeva et al. | |
| 2005/0045183 A1 | 3/2005 | Callister et al. | |
| 2005/0080318 A1 | 4/2005 | Squicciarini | |
| 2005/0090849 A1 | 4/2005 | Adams | |
| 2005/0107663 A1 | 5/2005 | Saadat et al. | |
| 2005/0113715 A1 | 5/2005 | Schwindt et al. | |
| 2005/0113836 A1 | 5/2005 | Lozier et al. | |
| 2005/0113857 A1 | 5/2005 | Nohilly et al. | |
| 2005/0171569 A1* | 8/2005 | Girard et al. | 606/193 |
| 2005/0177168 A1 | 8/2005 | Brunnett et al. | |
| 2005/0182397 A1 | 8/2005 | Ryan | |
| 2005/0222598 A1 | 10/2005 | Ho et al. | |
| 2005/0234437 A1 | 10/2005 | Baxter et al. | |
| 2005/0240206 A1 | 10/2005 | Sjostrom | |
| 2005/0245960 A1 | 11/2005 | Grundeman | |
| 2005/0250933 A1 | 11/2005 | Saadat et al. | |
| 2005/0250993 A1 | 11/2005 | Jaeger | |
| 2005/0267408 A1 | 12/2005 | Grandt et al. | |
| 2005/0277970 A1 | 12/2005 | Norman et al. | |
| 2005/0277975 A1 | 12/2005 | Saadat et al. | |
| 2005/0288551 A1 | 12/2005 | Callister et al. | |
| 2006/0004436 A1 | 1/2006 | Amarant et al. | |
| 2006/0009798 A1 | 1/2006 | Callister et al. | |
| 2006/0036138 A1 | 2/2006 | Heller et al. | |
| 2006/0047185 A1 | 3/2006 | Sherner et al. | |
| 2006/0064074 A1 | 3/2006 | Mallaby | |
| 2006/0089658 A1* | 4/2006 | Harrington | 606/119 |
| 2006/0189972 A1 | 8/2006 | Grossman | |
| 2006/0200042 A1 | 9/2006 | Weikel, Jr. et al. | |
| 2006/0206136 A1 | 9/2006 | Sachdeva et al. | |
| 2006/0212055 A1 | 9/2006 | Karabey et al. | |
| 2006/0229647 A1 | 10/2006 | Spitz et al. | |
| 2006/0241344 A1 | 10/2006 | Wilk | |
| 2006/0241586 A1 | 10/2006 | Wilk | |
| 2006/0241630 A1 | 10/2006 | Brunnett et al. | |
| 2006/0293560 A1 | 12/2006 | Nguyen et al. | |
| 2007/0010845 A1* | 1/2007 | Gong et al. | 606/192 |
| 2007/0161957 A1 | 7/2007 | Guenther et al. | |
| 2007/0225744 A1 | 9/2007 | Nobles et al. | |
| 2007/0227544 A1 | 10/2007 | Swann et al. | |
| 2007/0232859 A1 | 10/2007 | Secrest et al. | |
| 2008/0015621 A1 | 1/2008 | Emanuel | |
| 2008/0051758 A1 | 2/2008 | Rioux et al. | |
| 2008/0058588 A1 | 3/2008 | Emanuel | |
| 2008/0058595 A1 | 3/2008 | Snoke et al. | |
| 2008/0065125 A1 | 3/2008 | Olson | |
| 2008/0147012 A1 | 6/2008 | Rome | |
| 2008/0183192 A1 | 7/2008 | Saal et al. | |
| 2008/0234715 A1 | 9/2008 | Pesce et al. | |
| 2008/0245371 A1 | 10/2008 | Gruber et al. | |
| 2008/0249366 A1 | 10/2008 | Gruber et al. | |
| 2008/0249553 A1 | 10/2008 | Gruber et al. | |
| 2008/0262302 A1 | 10/2008 | Azarbarzin et al. | |
| 2008/0281224 A1 | 11/2008 | Johnson | |
| 2008/0319342 A1 | 12/2008 | Shabaz | |
| 2009/0005705 A1 | 1/2009 | Hart et al. | |
| 2009/0048485 A1 | 2/2009 | Heisler | |
| 2009/0054728 A1 | 2/2009 | Trusty | |
| 2009/0118699 A1 | 5/2009 | Utley et al. | |
| 2009/0137927 A1 | 5/2009 | Miller | |
| 2009/0177217 A1 | 7/2009 | Keller | |
| 2009/0198149 A1 | 8/2009 | Privitera et al. | |
| 2009/0270895 A1 | 10/2009 | Churchill et al. | |

(56) References Cited

U.S. PATENT DOCUMENTS

| | | |
|---|---|---|
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0063360 A1 | 3/2010 | Harrington et al. |
| 2010/0152533 A1 | 6/2010 | Mark |
| 2010/0152758 A1 | 6/2010 | Mark et al. |
| 2010/0152761 A1 | 6/2010 | Mark |
| 2010/0160818 A1 | 6/2010 | Haberstich et al. |
| 2010/0179480 A1 | 7/2010 | Sugiki et al. |
| 2010/0185153 A1 | 7/2010 | Sugiki et al. |
| 2010/0198242 A1 | 8/2010 | Heisler |
| 2010/0274194 A1 | 10/2010 | Sobelman et al. |
| 2010/0312053 A1 | 12/2010 | Larsen |
| 2011/0034943 A1 | 2/2011 | Churchill et al. |
| 2011/0077674 A1 | 3/2011 | Sullivan et al. |

FOREIGN PATENT DOCUMENTS

| | | |
|---|---|---|
| EP | 0141589 | 5/1985 |
| EP | 0366292 | 5/1990 |
| EP | 0449663 | 10/1991 |
| EP | 0531710 | 3/1993 |
| EP | 0539125 | 4/1993 |
| EP | 0782427 | 2/1996 |
| EP | 0853468 | 5/1996 |
| EP | 0812573 | 12/1997 |
| EP | 1259180 | 11/2002 |
| EP | 1635695 | 1/2005 |
| FR | 2701401 | 8/1994 |
| WO | WO 94/07445 | 4/1994 |
| WO | WO 94/11052 | 5/1994 |
| WO | WO 95/10326 | 4/1995 |
| WO | WO9532011 | 11/1995 |
| WO | WO 96/15741 | 5/1996 |
| WO | WO9818520 | 5/1998 |
| WO | WO 98/29068 | 7/1998 |
| WO | WO 98/51244 | 11/1998 |
| WO | WO 99/60960 | 12/1999 |
| WO | WO 00/00100 | 1/2000 |
| WO | WO0012832 | 3/2000 |
| WO | WO 00/66031 | 11/2000 |
| WO | WO 01/08575 | 2/2001 |
| WO | WO 03/037194 | 5/2003 |
| WO | WO 2005/009504 | 2/2005 |
| WO | WO 2005/048862 | 6/2005 |
| WO | WO 2005/074844 | 8/2005 |
| WO | WO 2005/104966 | 11/2005 |
| WO | WO 2009/111717 | 9/2009 |
| WO | WO 2010/127171 | 11/2010 |
| WO | WO 2010/127174 | 11/2010 |

OTHER PUBLICATIONS

International Search Report and Written Opinion Received in PCT/US08/59493 Dated Apr. 4, 2008.
International Search Report and Written Opinion Received in PCT/US07/83833 Dated Jun. 5, 2008.
International Search Report and Written Opinion Received in PCT/US08/59504 Dated Sep. 4, 2008.
International Search Report and Written Opinion Received in PCT/US08/59503 Dated Sep. 5, 2008.
U.S. Appl. No. 11/852,151, Gruber, et al.
U.S. Appl. No. 11/936,003, Gruber, et al.
U.S. Appl. No. 11/852,116, Gruber, et al.
U.S. Appl. No. 11/852,142, Gruber, et al.
U.S. Appl. No. 11/852,121, Adams, et al.
U.S. Appl. No. 11/852,200, Adams, et al.
U.S. Appl. No. 11/923,357, Gruber, et al.
U.S. Appl. No. 11/923,482, Gruber, et al.
International Search Report and Written Opinion Received in PCT/US07/79449 Dated Jan. 28, 2008.
U.S. Appl. No. 12/432,691, Adams, et al.
U.S. Appl. No. 12/432,702, Chin, et al.
U.S. Appl. No. 12/432,686, Sullivan, et al.
U.S. Appl. No. 12/432,675, Churchill, et al.
U.S. Appl. No. 12/432,647, Litscher, et al.
U.S. Appl. No. 12/842,775, Gruber, et al.
U.S. Appl. No. 12/565,620, Adams, et al.
U.S. Appl. No. 12/972,233, Sullivan, et al.
U.S. Appl. No. 12/917351, Churchill, et al.
U.S. Appl. No. 12/956,974, Adams, et al.
International Search Report and Written Opinion dated Jul. 6, 2010, PCT Application No. PCT/US2010/033047 in 13 pages.
International Search Report and Written Opinion dated Jun. 29, 2010, PCT Application No. PCT/US2010/033050 in 7 pages.
International Search Report and Written Opinion dated Jan. 11, 2011, in PCT Application No. PCT/US10/56416 in 14 pages.
Mark H. Emanuel, The Intra Uterine Morcellator: A New Hysteroscopic Operating Technique to Remove Intrauterine Polyps and Myomas, Journal of Minimally Invasive Gynecology, vol. 12, p. 62-66 (2005).
"When mechanical dilation is necessary, a few prerequisites can make a difference", OBG Management, Apr. 2009, vol. 21, No. 4, p. 29-33.

* cited by examiner

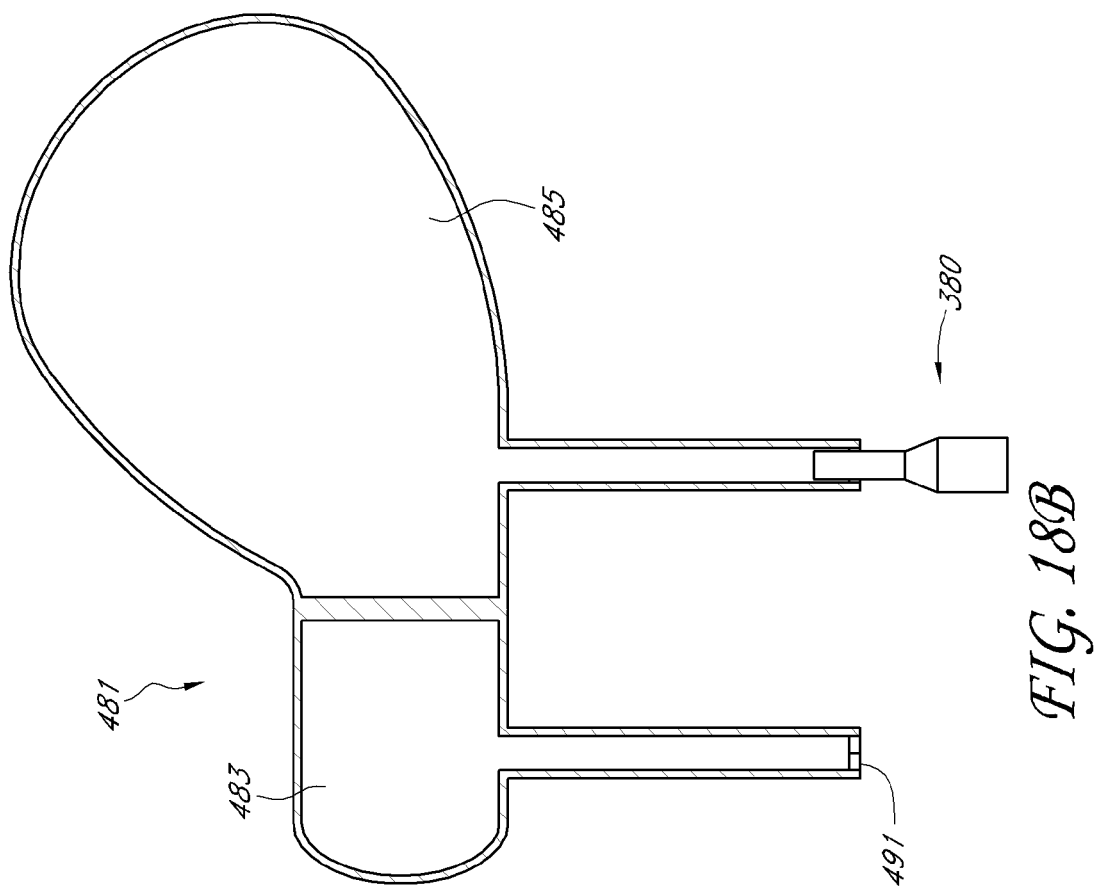
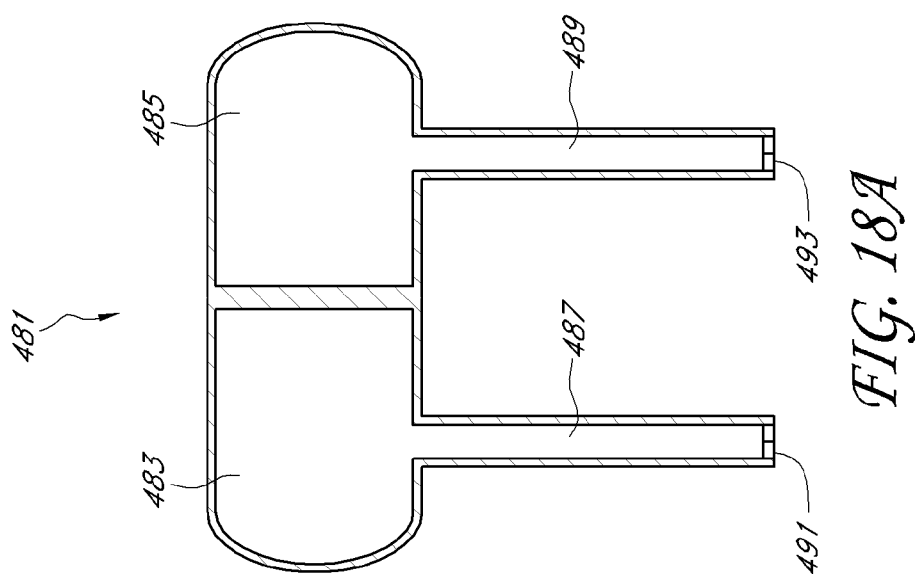
FIG. 18B
FIG. 18A

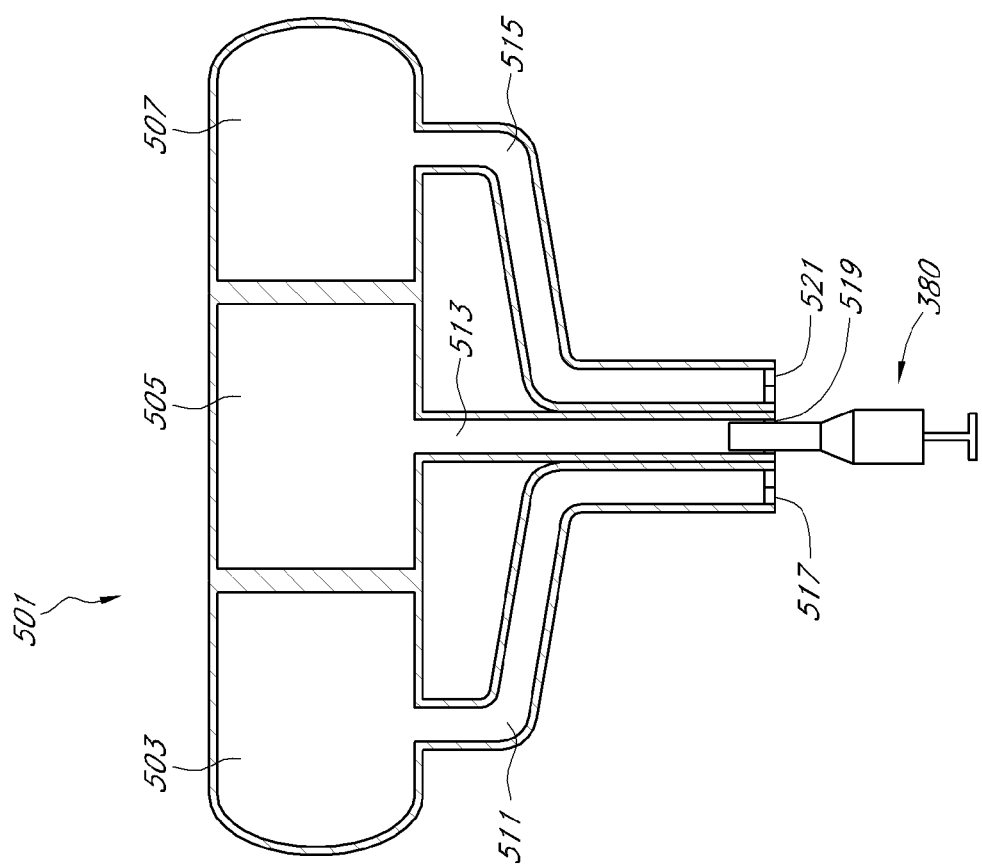

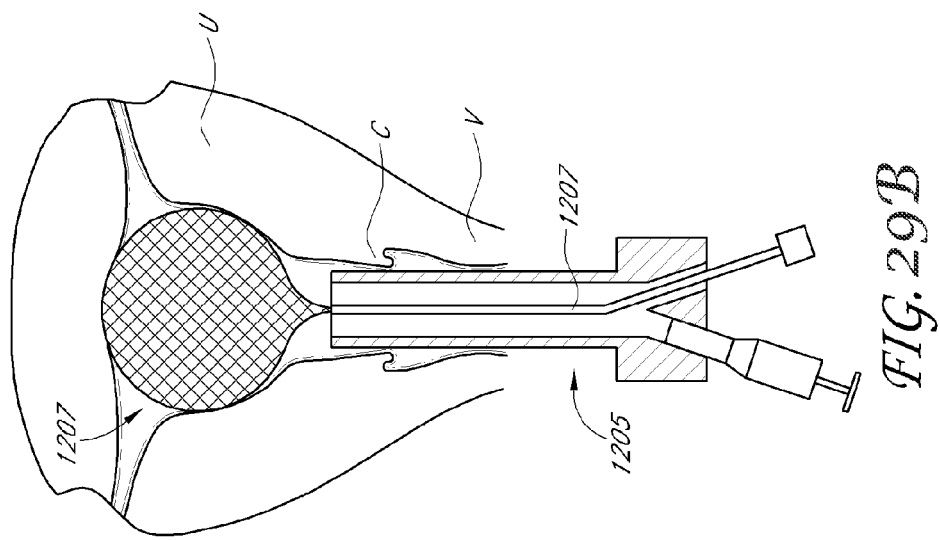
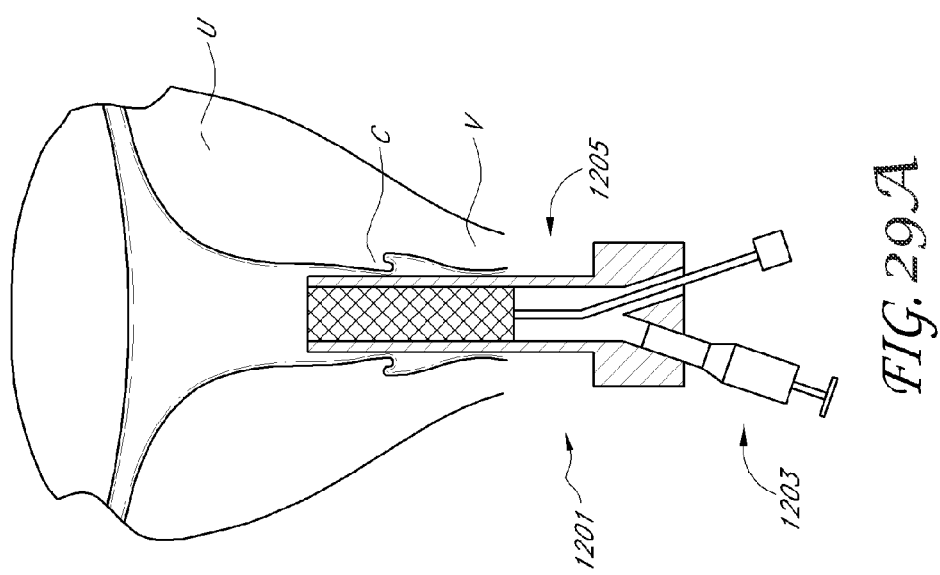

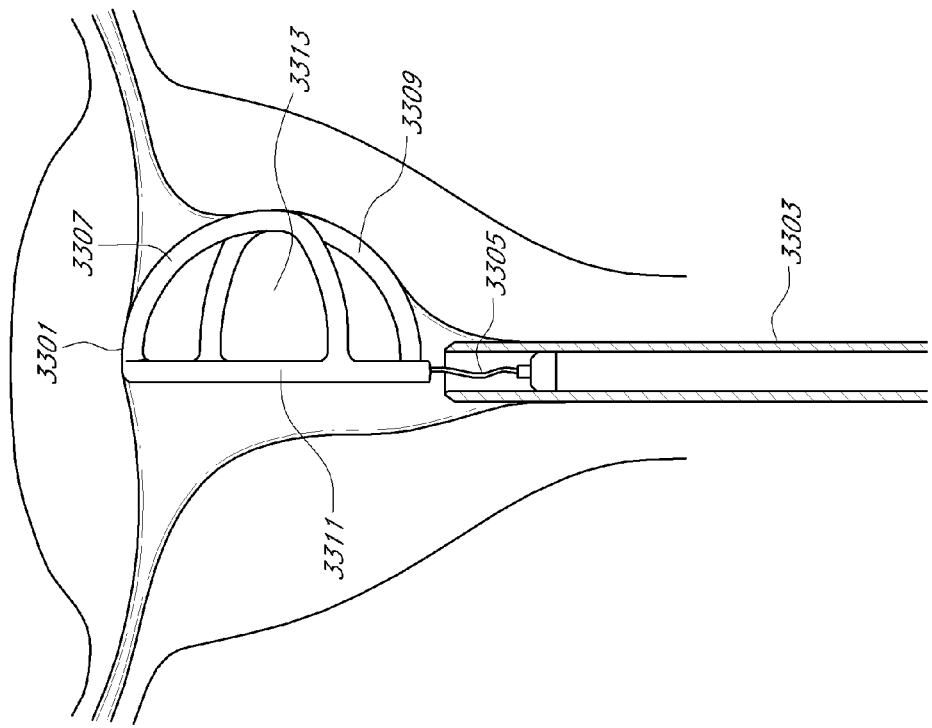
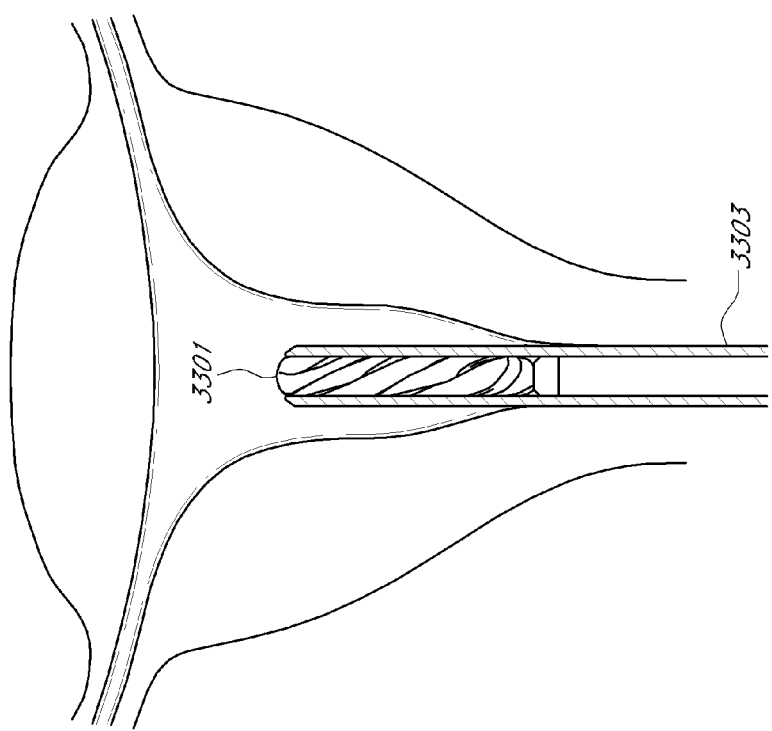

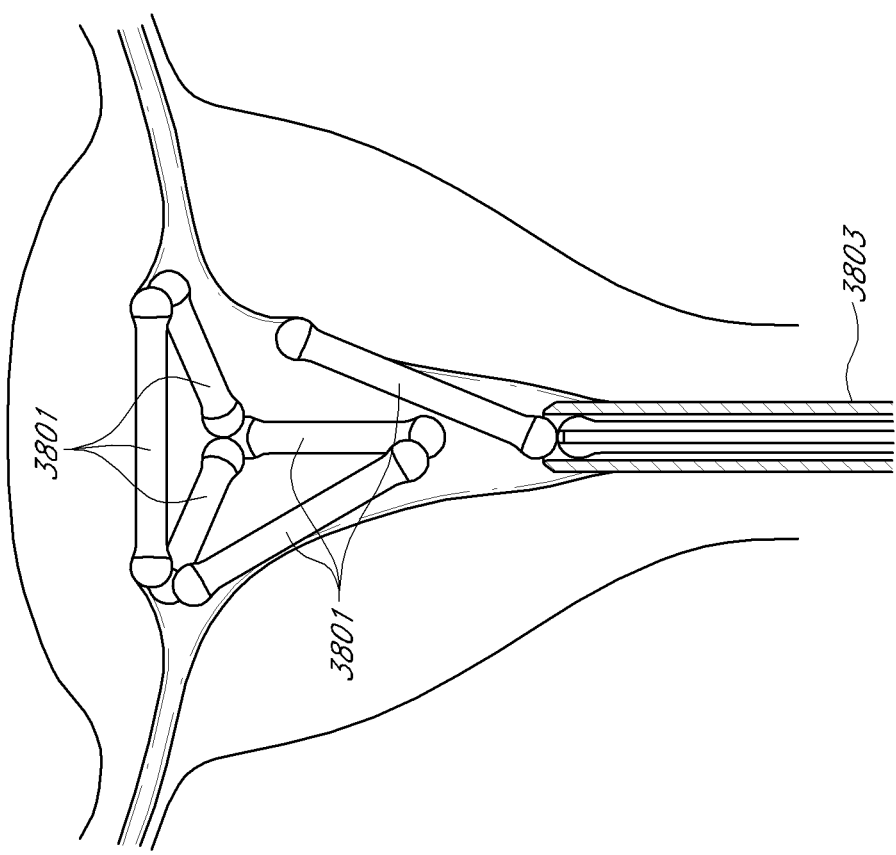

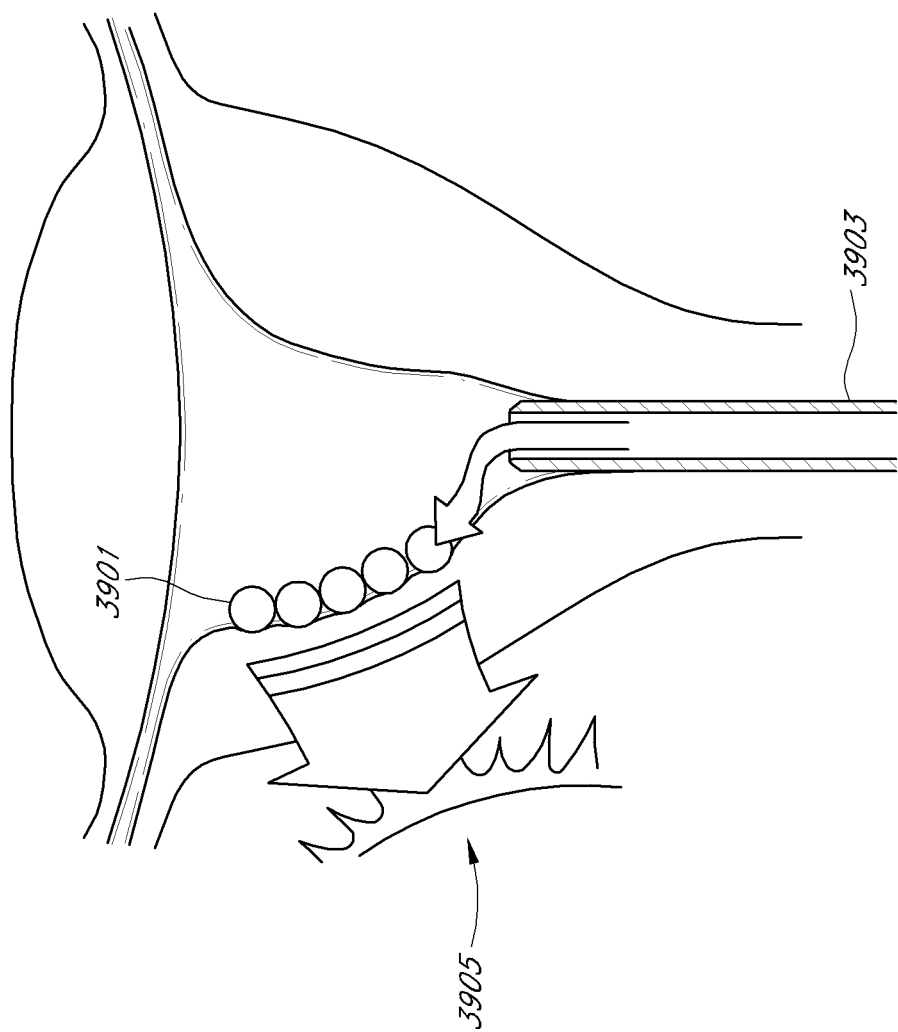

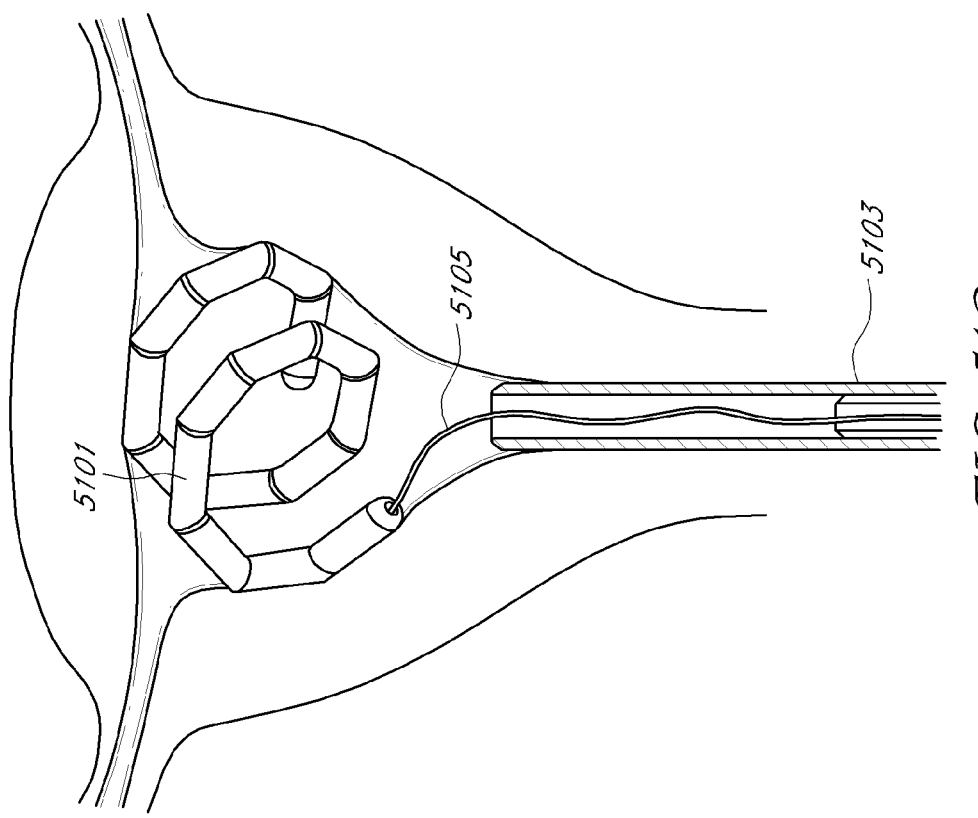
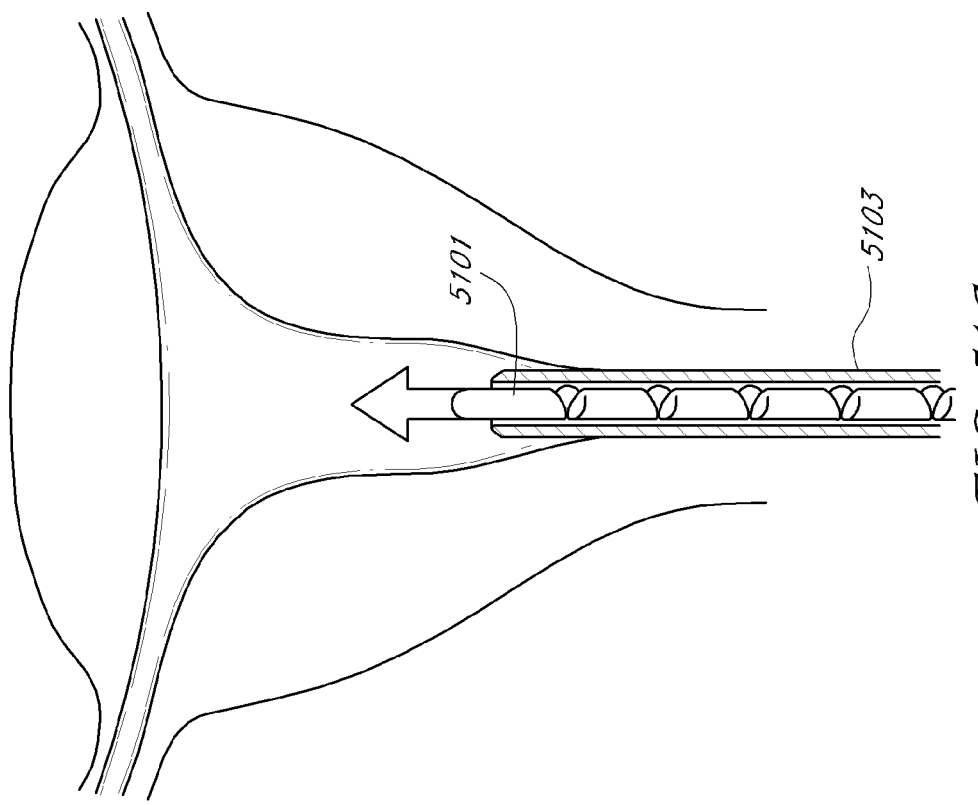

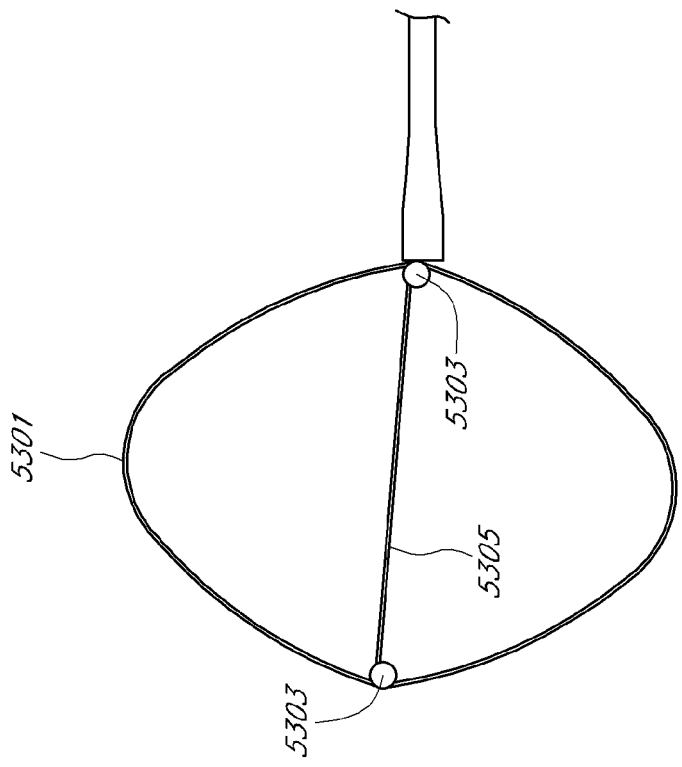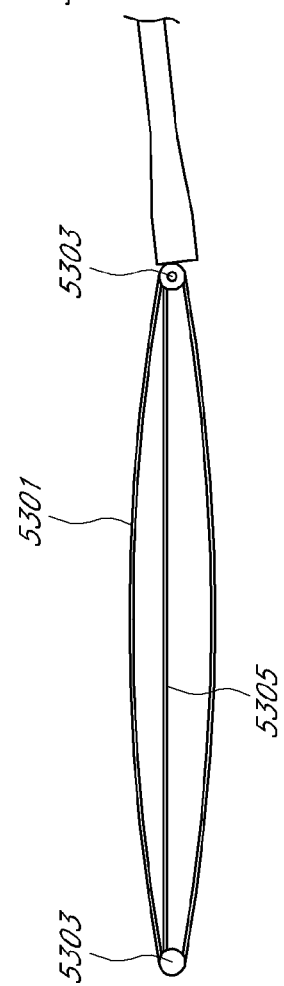
FIG. 53B
FIG. 53A

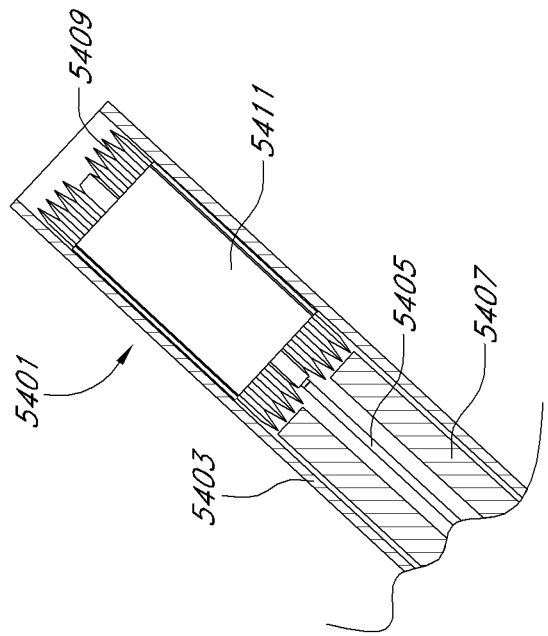
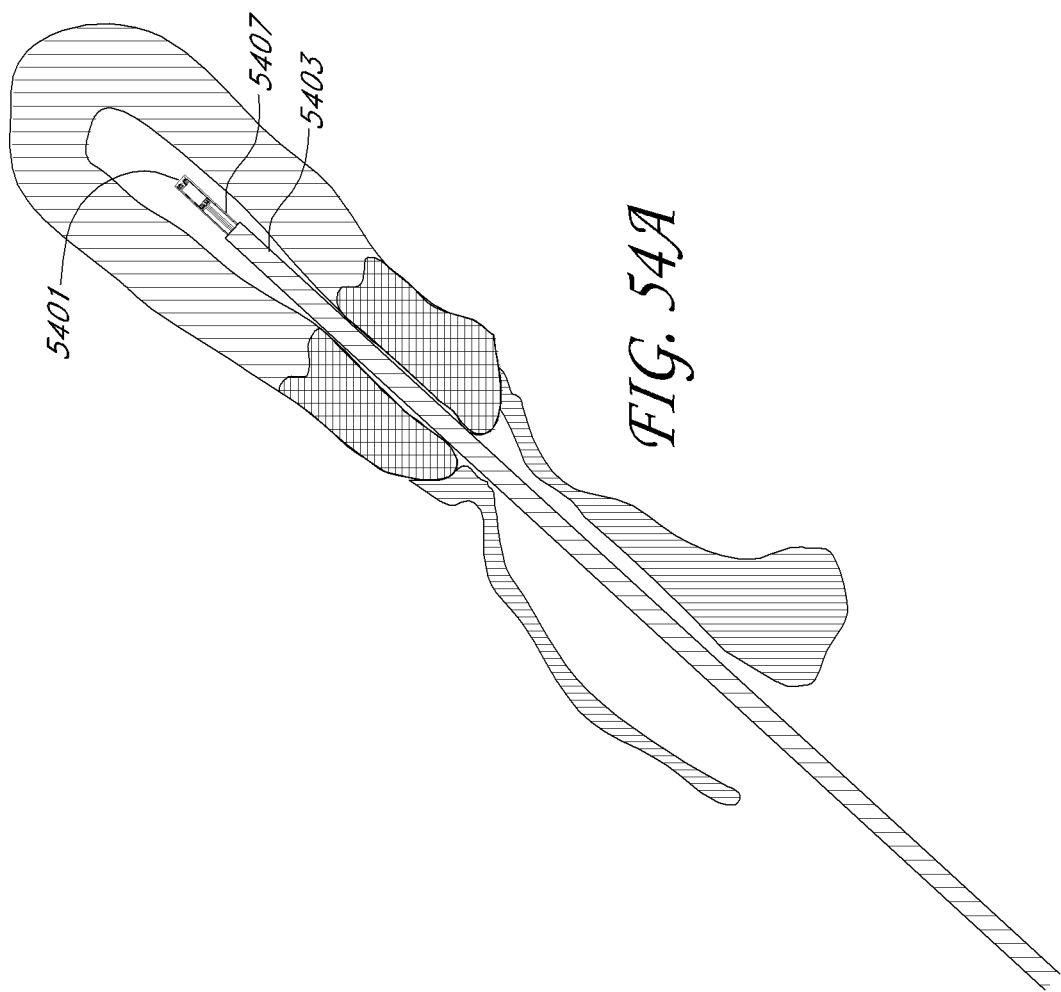
FIG. 54B
FIG. 54A

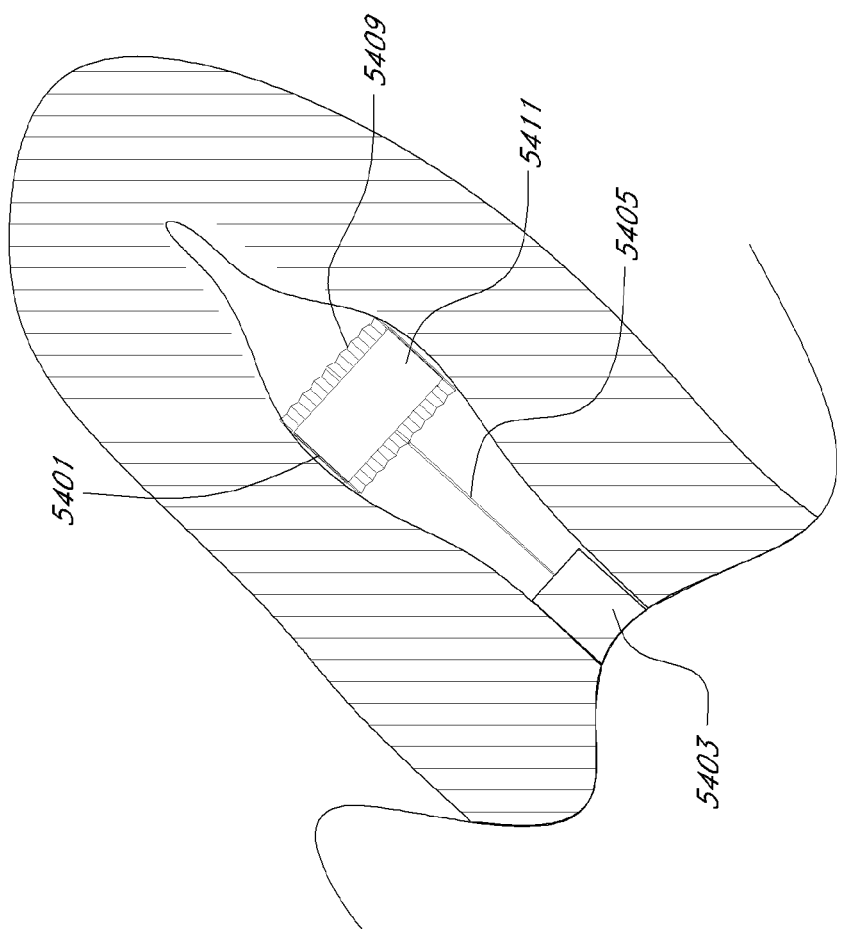
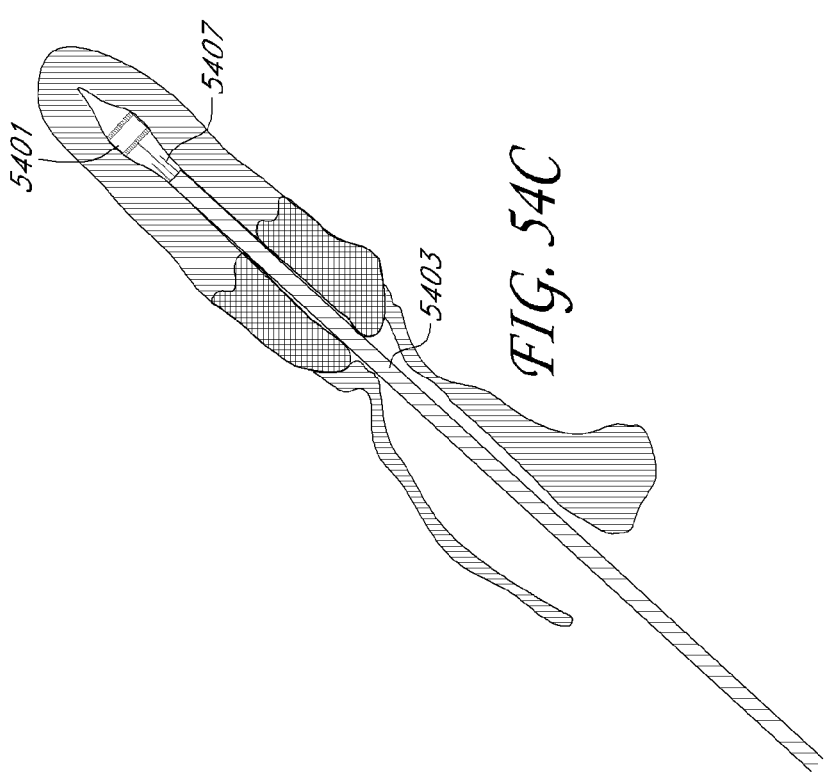
FIG. 54D
FIG. 54C

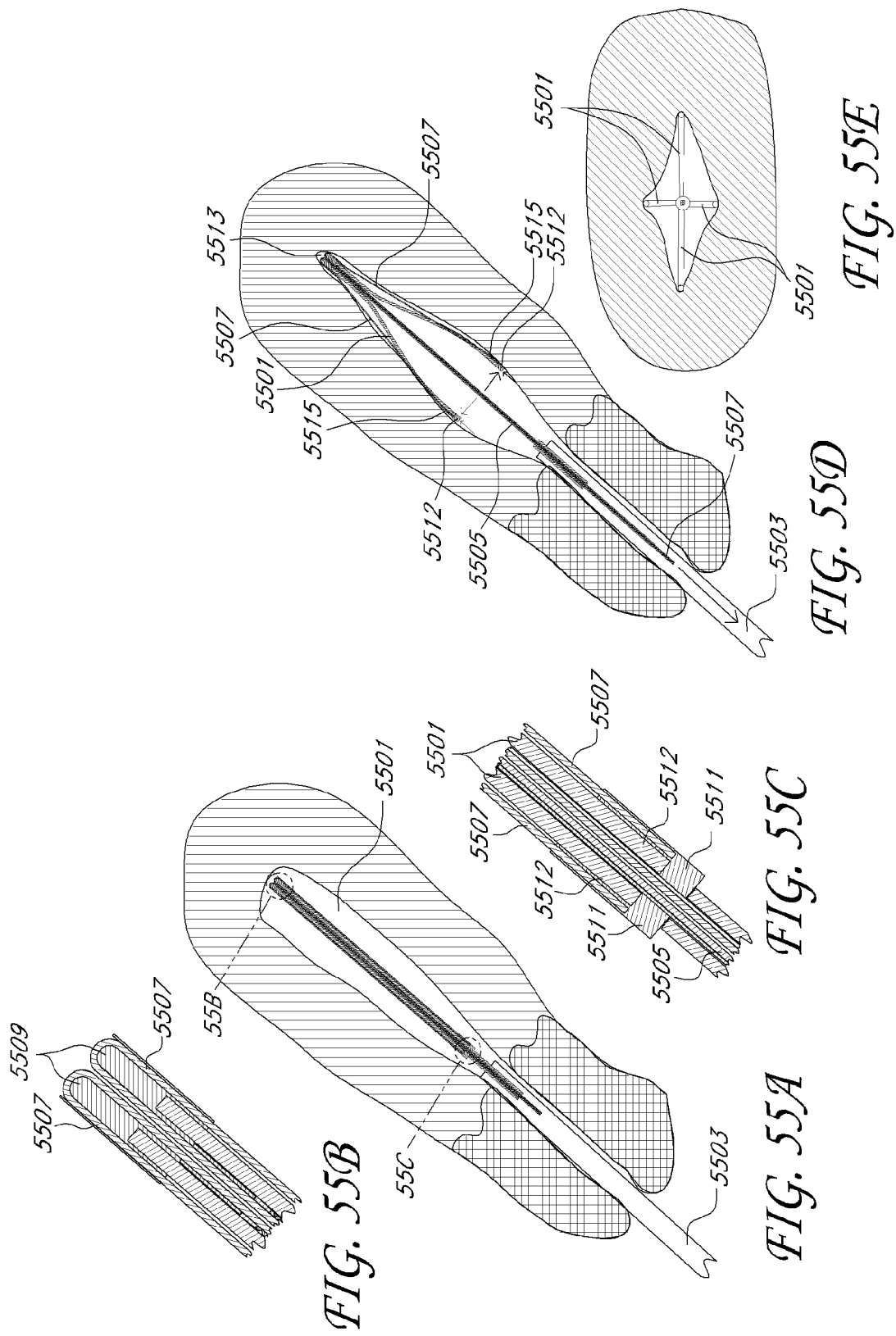

METHOD AND DEVICE FOR DISTENDING A GYNECOLOGICAL CAVITY

CROSS-REFERENCE TO RELATED APPLICATIONS

The present application claims the benefit under 35 U.S.C. 119(e) of U.S. Provisional Patent Application Ser. No. 60/910,625, filed Apr. 6, 2007, and U.S. Provisional Patent Application Ser. No. 60/910,618, filed Apr. 6, 2007, all of which are incorporated herein by reference.

FIELD OF THE INVENTION

The invention is in the general field of medical tools, and more specifically relates to tools and methods involving distending a gynecological cavity.

DESCRIPTION OF THE RELATED ART

The present invention relates generally to methods and devices for distending a gynecological cavity and relates more particularly to a new method and device for distending a gynecological cavity.

It is desirable in many types of situations for medical personnel to perform diagnostic and/or therapeutic procedures within a gynecological cavity. For example, one may wish to detect and/or to treat conditions including, but not limited to, the presence of fibroids, polyps, tumors, adhesions, or other abnormalities within a uterus; endometriosis or other abnormal bleeding; uterine prolapse; ectopic pregnancy; and fertility issues (both the inability to conceive and the desire to avoid pregnancy). To facilitate the detection and/or the treatment of the above and like conditions, there should be ample space within the gynecological cavity for the procedure(s) in question to be performed. Unfortunately, however, in those instances in which the gynecological cavity in question is the uterine cavity, adequate space does not typically exist naturally. This is because the uterus is a flaccid organ. As such, the walls of the uterus are typically in contact with one another when in a relaxed state. Consequently, active steps need to be taken to create a working space within the uterus.

The conventional technique for creating such a working space within the uterus is to administer a fluid to the uterus, transcervically, under sufficient pressure to cause the uterus to become distended. Examples of the fluid used conventionally to distend the uterus include gases like carbon dioxide and liquids like water or certain aqueous solutions (e.g., a saline solution or a sugar-based aqueous solution).

Although the aforementioned technique of fluid distension is commonly practiced, there are certain risks associated therewith. For example, because the distending fluid is administered under pressure (which pressure may be as great as 80-100 mm Hg or greater), there is a risk that such fluids may be taken up by a blood vessel in the uterus, i.e., intravasation, which uptake may be quite harmful to the patient. This risk is particularly great when the fluid distension technique is followed by a procedure in which a blood vessel is cut, such as when an abnormal or undesired tissue located in the uterus is removed or ablated.

Moreover, the above-described technique of fluid distension suffers from additional shortcomings. For example, throughout the entire period of time that the diagnostic and/or therapeutic procedure is performed, the distension fluid must be continuously administered under pressure to the patient to keep the uterus distended. This requires the availability of an adequate supply of the distending fluid. In addition, suitable equipment must be available to provide the requisite continuous flow of distending fluid to the patient. Furthermore, the above-described fluid distension technique may become messy, particularly when a liquid is used as the distension fluid, as some of the distension fluid within the uterus may escape proper collection and, instead, may leak from the patient to the surrounding environment.

SUMMARY OF THE INVENTION

The present invention provides a novel method and device for distending a gynecological cavity, such as a uterine cavity.

In particular, the present invention provides methods and devices for distending a gynecological cavity that overcome at least some of the shortcomings described above in connection with existing methods and devices for distending a gynecological cavity.

Therefore, according to one aspect of the invention, there is provided a novel method and device for distending a gynecological cavity, said method and device utilizing a mechanical, non-fluid structure to distend the gynecological cavity. Such a structure may include, for example, self-expanding members, such as resilient baskets, coils, whisks, prongs, and loops, or mechanically expanded members, such as inflatable balloons, mechanically-expanded cages and loops, and scissor jacks. The distension structure may serve a purpose in addition to distension, such as illumination, imaging, irrigation, drug delivery, resection and cauterization.

More specifically, the distension structure could be preshaped to form a specific geometry (spherical or uterine-shaped) upon deployment.

The distension structure could act as an internal retractor, holding non-target tissue away from the target tissue.

The distension structure or structure could be partially covered to exclude some tissues via a covering of the distension members with material either porous or not.

The distension structure could have a loop or two that are independent from the others and that are electronically enabled to provide cautery or loop resection or mechanically enabled to provide grabbing and manipulation tasks while easily converting back to a distension mechanism.

The distension structure could be used in conjunction with another distension structure, i.e., "basket in a basket" configuration to have the outer distension structure providing retraction and visualization while the inner distension structure is used to manipulate, excise or cauterize tissue.

The distension structure could be equipped with a camera to allow for a "sky-cam" view of the operative area different than the primary (gun sight view).

The distension members of a distension structure could be illuminated if they are made of fiber optic material or glowing material or filled with chemical luminescent solutions or incorporate light sources (LED's).

The distension members of a distension structure could be inflatable, providing the user with individual strut control via preferential inflation (gases or liquids) of certain distension members.

The distension member stiffness could be varied by adjusting the pressure of inflatable or filled members.

The distension member geometry could be varied by changing the pressure and/or by selective inflation or filling of members.

The distension members could be hollow and equipped with side holes or end holes to conduct flushing of the distended space with therapeutic or non-therapeutic solutions.

The distension members could have uniform radial force or non-uniform radial force such that forces in the coronal or sagittal planes could be different. Likewise, the distension members could provide more or less force proximally or distally within the cavity.

The distension members could be made from shape memory materials, malleable or elastic materials.

The distension members could have a circular or non-circular cross-sectional shape to produce stiffness variations.

The distension members could include roller balls or roller barrels that can be energized to enable an endometrial ablation to be performed.

According to another aspect of the invention, there is provided a novel method for distending a gynecological cavity, said method comprising initially distending the gynecological cavity using fluid means and, thereafter, using mechanical, non-fluid means to maintain the gynecological cavity in a distended state.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIGS. 18(a) and 18(b) are section views of still yet another embodiment of a device for distending a gynecological cavity, the device being constructed according to the teachings of the present invention and being shown in a non-expanded state and in a partially-expanded state, respectively;

FIG. 19 is a section view of still yet another embodiment of a device for distending a gynecological cavity, the device being constructed according to the teachings of the present invention and being shown in a non-expanded state;

FIGS. 29(a) and 29(b) are top views, partly in section, illustrating a two-part method for distending a gynecological cavity in accordance with the teachings of the present invention;

FIGS. 33(a) and 33(b) are top views, partly in section, illustrating an alternate embodiment for distending a gynecological cavity using an inflatable or bladder cage.

FIG. 38 is a top view, partly in section, illustrating an alternate embodiment for distending a gynecological cavity using magnet blocks.

FIG. 39 is top view, partly in section, illustrating an alternate embodiment for distending a gynecological cavity using external and/or internal magnets.

FIGS. 51(a) and 51(b) are top views, partly in section, illustrating an alternate embodiment for distending a gynecological cavity using a spine linkage.

FIGS. 53(a) and 53(b) are top views, partly in section, illustrating an alternate embodiment for distending a gynecological cavity using nitinol wire having pivots.

FIGS. 54(a), 54(b), 54(c), and 54(d) are top views, partly in section, illustrating an alternate embodiment for distending a gynecological cavity using a bellows device.

FIGS. 55(a), 55(b), 55(c), 55(d), and 55(e) are top views, partly in section, illustrating an alternate embodiment for distending a gynecological cavity using an umbrella device.

DETAILED DESCRIPTION OF THE PREFERRED EMBODIMENT

Figure 1A:
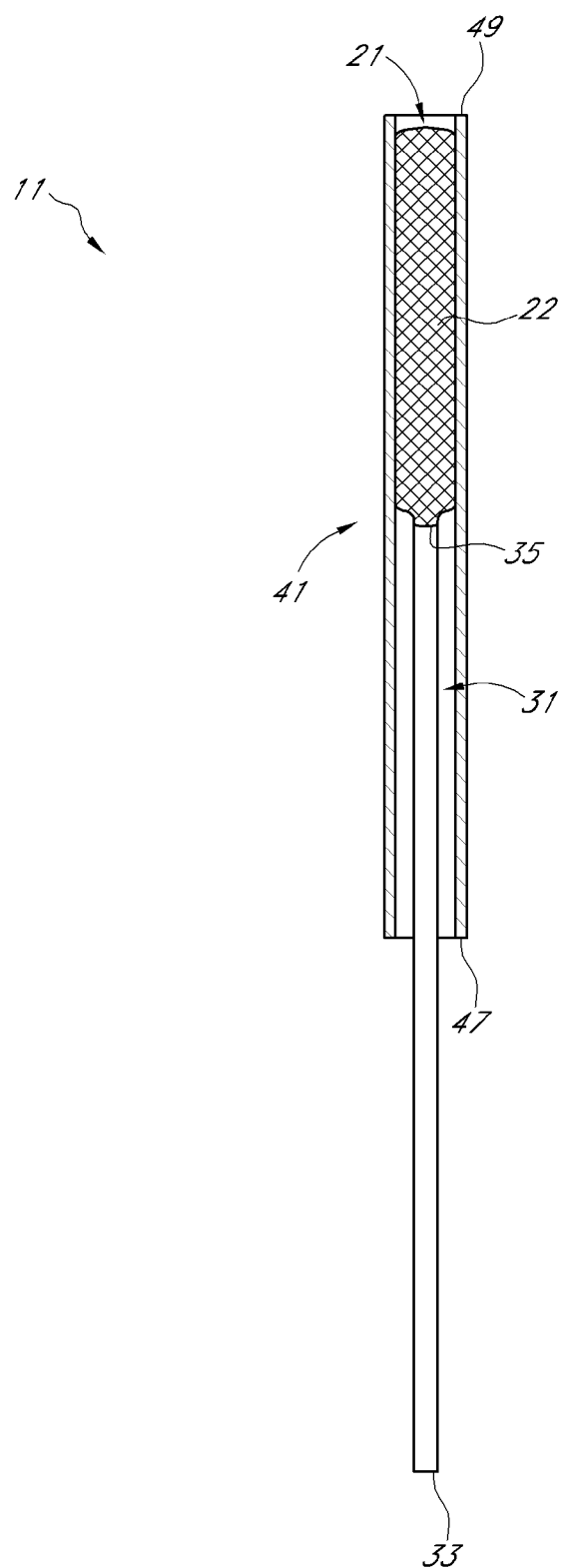
FIGS. 1(a) and 1(b) are top views, partly in section, of an embodiment of a device for distending a gynecological cavity, the device being constructed according to the teachings of the present invention and being shown in a compressed state and in an expanded state, respectively.
Figure 1B:
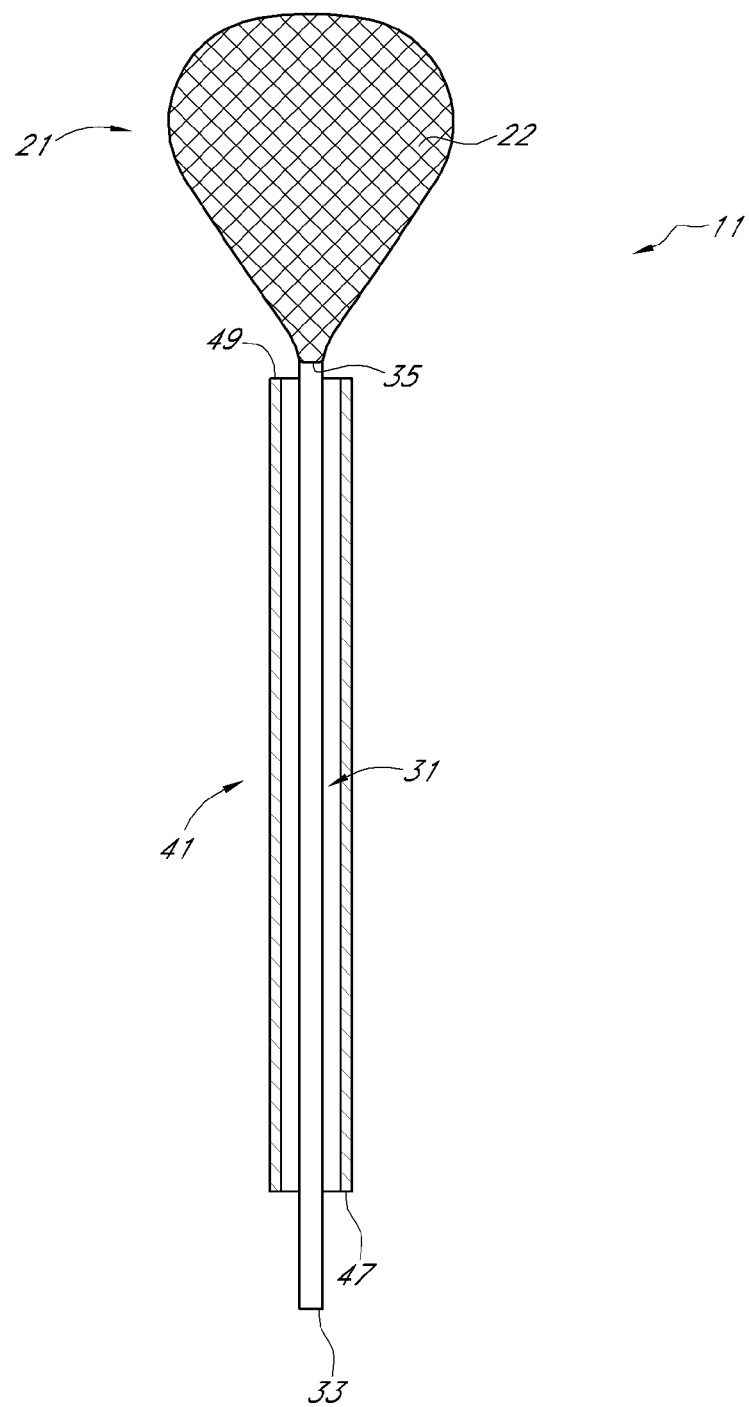

Referring now to FIGS. 1(a) and 1(b), there are shown top views, partly in section, of an embodiment of a device for distending a gynecological cavity, the device being constructed according to the teachings of the present invention and being represented generally by reference numeral 11. Additional features, methods and systems relating to the present invention are disclosed in U.S. patent application Ser. No. 11/923,357 filed Oct. 24, 2007, entitled Mechanical Distension Systems for Performing a Medical Procedure in a Remote Space, the disclosure of which is hereby incorporated in its entirety herein by reference.

Device 11, which is particularly well-suited for distending a uterus of a patient, comprises expandable means. In the present embodiment, said expandable means comprises a self-expanding basket 21. Basket 21 may be a resiliently-biased foldable weave of filaments 22 made of Nitinol (nickel-titanium alloy) shape-memory alloy, spring steel or a similar shape-memory material. Basket 21 may be constructed so that, when fully expanded within a uterus, it distends the uterus or a portion of the uterus to a desired extent. If desired, basket 21 may be constructed so that its expanded shape mimics the shape of the uterus. Preferably, basket 21 is constructed to distend the uterus to an extent equivalent to that which would be attained using the above-described conventional fluid distension technique at a pressure of at least 40 mm Hg but not greater than 100 mm Hg, often within the range of from about 60 mm Hg and about 80 mm Hg and preferably at a pressure of approximately 70 mm Hg for a typical patient. If desired, basket 21 may be constructed to provide a uniform radial force in all directions or may be constructed to provide different radial forces in different directions, such as along the coronal and sagittal planes.

The woven filaments 22 making up basket 21 may be sized and spaced (e.g., diameter, length, width) to effectively cover a small portion of the contacted surface area, thereby leaving large "windows" between adjacent filaments 22 through which diagnostic and/or therapeutic procedures may be performed; alternatively, filaments 22 may be sized and spaced to cover a large portion of the contacted surface area, with comparatively smaller "windows." It should be noted that, by appropriately sizing and positioning such "windows" over a target tissue, basket 21 may cause a target tissue to avulse through a window and into the interior of basket 21, where it may then be treated.

Device 11 may additionally comprise an elongated shaft 31, shaft 31 having a proximal end 33 and a distal end 35. Distal end 35 of shaft 31 may be coupled to basket 21 so that placement of basket 21 may be effected by moving shaft 31. Shaft 31 may be a solid member or may be a tubular structure.

Device 11 may further comprise an outer sheath 41. Sheath 41, which may be a unitary, tubular member, has a proximal end 47 and a distal end 49. Distal end 49 is adapted to be inserted into the uterus transcervically, with proximal end 47 preferably remaining external to the patient. To minimize discomfort to the patient, such as by obviating the need for administration of an anesthetic to the patient, the outer diameter of sheath 41 (or at least that portion of sheath 41 inserted into the patient) is preferably less than about 5.5 mm. Also to minimize discomfort to the patient, sheath 41 may be bendable along its length. Shaft 31 may be slidably disposed within sheath 41, with proximal end 33 of shaft 31 preferably extending proximally relative to proximal end 47 of sheath 41 to facilitate access thereto by medical personnel. (Alternatively, instead of proximal end 33 of shaft 31 extending proximally relative to proximal end 47 of sheath 41, proximal end 33 of shaft 31 may be coupled to a handle, pull-wires, or comparable structure that extends proximally relative to the proximal end 47 of sheath 41 or that is otherwise easily accessible to medical personnel.) As can be seen, by appropriately positioning distal end 35 of shaft 31 relative to distal end 47 of sheath 41, basket 21 may be positioned within sheath 41, where it is maintained in a compressed state by sheath 41, or may be positioned distally relative to sheath 41, where it is free to expand to its expanded state.

Figure 2A:
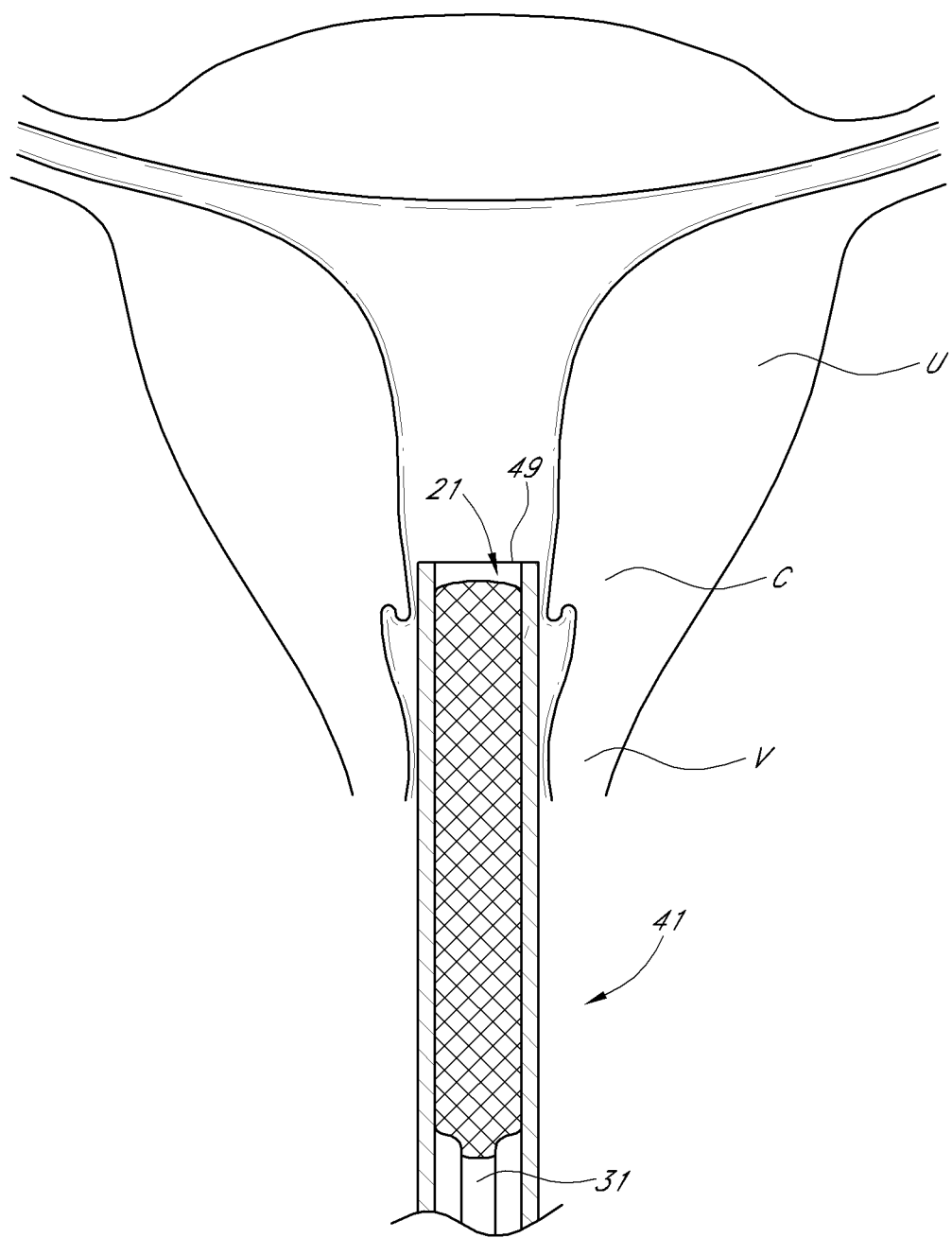
FIGS. 2(a) and 2(b) are fragmentary, schematic top views, partly in section, showing one way in which the device of FIGS. 1(a) and 1(b) may be used to distend a gynecological cavity, such as a uterine cavity.
Figure 2B:
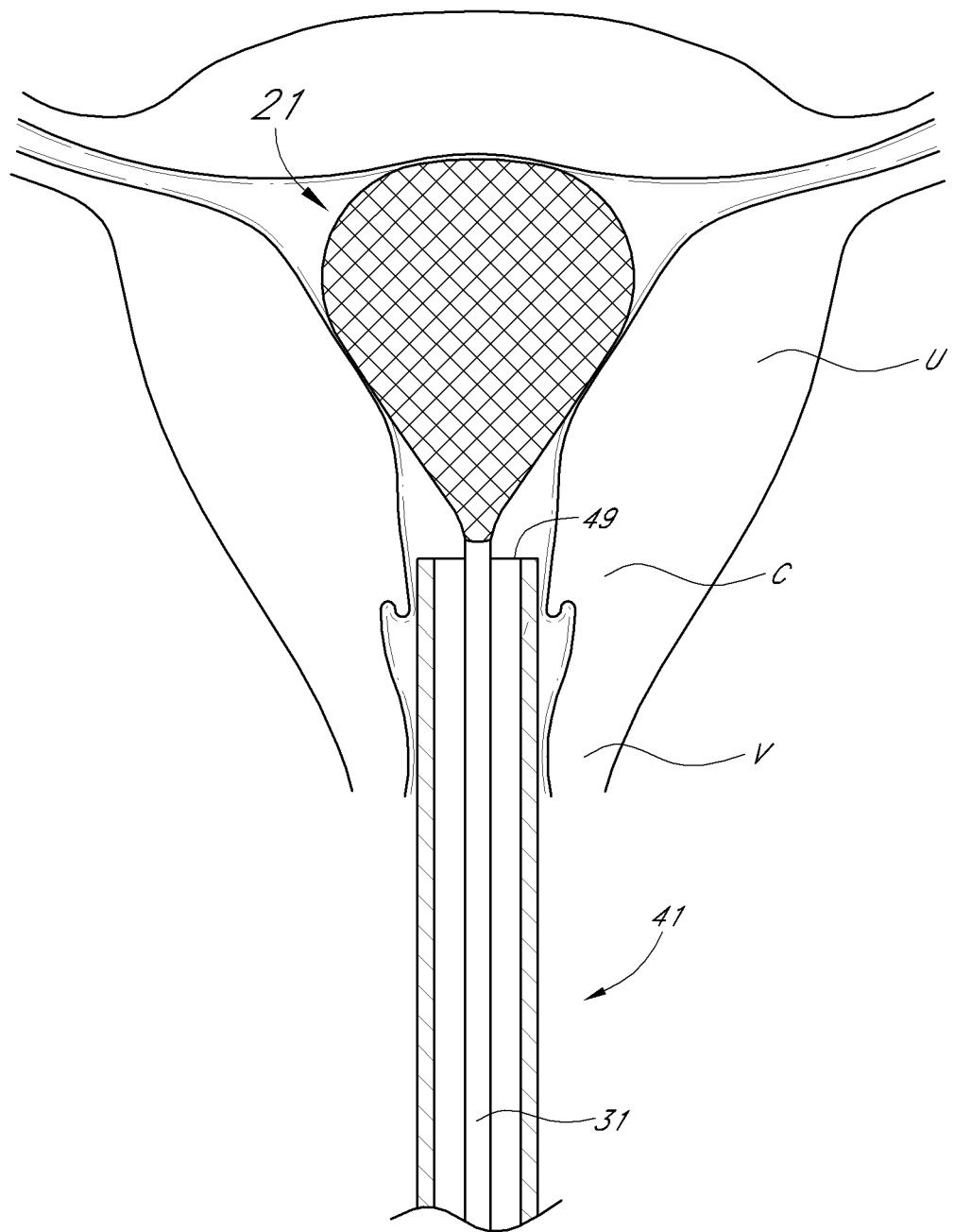

Referring now to FIGS. 2(a) and 2(b), there is shown one way in which device 11 may be used to distend a gynecological cavity, in particular, a uterine cavity. First, as shown in FIG. 2(a), while positioning shaft 31 relative to sheath 41 so that basket 21 is disposed within sheath 41 and is maintained therein in a compressed state, one inserts distal end 49 of sheath 41 into a patient first through vagina V and cervix C and then into uterus U (see FIG. 2(a)). Next, as shown in FIG. 2(b), while keeping sheath 41 stationary, one moves shaft 31 distally relative to sheath 41 until basket 21 emerges fully from distal end 49 of sheath 41, whereby basket 21 self-expands and, in so doing, distends the walls of uterus U (see FIG. 2(b)). With uterus U thus distended, one may perform one or more desired diagnostic and/or therapeutic procedures within uterus U. Such procedures may be performed by inserting one or more instruments coaxially through sheath 41 alongside of shaft 31 or, if shaft 31 is tubular, by inserting such one or more instruments coaxially through shaft 31 (and, thereafter, through the "windows" of basket 21). Alternatively, such instruments may be inserted transcervically into uterus U by being inserted alongside of, but not through, sheath 41. When distension of uterus U is no longer desired, shaft 31 is pulled proximally relative to sheath 41 until basket 21 is retracted into sheath 41, where it is compressed by sheath 41. Device 11 may then be withdrawn from the patient.

It should also be noted that, although neither described above nor shown in FIGS. 2(a) and 2(b), a separate introducer device may first be inserted transcervically into the patient, with device 11 thereafter inserted into the patient through a lumen in the introducer device. It should further be noted that, where such a separate introducer device is first inserted into the patient, sheath 41 may be omitted from device 11, with the lumen of the introducer device serving the same purpose as sheath 41 of maintaining the expandable means in a compressed state during delivery to the uterus and withdrawal from the uterus.

It should also be understood that, although basket 21 is self-expanding in the present embodiment, basket 21 may or may not be resiliently biased and its expansion may be caused or assisted by other mechanical means, such as by an inflatable balloon, advanceable push rods which exert radial forces upon different portions of basket 21 and/or other mechanical means.

Figure 3A:
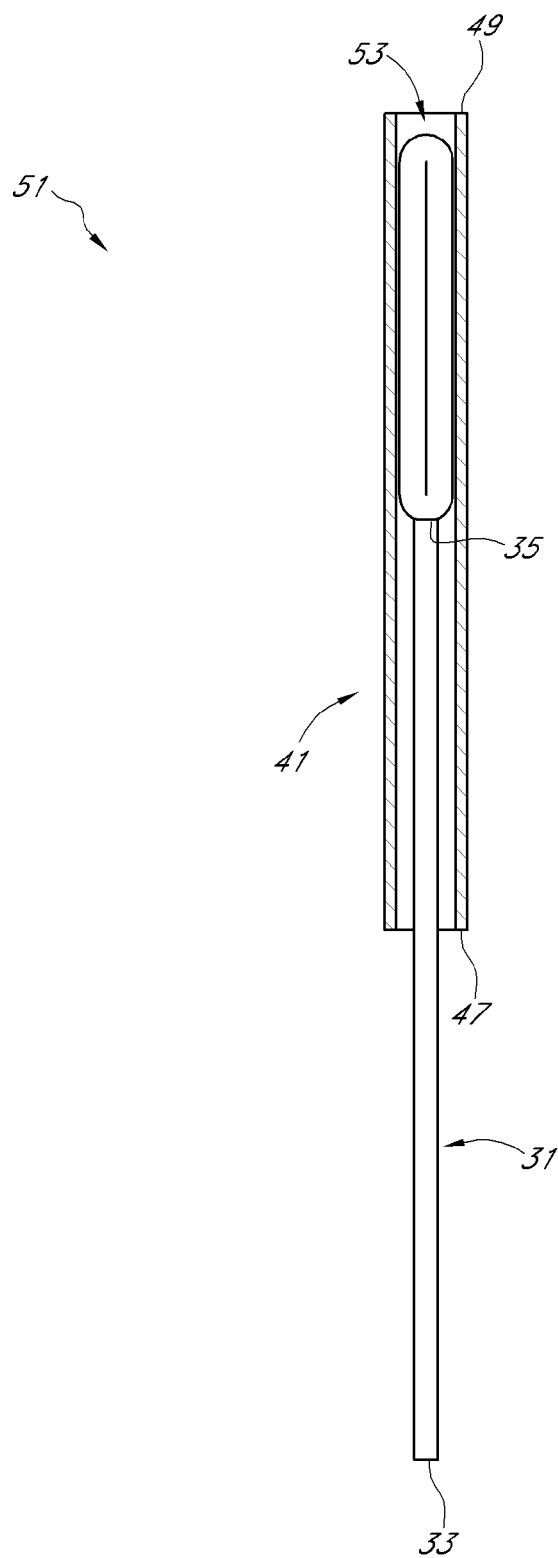
FIGS. 3(a) and 3(b) are top views, partly in section, of another embodiment of a device for distending a gynecological cavity, the device being constructed according to the teachings of the present invention and being shown in a compressed state and in an expanded state, respectively.
Figure 3B:
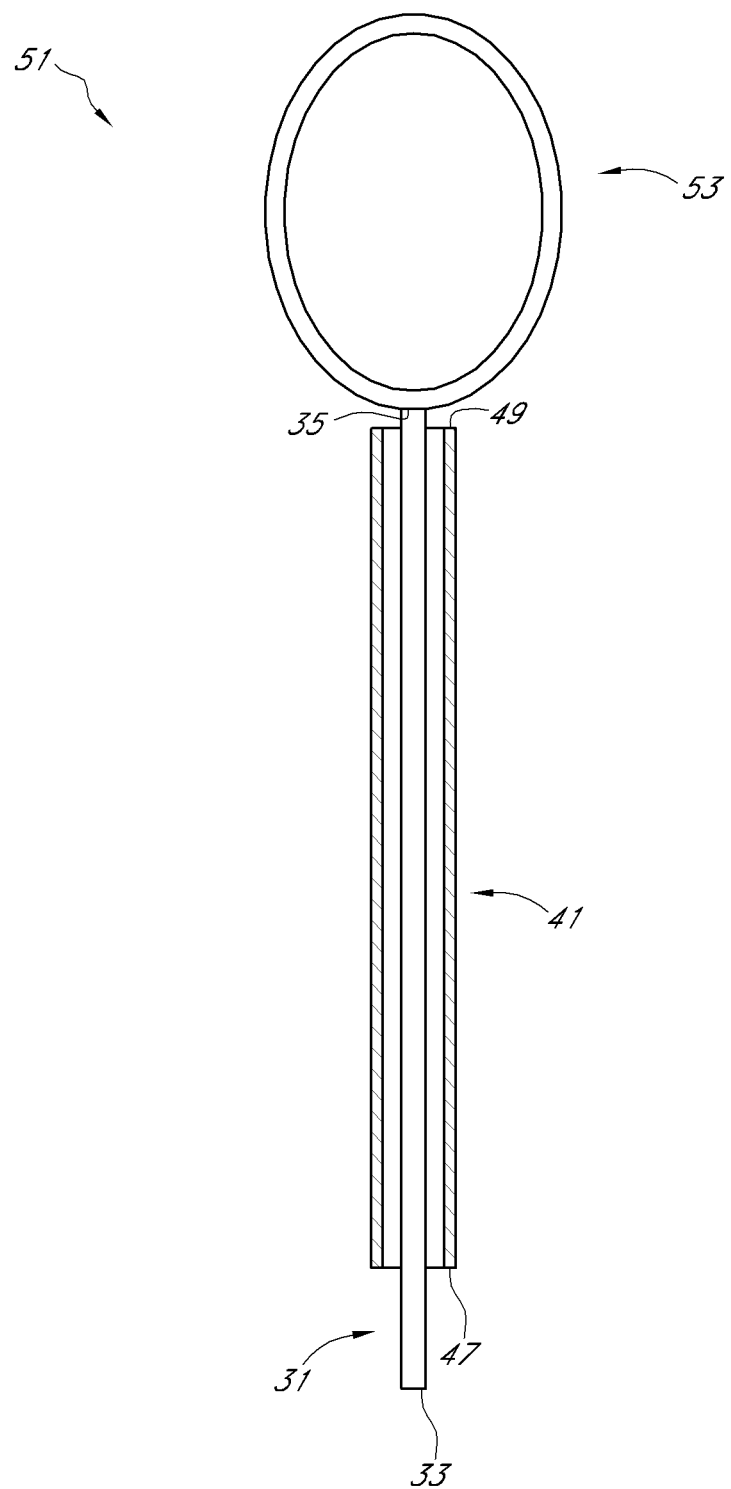

Referring now to FIGS. 3(a) and 3(b), there are shown top views, partly in section, of another embodiment of a device for distending a gynecological cavity, the device being constructed according to the teachings of the present invention and being represented generally by reference numeral 51.

Device 51 is similar in certain respects to device 11, the principal difference between the two devices being that, whereas device 11 includes expandable means in the form of basket 21, device 51 includes expandable means in the form of a self-expanding loop 53. Loop 53 is joined at its proximal end to shaft 31 and may be made from Nitinol (nickel-titanium alloy) shape-memory alloy, spring steel or a similar shape memory material. Loop 53 is appropriately constructed so that, when positioned within sheath 41, it is maintained in a radially compressed state (FIG. 3(a)) and so that, when positioned distally beyond sheath 41, it self-expands (FIG. 3(b)) to distend, to a desired extent, a gynecological cavity, such as a uterine cavity, or a portion thereof. Preferably, loop 53 is constructed to distend a uterus to an extent equivalent to that which would be attained using the above-described conventional fluid distension technique at a pressure of at least 40 mm Hg but not greater than 100 mm Hg and preferably at a pressure of approximately 70 mm Hg.

Device 51 may be used in a fashion similar to that described above in connection with device 11.

Figure 4:
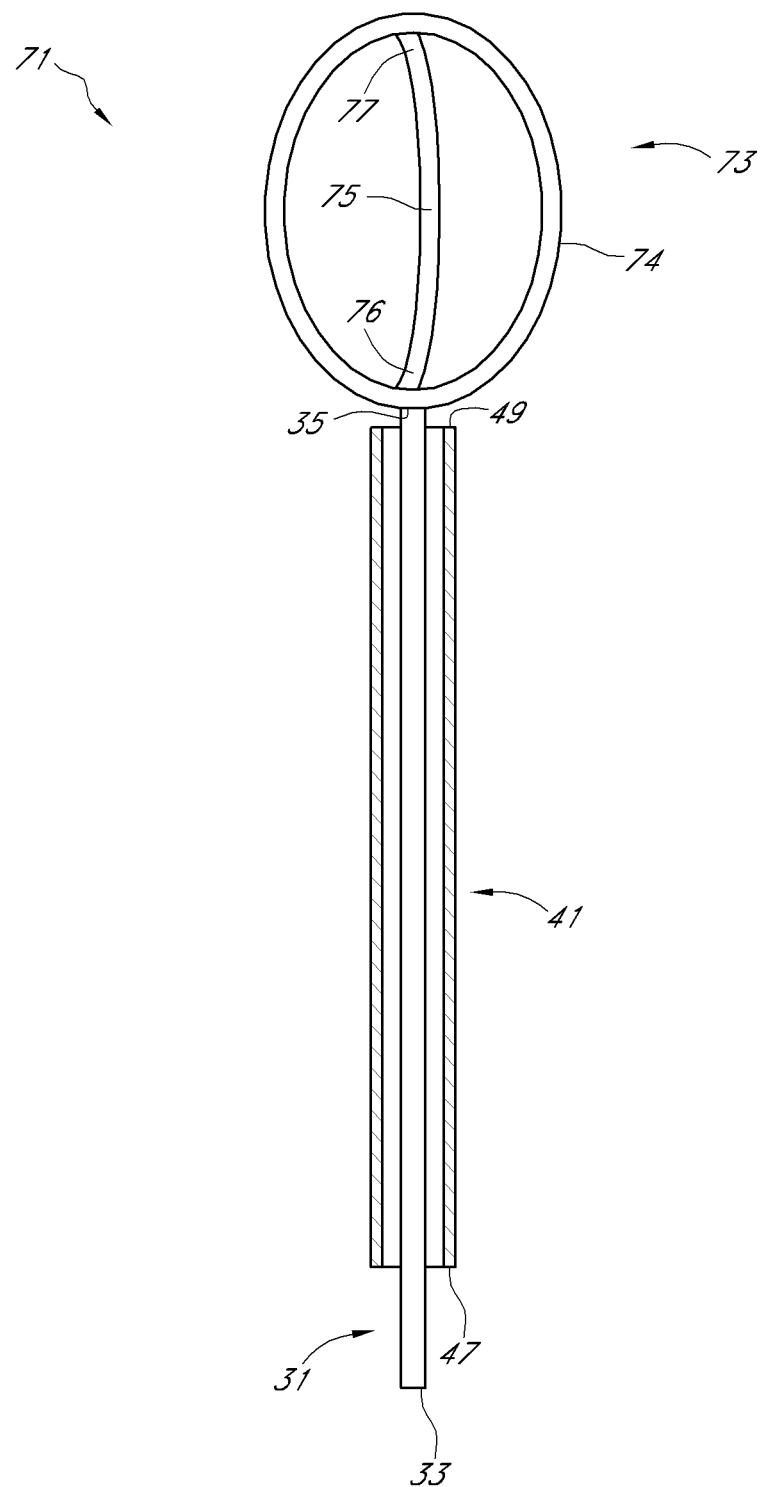
FIG. 4 is a fragmentary top view, partly in section, of still another embodiment of a device for distending a gynecological cavity, the device being constructed according to the teachings of the present invention and being shown in an expanded state.

Referring now to FIG. 4, there is shown a top view, partly in section, of still another embodiment of a device for distending a gynecological cavity, the device being constructed according to the teachings of the present invention and being represented generally by reference numeral 71.

Device 71 is similar in most respects to device 51, the principal difference between the two devices being that, whereas device 51 includes expandable means in the form of loop 53, device 71 includes expandable means in the form of a self-expanding structure 73. Structure 73 includes a resilient loop 74, which is similar to loop 53, and further includes a resilient arm 75, which is fixed at its proximal end 76 to the proximal end of loop 74 and is fixed at its distal end 77 to the distal end of loop 74. When structure 73 is in its expanded state, arm 75 serves to distend the gynecological cavity in a direction substantially perpendicular to that of loop 74. (Where, for example, structure 73 is oriented within the uterus so that arm 75 is pressing in the direction of the bowels, it may be desirable to make arm 75 of a stiffer material than that which is used to make loop 74 so that arm 75 may counteract pressure exerted on the uterus by the bowels.) Structure 73 is joined at its proximal end to shaft 31 and may be made from Nitinol (nickel-titanium alloy) shape-memory alloy, spring steel or a similar shape memory material. Structure 73 is appropriately dimensioned so that, when positioned within sheath 41, it is maintained in a radially compressed state and so that, when positioned distally beyond sheath 41, it self-expands to distend a gynecological cavity, such as a uterine cavity, or a portion thereof. Preferably, structure 73 is constructed to distend the uterus to an extent equivalent to that which would be attained using the above-described conventional fluid distension technique at a pressure of at least 40 mm Hg but not greater than 100 mm Hg and preferably at a pressure of approximately 70 mm Hg.

Device 71 may be used in a fashion similar to that described above in connection with device 11.

Figure 5A:
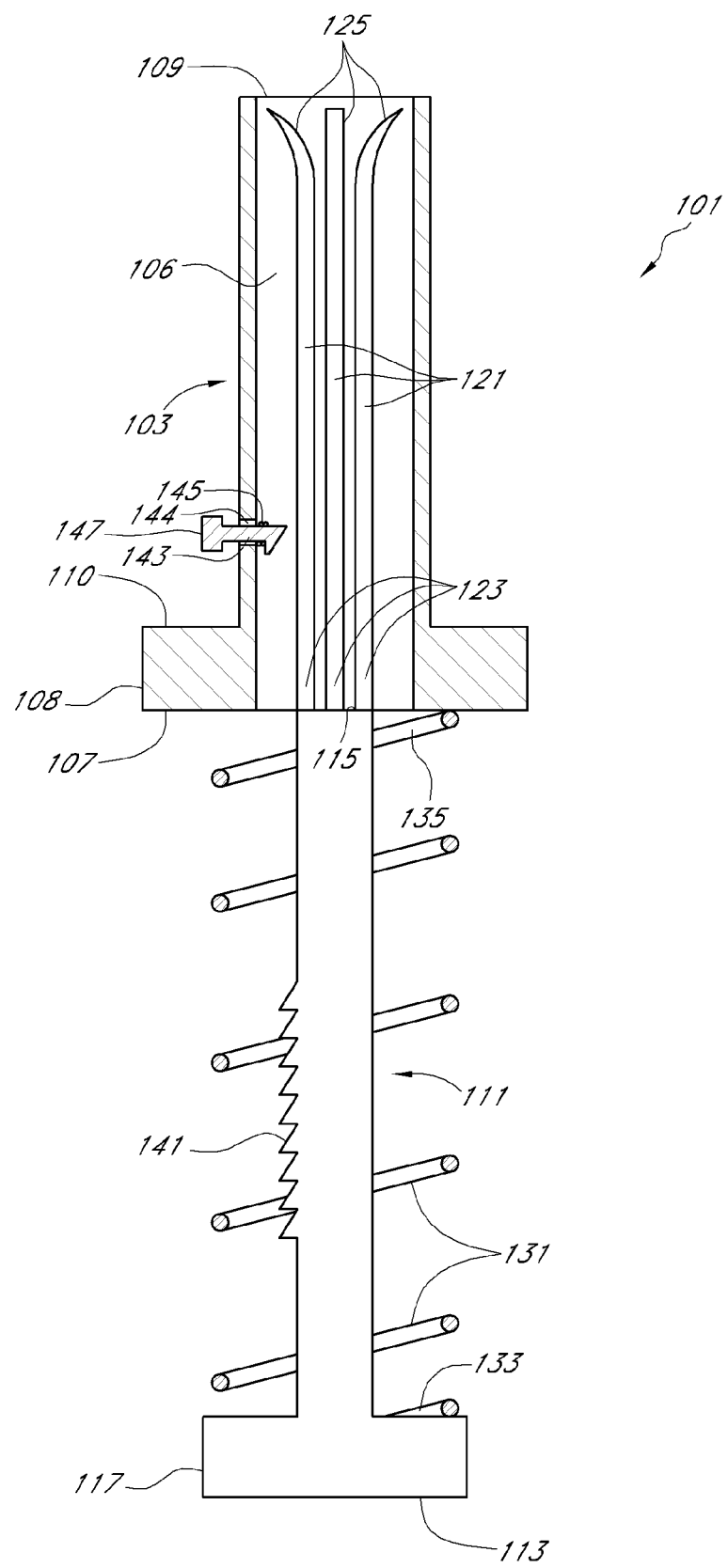
FIGS. 5(a) and 5(b) are top views, partly in section, of still yet another embodiment of a device for distending a gynecological cavity, the device being constructed according to the teachings of the present invention and being shown in a compressed state and in an expanded state, respectively.
Figure 5B:
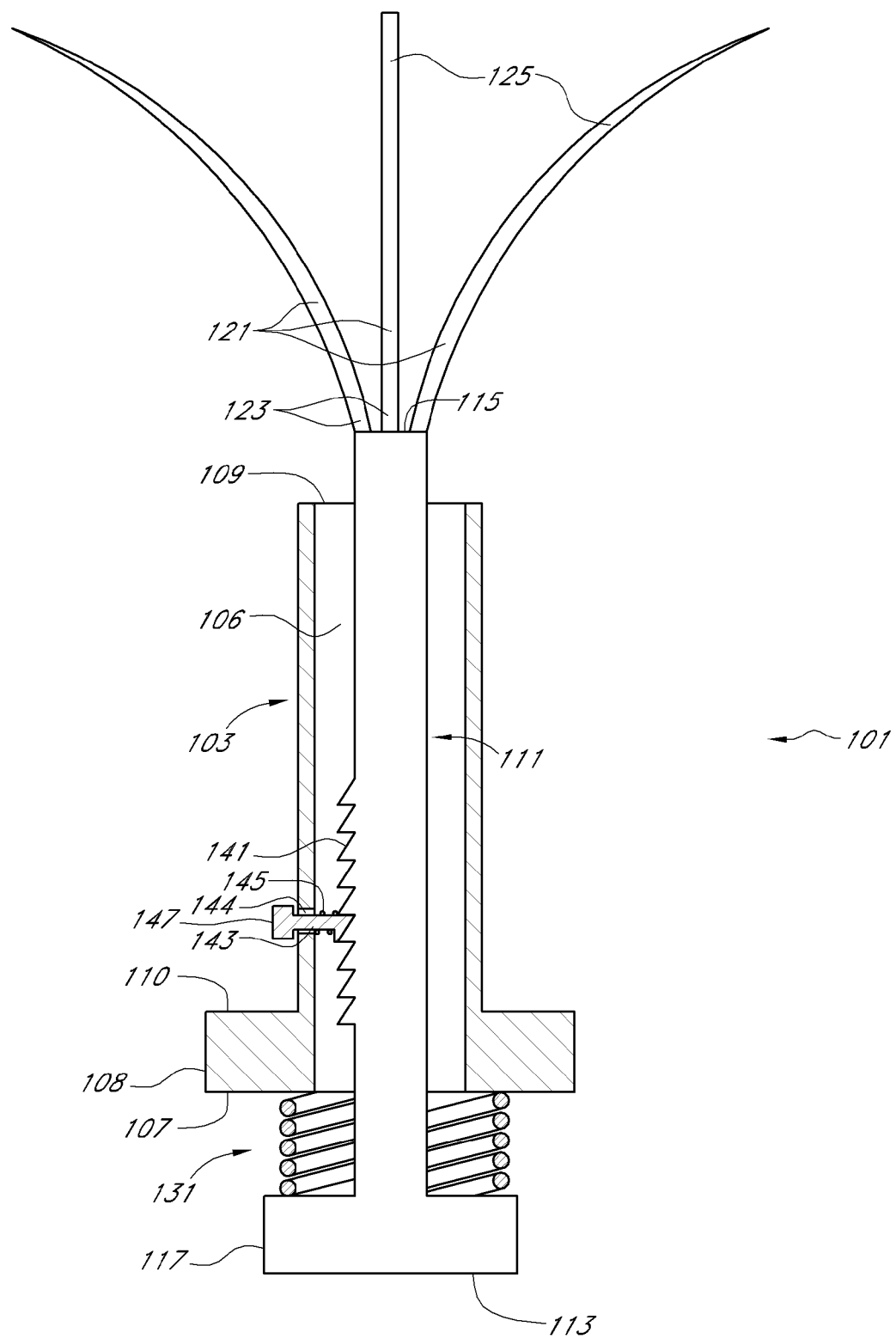

Referring now to FIGS. 5(a) and 5(b), there are shown top views, partly in section, of still yet another embodiment of a device for distending a gynecological cavity, the device being constructed according to the teachings of the present invention and being represented generally by reference numeral 101.

Device 101, which is particularly well-suited for distending the uterus of a patient, may comprise an outer sheath 103. Sheath 103, which may be a unitary, tubular member, may be shaped to include a longitudinal lumen 106, a proximal end 107 and a distal end 109. Proximal end 107, which may remain external to the patient, may be shaped to include an outwardly-extending radial flange 108. Flange 108 may be appropriately dimensioned to accommodate, on its distal surface 110, two fingers of an operator, each finger on an opposite side of lumen 106. Distal end 109 may be adapted to be inserted into the uterus transcervically. To minimize discomfort to the patient, such as by obviating the need for administration of an anesthetic to the patient, the outer diameter of that portion of sheath 103 inserted into the patient is preferably less than about 5.5 mm.

Device 101 also may comprise an elongated shaft 111, shaft 111 having a proximal end 113 and a distal end 115. Proximal end 113 may be shaped to include an outwardly-extending radial flange 117, flange 117 being appropriately dimensioned to prevent its insertion into lumen 106 of sheath 103. Substantially the remainder of shaft 111 may be slidable within lumen 106 of sheath 103.

Device 101 additionally may comprise expandable means. In the present embodiment, said expandable means may comprise a plurality of elongated prongs 121. Each prong 121 may have a proximal end 123 and a distal end 125, each proximal end 123 being fixed to distal end 115 of shaft 111, each distal end 125 being free. Prongs 121 may be equally spaced apart around the perimeter of distal end 115 of shaft 111 and may be constructed to be outwardly-biased relative to the longitudinal axis of shaft 111. Prongs 121 may be made of Nitinol (nickel-titanium alloy) shape-memory alloy, spring steel, a shape-memory polymer, or a similar shape-memory material. As can be seen, by appropriately positioning distal end 115 of shaft 111 relative to distal end 107 of sheath 103, prongs 121 may be positioned within sheath 103, where they are maintained in a compressed state by sheath 103, or may be positioned distally relative to sheath 103, where they are free to assume their expanded configuration. Prongs 121 may be configured so that, when unrestrained by sheath 103, they distend the uterus or a portion of the uterus to a desired extent. Preferably, prongs 121 distend the uterus to an extent equivalent to that which would be attained using the above-described conventional fluid distension technique at a pressure of at least 40 mm Hg but not greater than 100 mm Hg and preferably at a pressure of approximately 70 mm Hg.

As can be appreciated, although the present embodiment includes three prongs 121, there may be a greater number of prongs 121 or a lesser number of prongs 121. Also, if desired, prongs 121 may be constructed from a resectable material so that an obstructing prong (e.g., a prong positioned over a target, such as a fibroid) may be removed, for example, by a morcellating device.

Device 101 further may comprise means for biasing shaft 111 proximally relative to sheath 103. In the present embodiment, said biasing means may comprise a coil spring 131. Coil spring 131 may be inserted coaxially over shaft 111, with the proximal end 133 of spring 131 engaging proximal end 113 of shaft 111 and with the distal end 135 of spring 131 engaging proximal end 105 of sheath 103. Spring 131 serves to bias shaft 111 proximally relative to sheath 103 and, therefore, biases prongs 121 towards their non-expanded configuration.

Device 101 further may comprise disengageable means for permitting movement of shaft 111 distally, but not proximally, relative to sheath 103. In the present embodiment, said means may comprise a ratchet 141, a pawl 143 and a spring 145. Ratchet 141 may be integrally formed along a portion of the length of shaft 111. Pawl 143 may be partially inserted through a transverse opening 144 in sheath 103. Spring 145 may be inserted coaxially over a portion of pawl 143 to bias pawl 143 towards engagement with ratchet 141. Pawl 143 may be shaped to include a handle 147. Handle 147 may be used to pull pawl 143 away from ratchet 141 when one wishes to disengage pawl 143 from ratchet 141.

To use device 101 to distend a gynecological cavity, such as a uterine cavity, one may first position shaft 111 relative to sheath 103 so that prongs 121 are disposed within sheath 103 and, as a result, are compressed by sheath 103 to their non-expanded configuration (as in FIG. 5(a)). One may then insert distal end 107 of sheath 103 into a patient first through the vagina and the cervix and then into the uterus. Next, while keeping sheath 103 stationary, one may then move shaft 111 distally relative to sheath 103 until prongs 121 emerge fully from distal end 107 of sheath 103, whereby prongs 121 assume their expanded configuration (as in FIG. 5(b)). Such movement of shaft 111 relative to sheath 103 may be accomplished by operating device 101 like a syringe, with the forefinger and the middle finger of one hand spaced apart against distal surface 110 of flange 108 and with the thumb of the same hand positioned against the proximal surface of proximal end 113 of shaft 111. As shaft 111 is moved distally relative to sheath 103, spring 131 becomes compressed; however, engagement of pawl 143 with ratchet 141 prevents spring 131 from returning to its decompressed state.

With prongs 121 in their expanded configuration, the walls of the uterus are distended, and one may perform one or more desired diagnostic and/or therapeutic procedures within the uterus. Such procedures may be performed by inserting one or more instruments coaxially through sheath 103 alongside of shaft 111 or, if shaft 111 is tubular, by inserting such one or more instruments coaxially through shaft 111 (and, thereafter, between adjacent prongs 121). Alternatively, such instruments may be inserted transcervically into uterus U by being inserted alongside of, but not through, sheath 103. When distension of the uterus is no longer desired, pawl 143 is pulled away from engagement with ratchet 141. This disengagement of pawl 143 from ratchet 141 removes the only restraint against spring 131 returning to its decompressed state; as a result, the disengagement of pawl 143 from ratchet 141 causes spring 131 to return to its decompressed state, thereby causing shaft 111 to be moved proximally relative to sheath 103 and, in turn, prongs 121 to be retracted into sheath 103. Device 101 may then be withdrawn from the patient.

It should be noted that coil 131 and/or the combination of ratchet 141, pawl 143, and spring 145 could be omitted from device 101, in which case the operator would manually maintain the relative axial positions of shaft 111 and sheath 103. It should also be noted that, although not described above, a separate introducer device may first be inserted transcervically into the patient, with device 101 thereafter inserted into the patient through a lumen of the introducer device. It should further be noted that, where such a separate introducer device is first inserted into the patient, sheath 103 (as well as coil 131, ratchet 141, pawl 143 and spring 145) may be omitted from device 101, with the lumen of the introducer device serving the same purpose as sheath 103 of maintaining the expandable means in a compressed state during delivery to the uterus and withdrawal from the uterus.

Figure 6A:
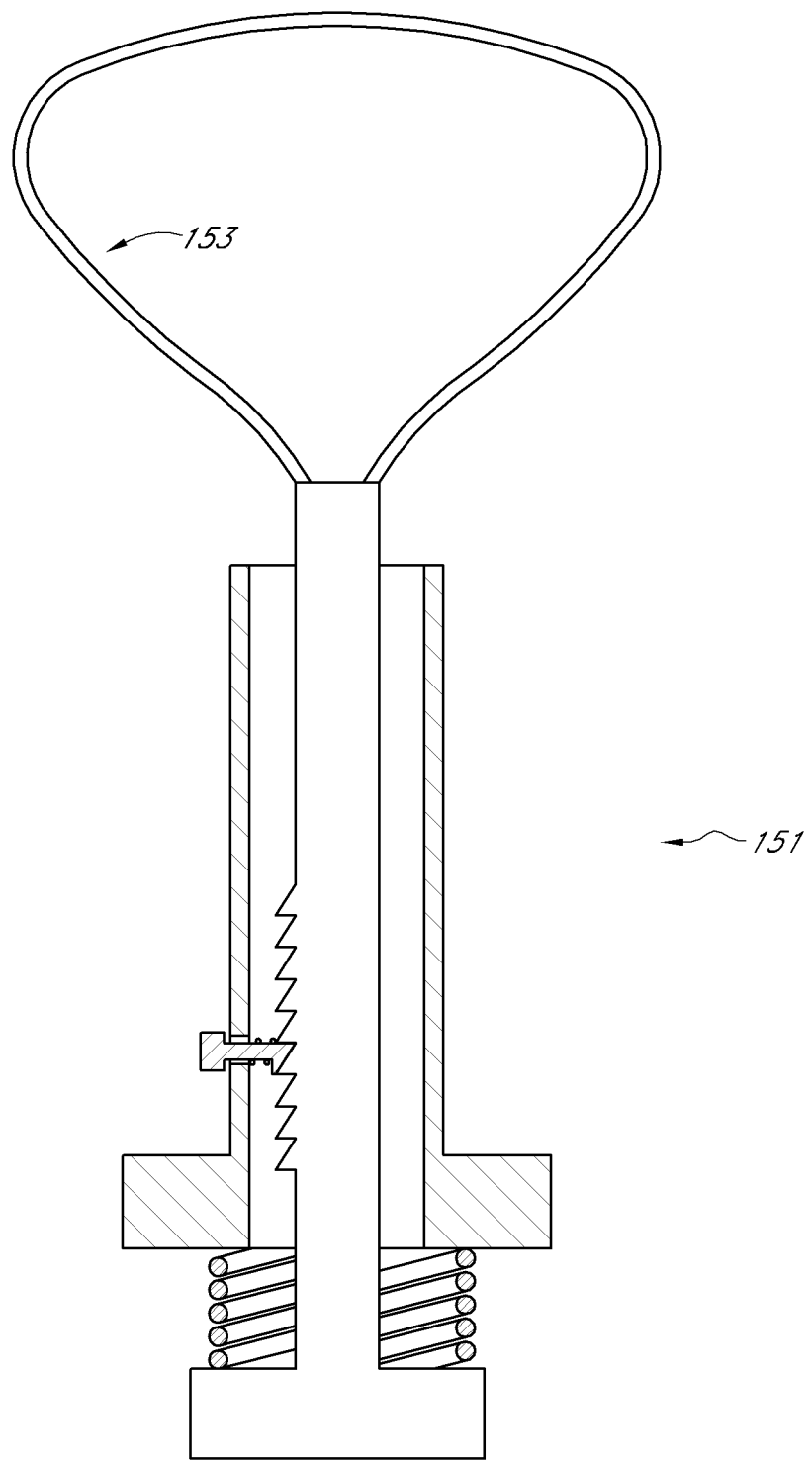
FIGS. 6(a) through 6(h) are top views of a number of alternate embodiments to the device shown in FIGS. 5(a) and 5(b), the alternate embodiments being constructed according to the teachings of the present invention and being shown in their respective expanded states.
Figure 6B:
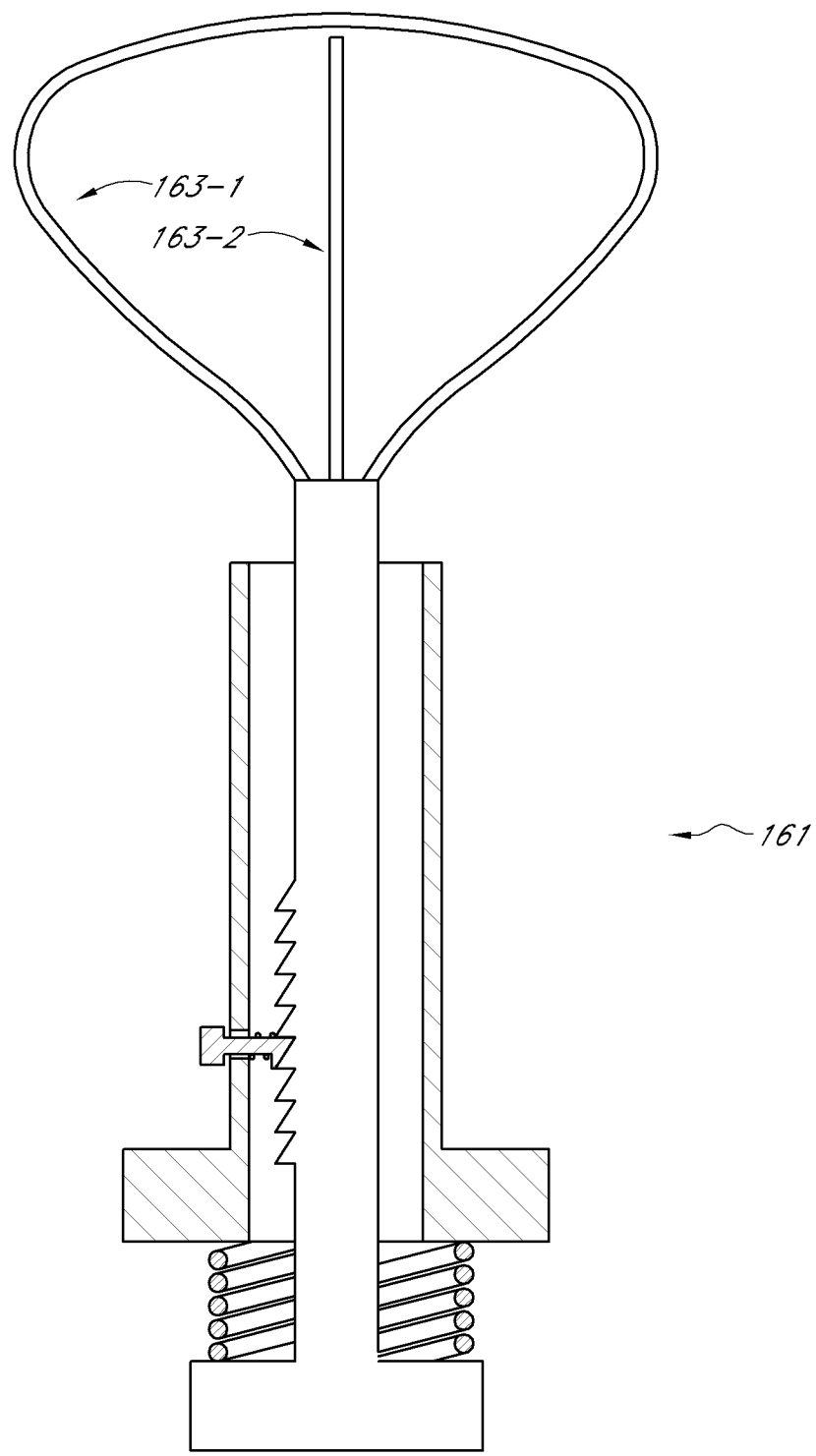
Figure 6C:
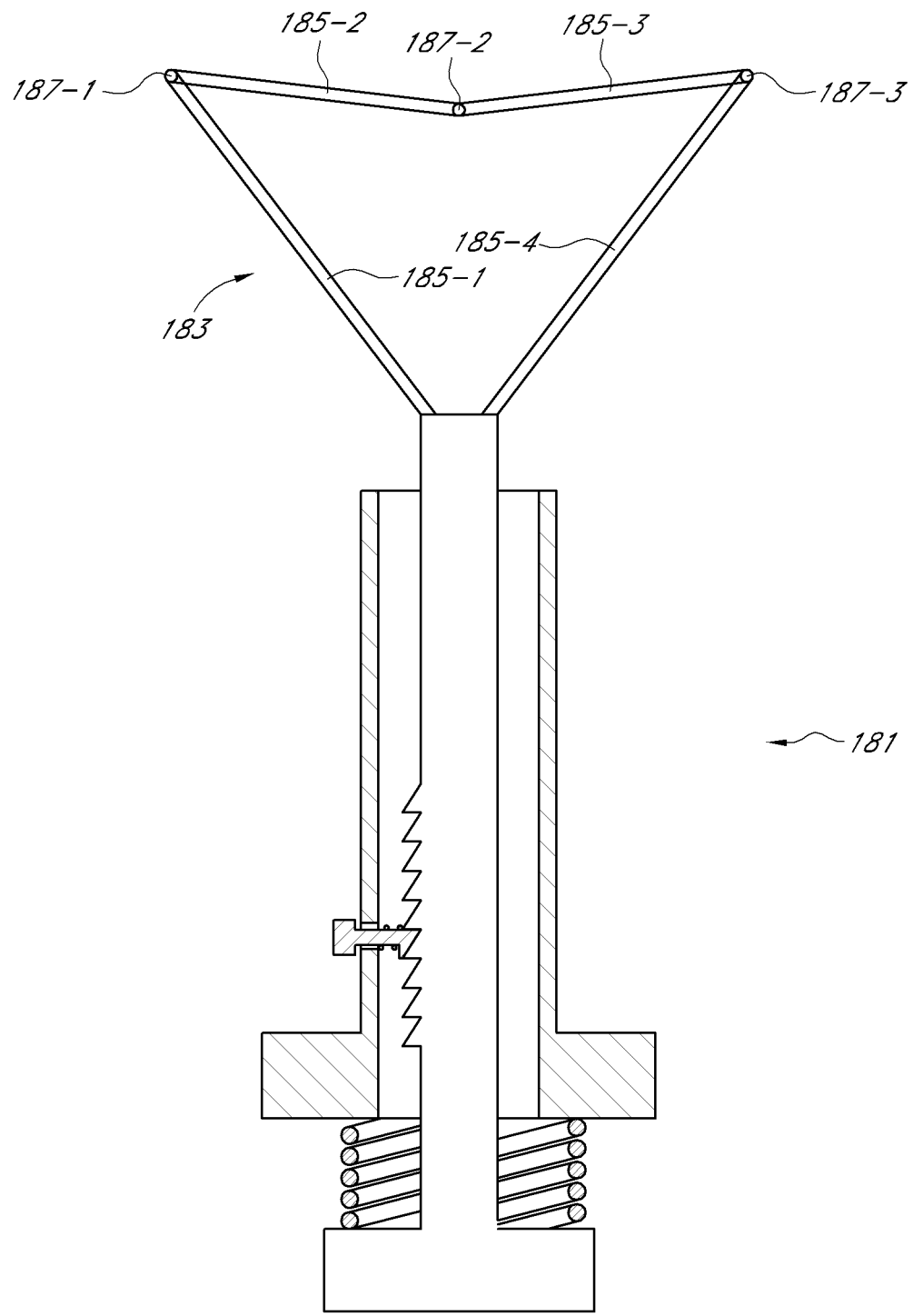
Figure 6D:
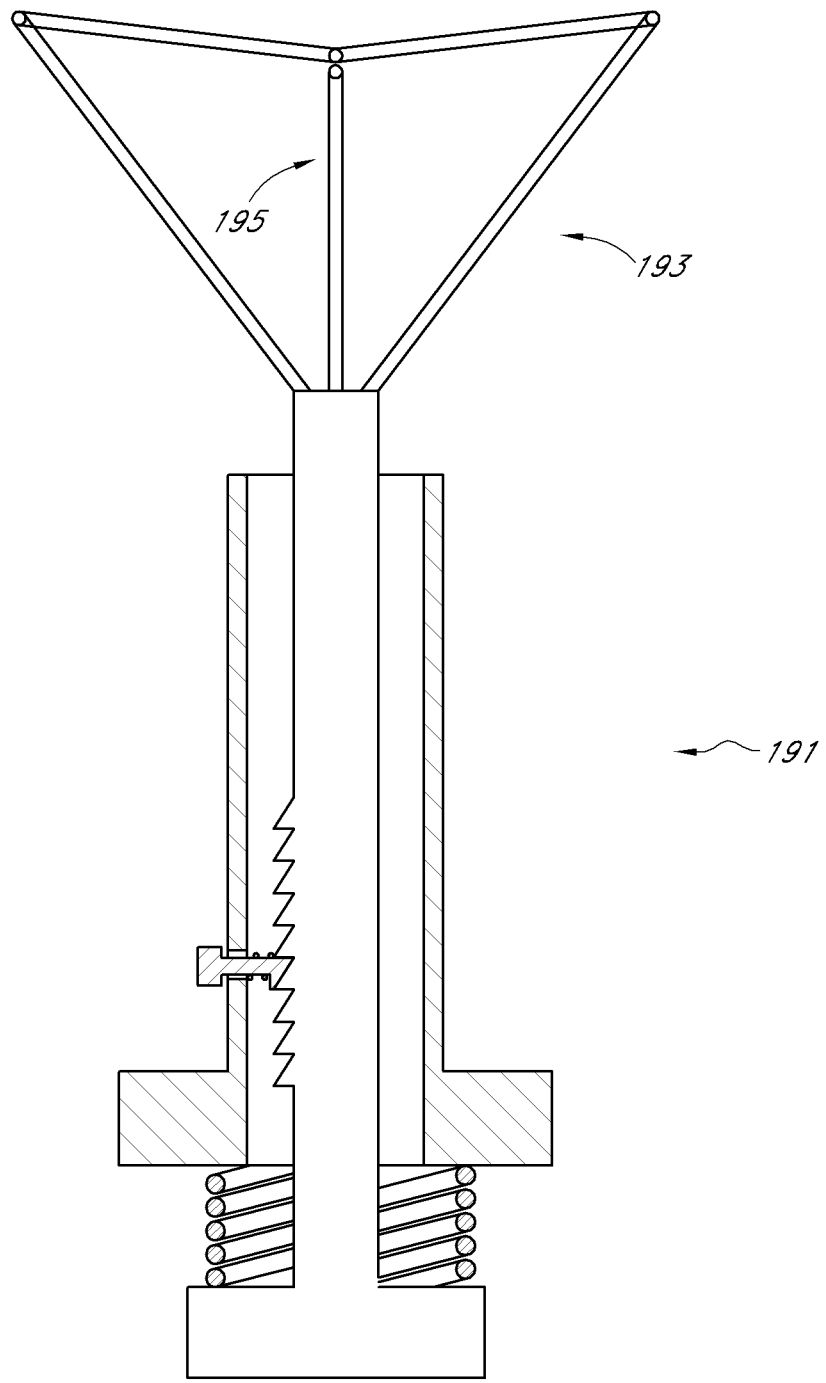

Referring now to FIGS. 6(a) through 6(h), there are shown top views, partly in section, of a number of alternate embodiments to device 101, said alternate embodiments differing from device 101 only in the construction of their respective self-expanding, expandable means. More specifically, in FIG. 6(a), there is shown a device 151, device 151 comprising expandable means in the form of a self-expanding loop 153. Loop 153 may have a quasi-triangular shape as shown to correspond generally to the shape of a uterus. In FIG. 6(b), there is shown a device 161, device 161 comprising expandable means in the form of a pair of self-expanding loops 163-1 and 163-2 arranged in a whisk-like configuration, with the distal end of loop 163-2 being positioned just inside the distal end of loop 163-1 and with loop 163-2 being oriented generally perpendicularly to the plane of loop 163-1. (Although, in the present embodiment, the distal end of loop 163-2 is positioned just inside the distal end of loop 163-1, device 161 may be modified so that loops 163-1 and 163-2 are of equal size and/or have a common distal end.) The radial forces applied by loops 163-1 and 163-2 may be substantially equal; alternatively, the radial forces applied by loops 163-1 and 163-2 may differ, for example, to apply different forces in the coronal and sagittal planes. In FIG. 6(c), there is shown a device 181, device 181 comprising expandable means in the form of a self-expanding cage-like structure 183, structure 183 comprising a plurality of rod-like members 185-1 through 185-4 pivotally joined end-to-end at joints 187-1, 187-2 and 187-3, respectively. Structure 183 may have a heart-like shape as shown to correspond generally to the shape of a uterus. In FIG. 6(d), there is shown a device 191, device 191 comprising expandable means in the form of a pair of self-expanding, cage-like structures 193 and 195. Structure 195 has a distal end positioned just inside the distal end of structure 193, with structure 195 being oriented generally perpendicularly to the plane of structure 193. As in the case of device 161, the radial forces applied by cage-like structures 193 and 195 may be substantially equal or may differ, for example, to apply different forces in the coronal and sagittal planes.

Figure 6E:
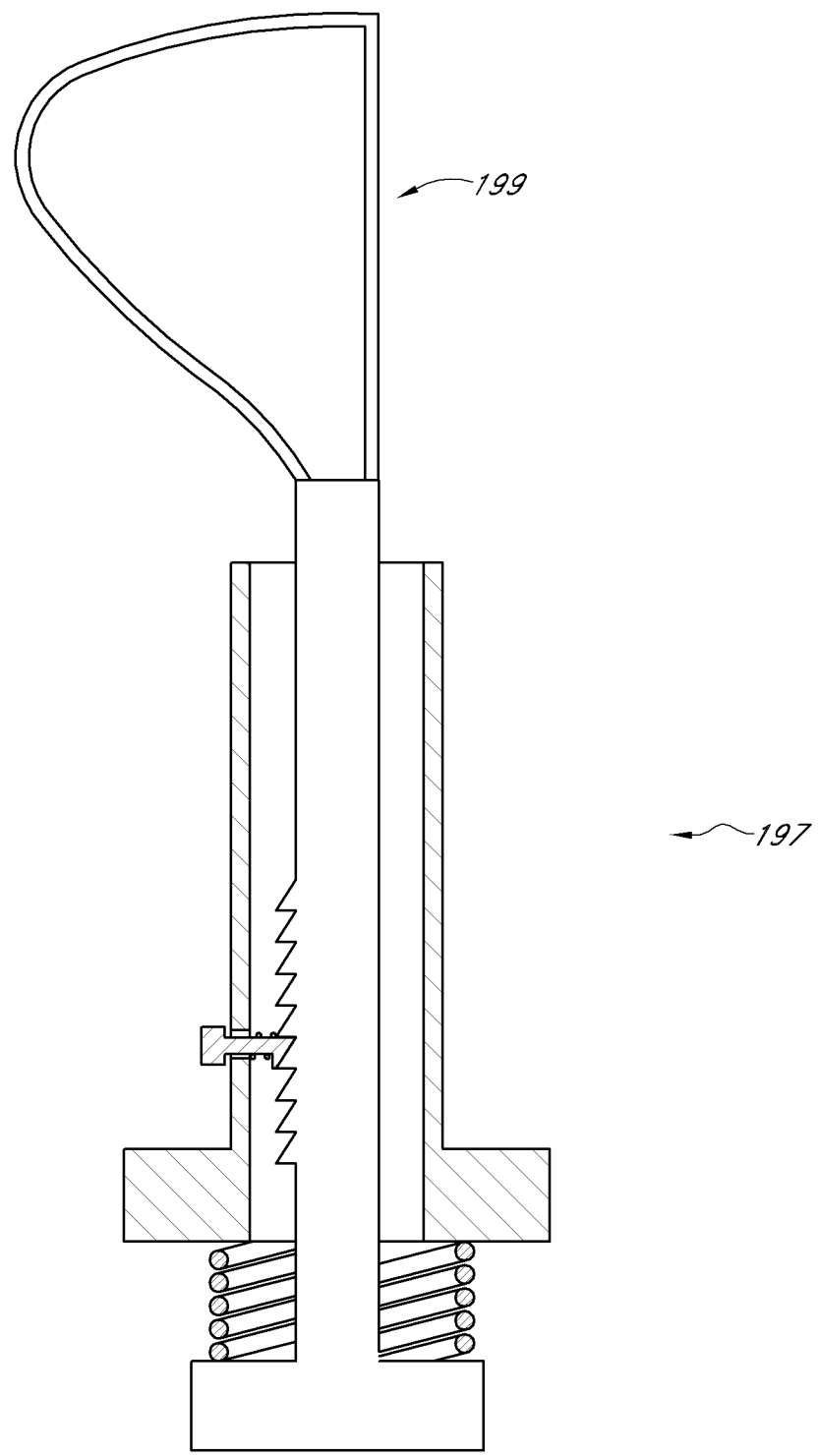
Figure 6F:
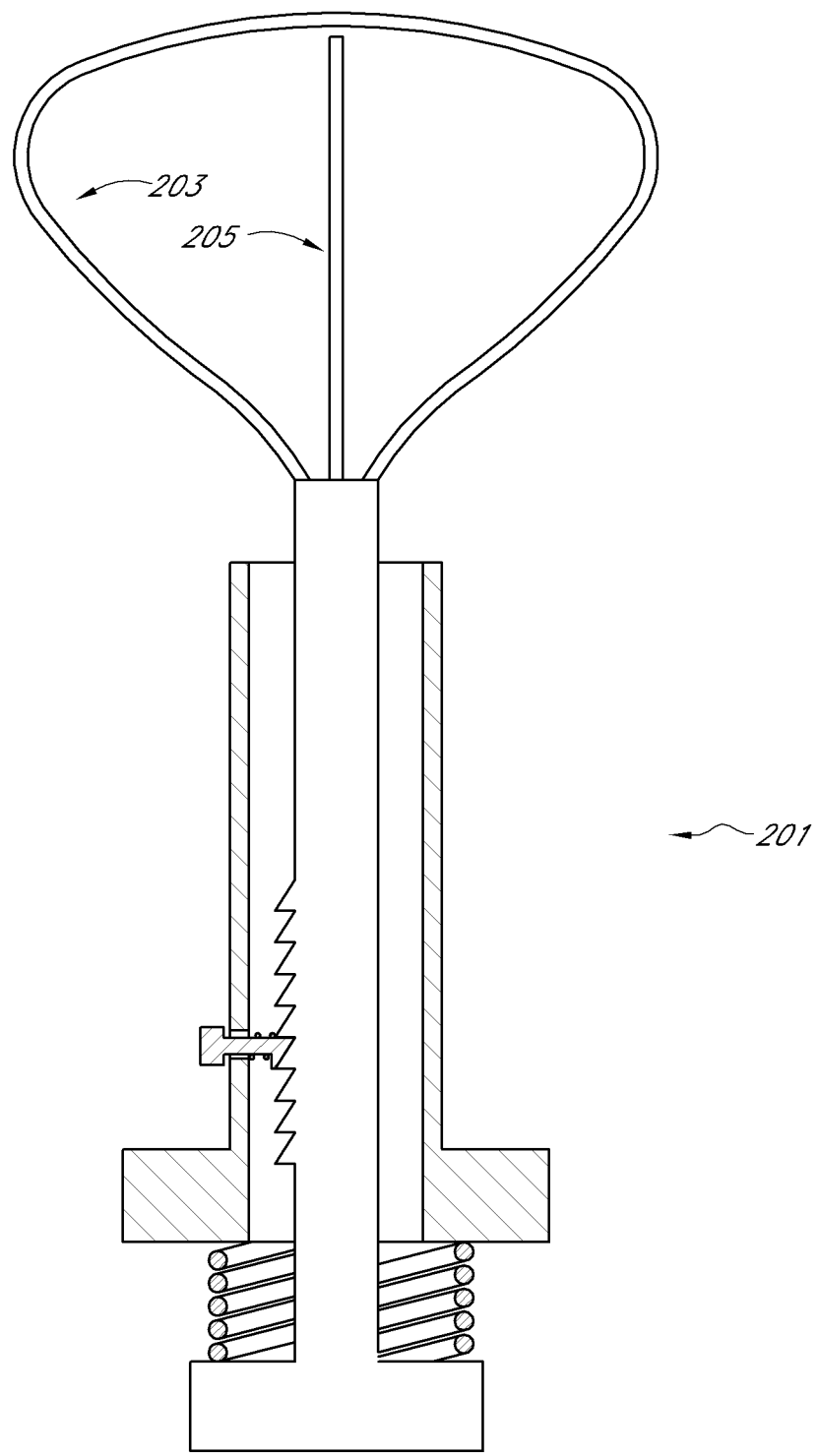
Figure 6G:
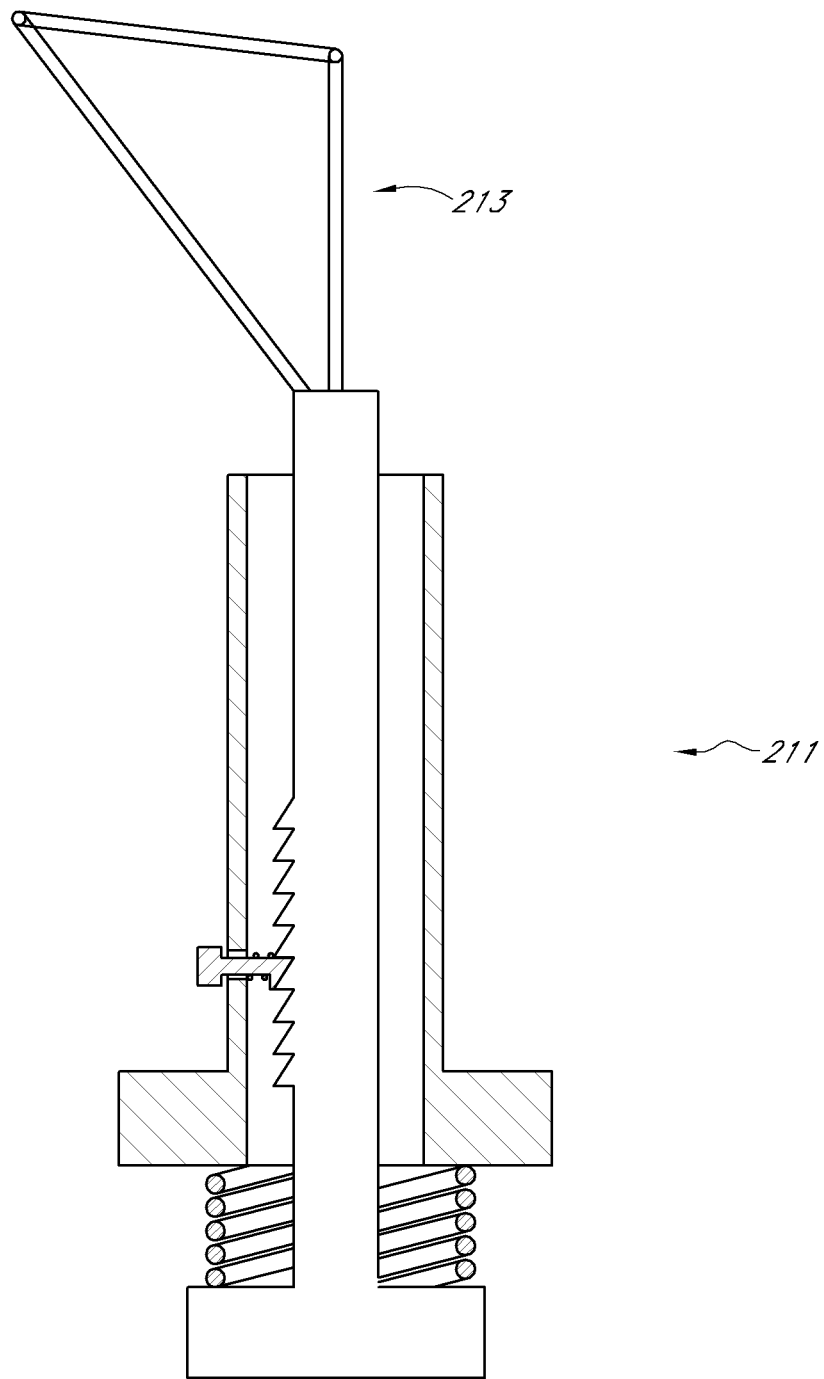
Figure 6H:
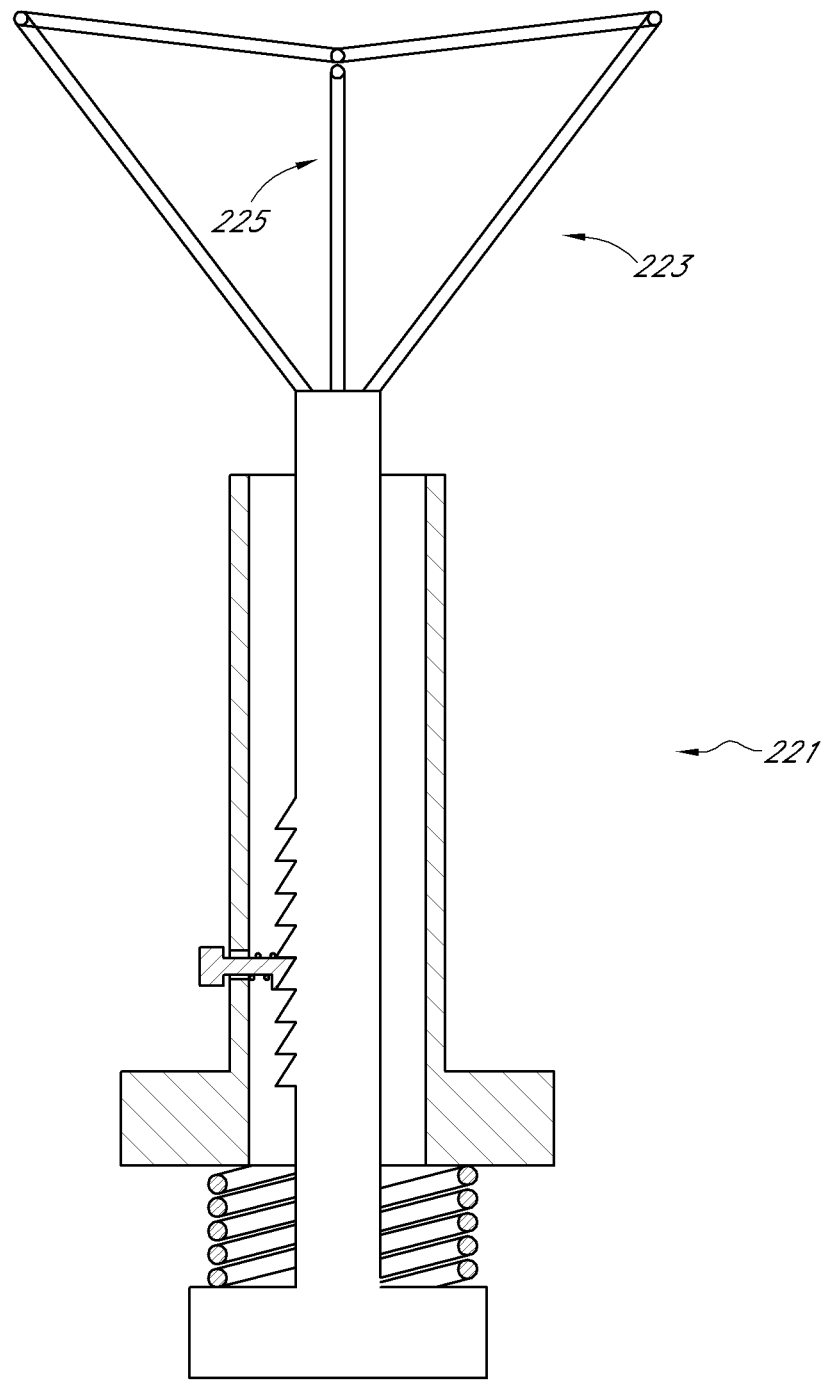

In FIG. 6(e), there is shown a device 197, device 197 comprising expandable means in the form of an asymmetric, self-expanding loop 199. Loop 199 may be useful in situations in which it is advantageous to distend only a portion of the uterus in order to create ample space to observe and/or to treat the non-distended portion. In FIG. 6(f), there is shown a device 201, device 201 comprising expandable means similar to the expandable means of device 161, except that device 201 comprises a symmetric loop 203 and an asymmetric loop 205 arranged in a whisk-like configuration, with the distal end of loop 205 being positioned just inside the distal end of loop 203 and with loop 205 being oriented generally perpendicularly to the plane of loop 203 but positioned only to one side of the plane of loop 203. Like device 197, device 201 may be useful in situations in which it is advantageous to distend only a portion of the uterus. In FIG. 6(g), there is shown a device 211, device 211 comprising expandable means in the form of an asymmetric, self-expanding, jointed structure 213. Like devices 197 and 201, device 211 may be useful in situations in which it is advantageous to distend only a portion of the uterus. In FIG. 6(h), there is shown a device 221, device 221 comprising expandable means in the form of a pair of cage-like structures 223 and 225. Device 221 is similar to device 191, the principal difference between the two devices being that cage-like structure 225 is asymmetric and is positioned only to one side of structure 223. Like devices 197, 201 and 211, device 221 may be useful in situations in which it is advantageous to distend only a portion of the uterus.

Figure 7:
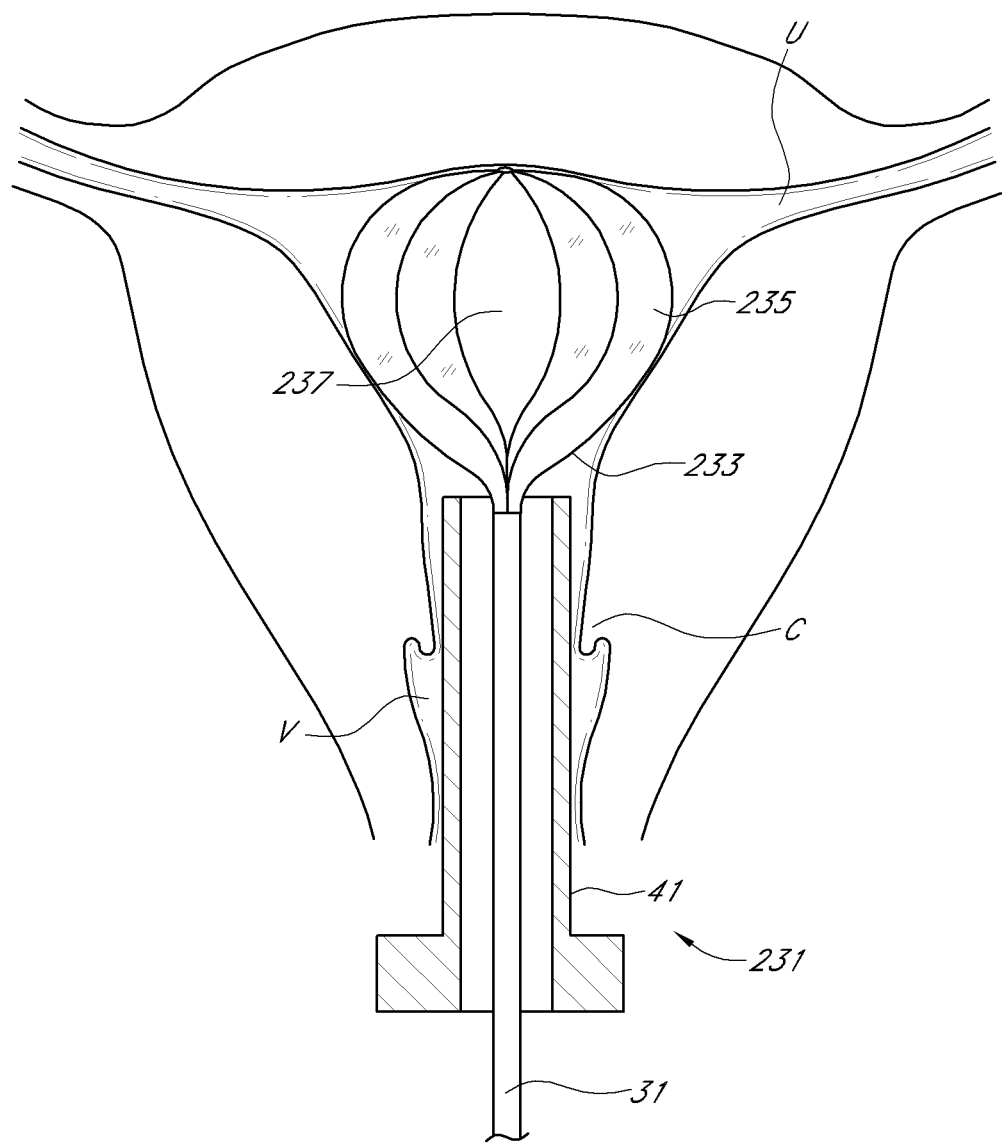
FIG. 7 is a top view, partly in section, of still yet another device for distending a gynecological cavity, the device being constructed according to the teachings of the present invention and being shown in an expanded state within a uterus.

Referring now to FIG. 7, there is shown a fragmentary top view, partly in section, of still yet another embodiment of a device for distending a gynecological cavity, the device being constructed according to the teachings of the present invention and being represented generally by reference numeral 231.

Device 231, which is shown in an expanded state within a uterus, is similar in many respects to device 11, the principal difference between the two devices being that, whereas device 11 comprises expandable means in the form of self-expanding basket 21, device 231 comprises expandable means that includes a self-expanding whisk 233 that is partially or completely covered on its inside or outside surface by a cover 235. Preferably, whisk 233 is constructed to distend the uterus to an extent equivalent to that which would be attained using the above-described conventional fluid distension technique at a pressure of at least 40 mm Hg but not greater than 100 mm Hg and preferably at a pressure of approximately 70 mm Hg.

Cover 235 may be made, for example, from a suitable fabric or polymer. In the present embodiment, cover 235 only partially covers whisk 233, with the uncovered portion of whisk 233 forming a window 237. The covered portions of whisk 233 may be used to keep the non-targeted portions of the gynecological cavity from entering into the interior space of whisk 233 whereas window 237 may be used to provide access to a target tissue through the interior space of whisk 233 or may be used to avulse a target tissue into the interior space of whisk 233.

In use, whisk 233 may be deployed within a gynecological cavity and then oriented, for example, by rotating shaft 31 (preferably partially compressing whisk 233 before rotating shaft 31), so that window 237 is aligned with a target mass, such as a fibroid. The radial pressure exerted by whisk 233 on the tissue surrounding the target mass may cause the target mass to avulse through the window 237 and into the interior space of whisk 233, where it may then be treated.

Alternatively, the covered portions of whisk 233 may be used to apply a tamponade force on a bleeding tissue location. Also, whisk 233 and/or cover 235 may be coated, impregnated or otherwise include one or more drugs, such as clotting agents and anesthetics. According to one embodiment, the drug may be "released" by a clinician on demand, such as by an integral iontophoretic delivery element (e.g., integral to whisk 233), or by applying a force to an integral pressure-activated drug depot (e.g., integral to whisk 233), and cover 235 may be used to administer such drugs to tissue by contact with the tissue. Additionally, whisk 233 and/or cover 235 may be coated or treated with one or more compounds to change a property, such as echogenicity, lubricity and radiopacity.

Figure 8:
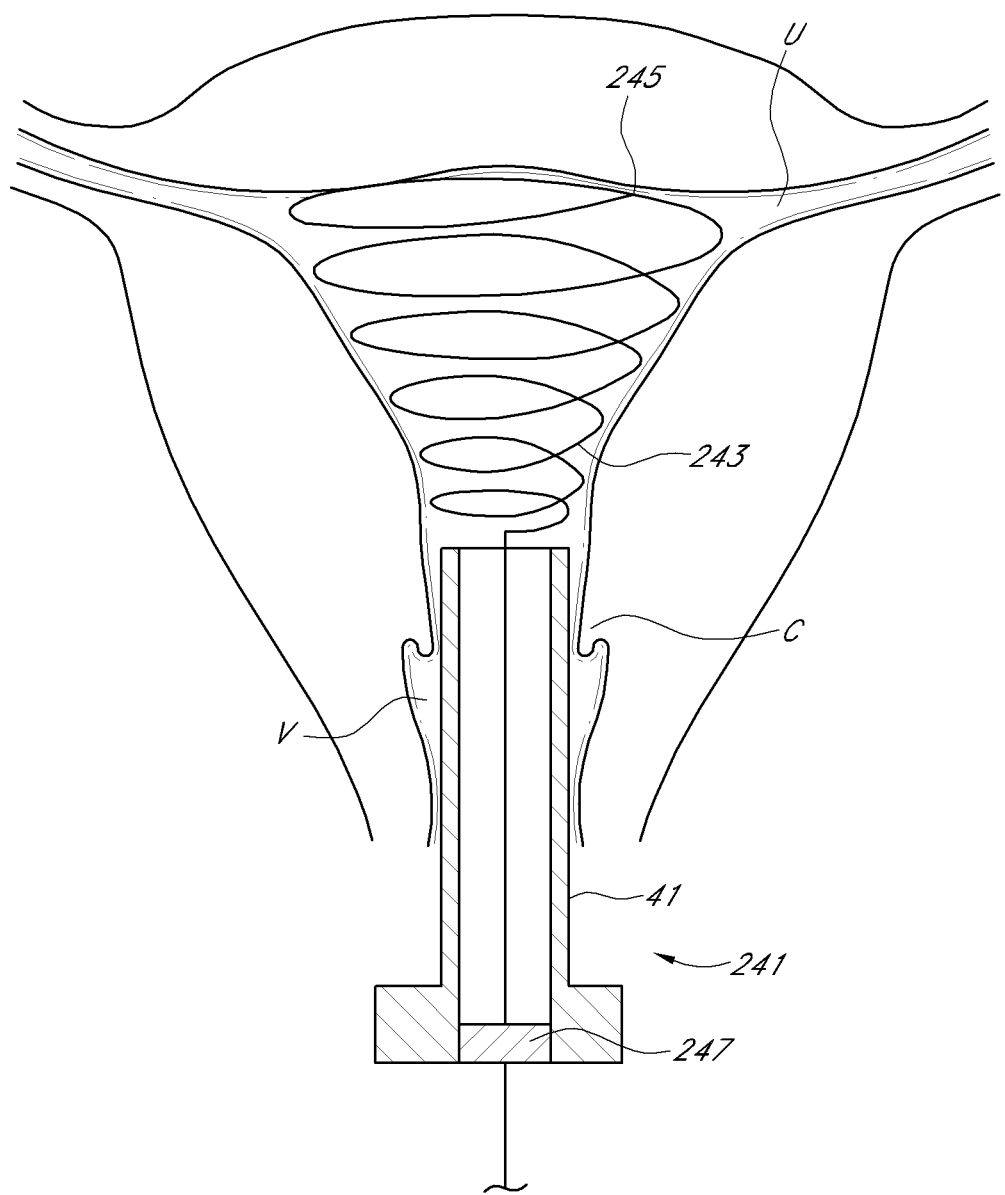
FIG. 8 is a top view, partly in section, of still yet another device for distending a gynecological cavity, the device being constructed according to the teachings of the present invention and being shown in an expanded state within a uterus.

Referring now to FIG. 8, there is shown a top view of still yet another embodiment of a device for distending a gynecological cavity, the device being constructed according to the teachings of the present invention and being represented generally by reference numeral 241.

Device 241, which is shown in an expanded state within a uterus, is similar in certain respects to device 11. One difference between the two devices is that, whereas device 11 comprises basket 21 and shaft 31, device 241 instead comprises a self-expanding wire 243. Wire 243 is appropriately constructed so that, when pushed distally through sheath 41 or a similar introducer device, it adopts a spiral shape that may mimic the shape of the uterus or other gynecological cavity. Preferably, wire 243 is constructed to distend the uterus to an extent equivalent to that which would be attained using the above-described conventional fluid distension technique at a pressure of at least 40 mm Hg but not greater than 100 mm Hg and preferably at a pressure of approximately 70 mm Hg. A ball 245 or similar structure may be provided on the distal end of wire 243 to prevent perforating tissue within the cavity. A Touhy Borst valve 247 or similar structure may be positioned at the proximal end of sheath 41 to maintain wire 243 at a desired longitudinal position relative to sheath 41.

Figure 9B:
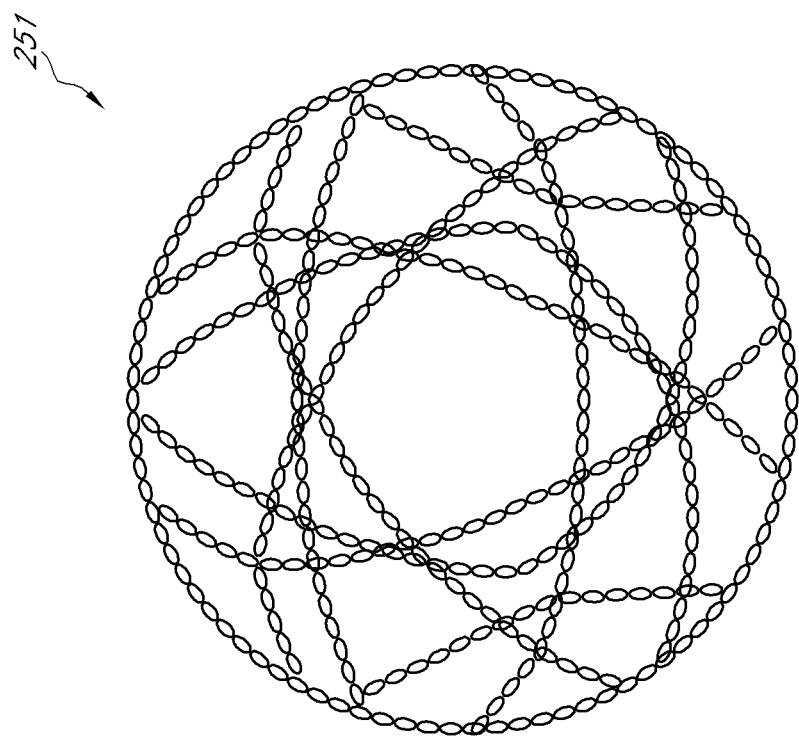
FIGS. 9(a) and 9(b) are top views of still yet another device for distending a gynecological cavity, the device being constructed according to the teachings of the present invention and being shown in a compressed state and in an expanded state, respectively.
Figure 9A:
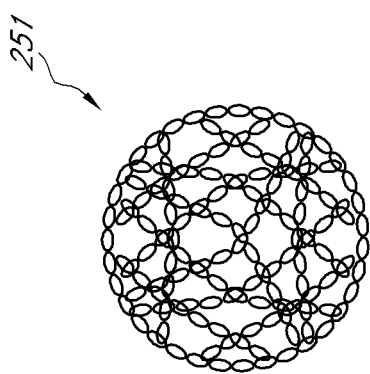

Referring now to FIGS. 9(a) and 9(b), there are shown top views of still yet another embodiment of a device for distending a gynecological cavity, the device being constructed according to the teachings of the present invention and being represented generally by reference numeral 251.

Device 251, which is shown in a compressed state in FIG. 9(a) and in an expanded state in FIG. 9(b), is a self-expanding structure in the form of a Hoberman sphere (icosidodecahedron). Device 251 is appropriately dimensioned so that, in a compressed state, it may be passed through the vagina and the cervix of a patient and, in its expanded state, it may distend the uterus of a patient to a desired extent. Preferably, device 251 is constructed to distend the uterus to an extent equivalent to that which would be attained using the above-described conventional fluid distension technique at a pressure of at least 40 mm Hg but not greater than 100 mm Hg and preferably at a pressure of approximately 70 mm Hg.

Figure 10A:
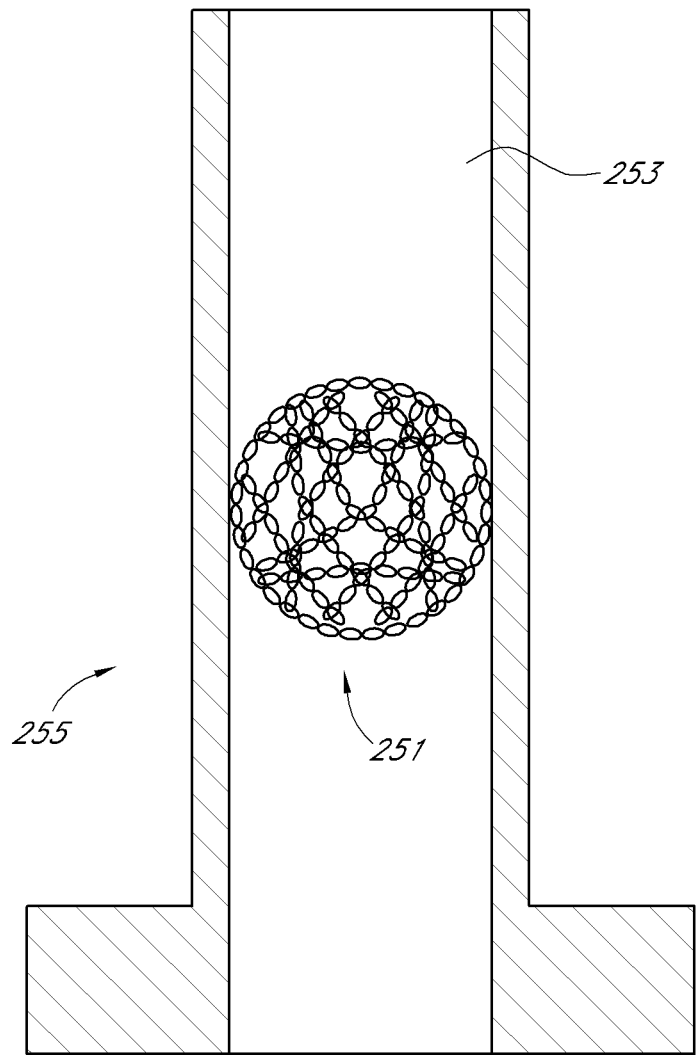
FIGS. 10(a) through 10(e) are schematic top views, partly in section, showing one way in which the device of FIGS. 9(a) and 9(b) may be used to distend a gynecological cavity, such as a uterine cavity.
Figure 10B:
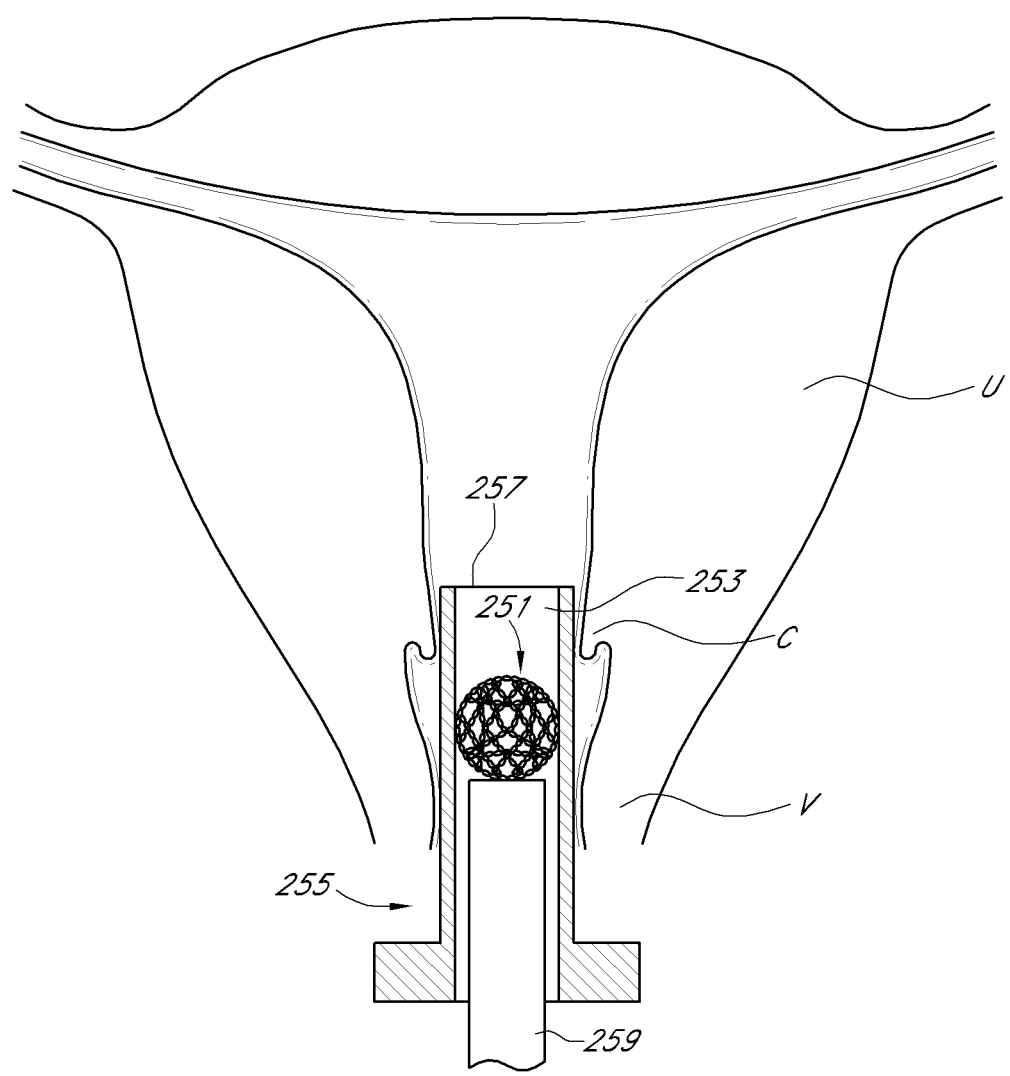
Figure 10C:
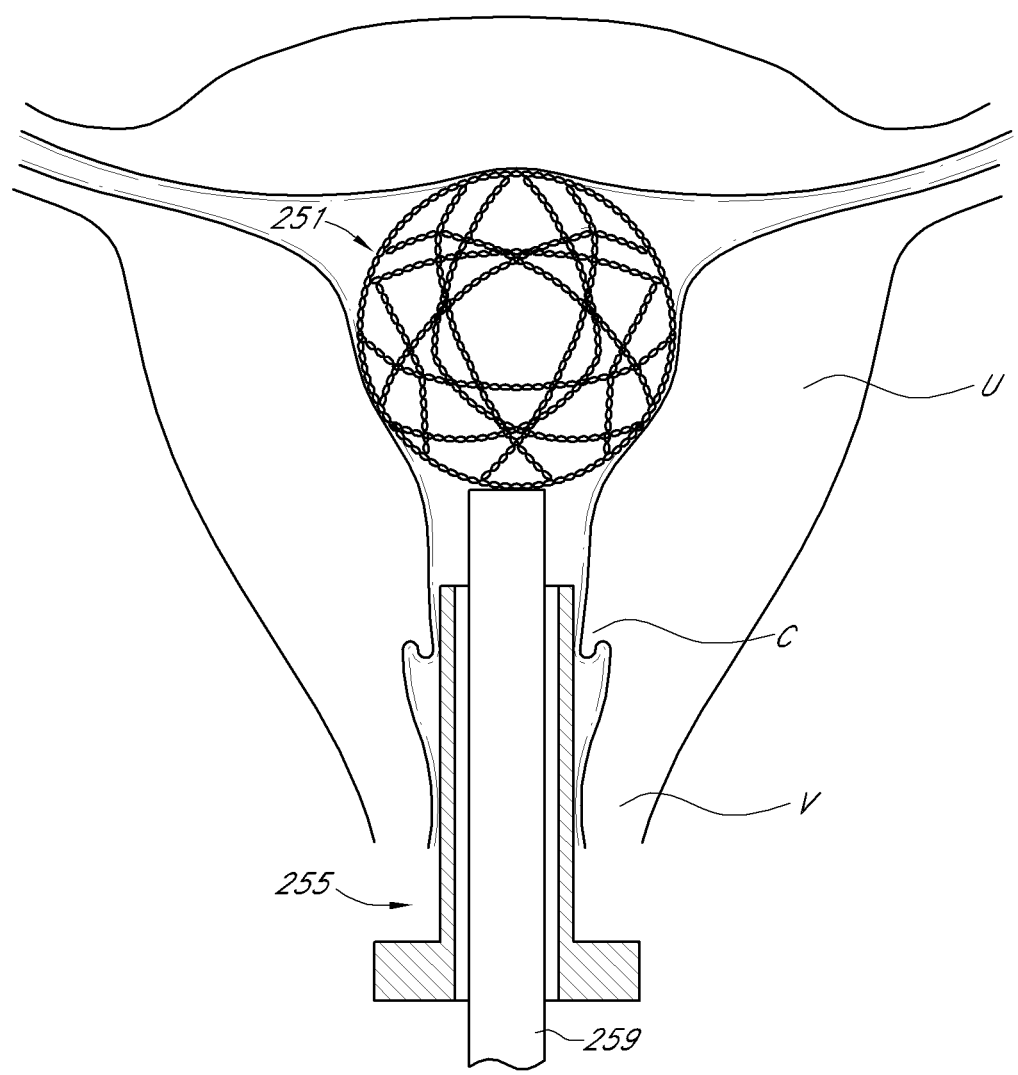
Figure 10D:
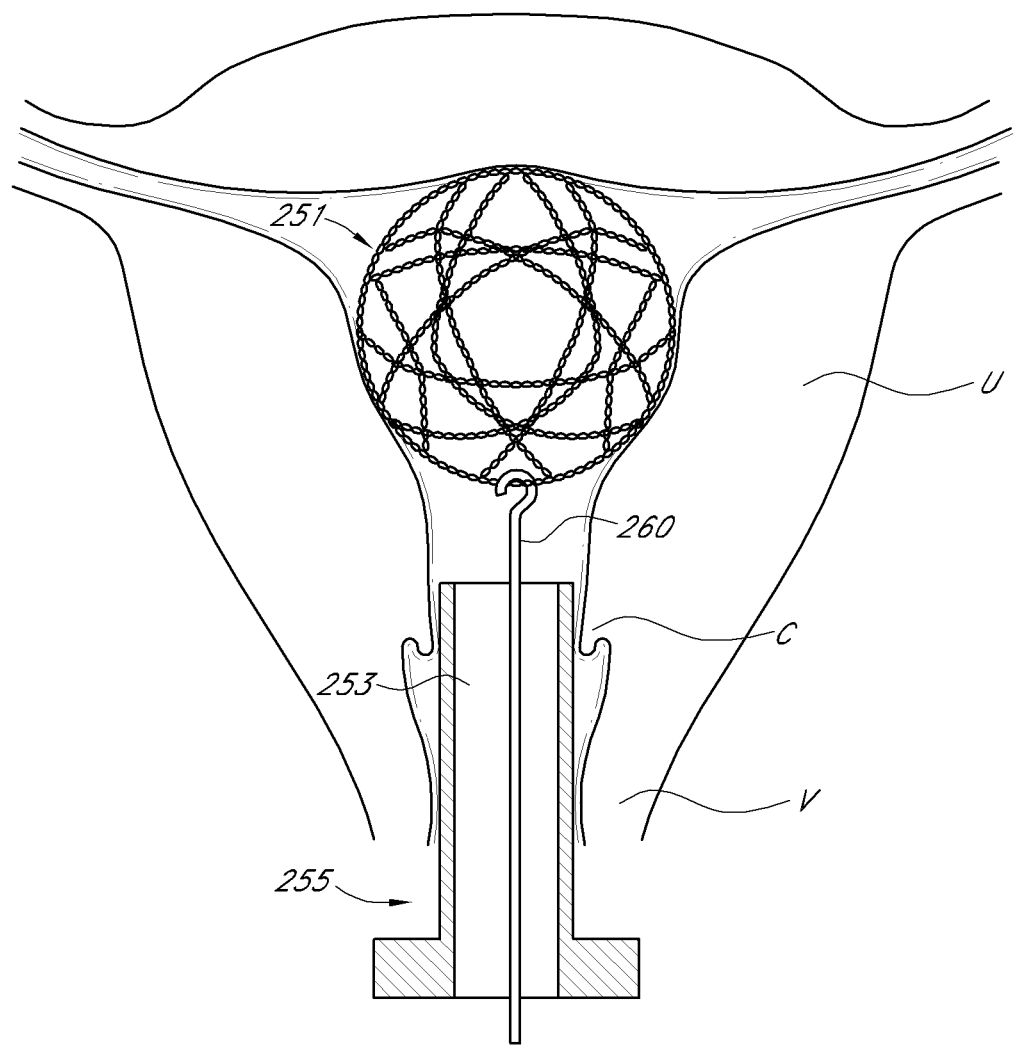
Figure 10E:
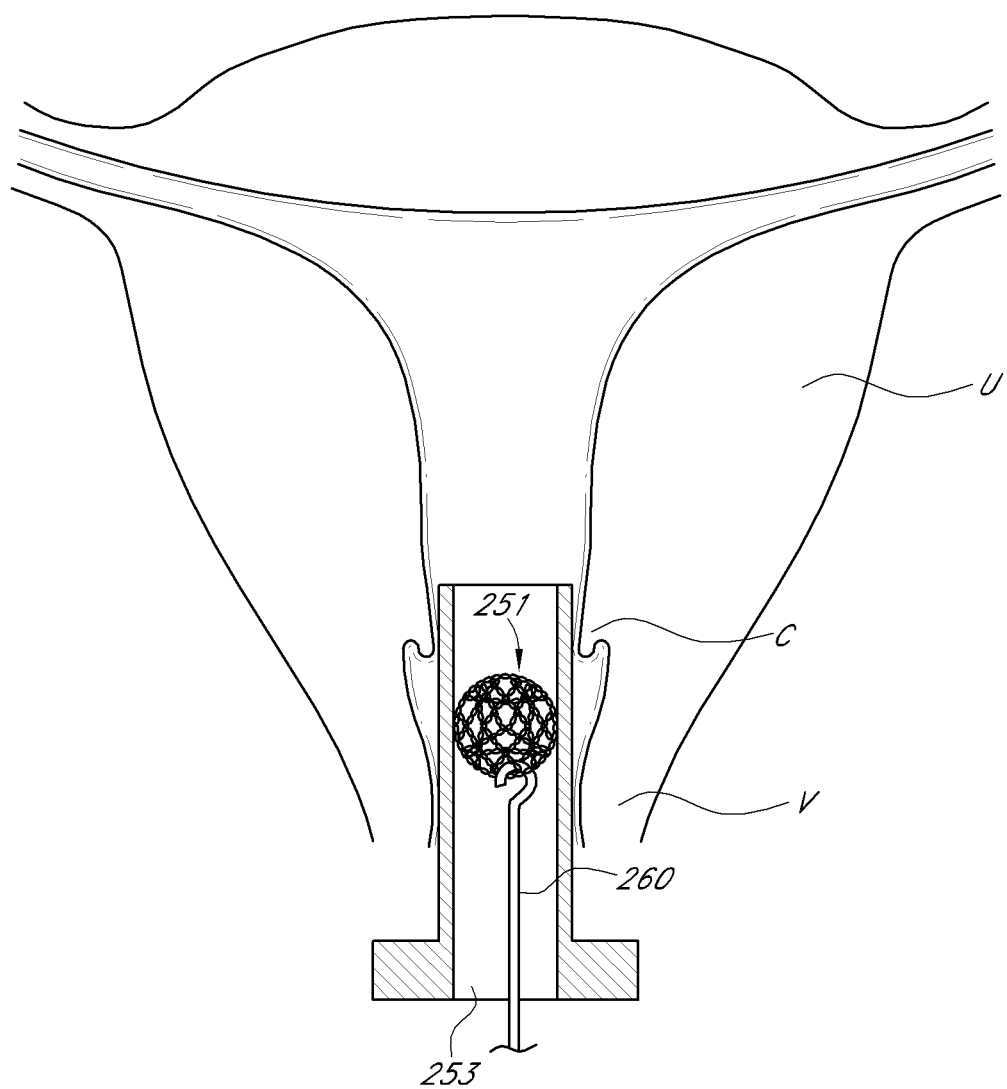

Referring now to FIGS. 10(a) through 10(e), there is shown a series of top views, illustrating one way in which device 251 may be used to distend a gynecological cavity, in particular, a uterine cavity. First, as seen in FIG. 10(a), device 251 is loaded into a lumen 253 of a sheath 255 or other suitable gynecological introducer device, lumen 253 being appropriately dimensioned to maintain device 251 in a compressed state. Next, as seen in FIG. 10(b), with device 251 thus loaded in sheath 255, the distal end 257 of sheath 255 is inserted through the vagina V and the cervix C of a patient, and an ejector rod 259 is inserted distally into lumen 253 to move device 251 distally through lumen 253. Next, as seen in FIG. 10(c), ejector rod 259 ejects device 251 from lumen 253 into uterus U, where device 251 immediately self-expands to its expanded state and distends uterus U. With device 251 now in place distending uterus U, sheath 255 and ejector rod 259 may be removed from the patient. Next, as seen in FIG. 10(d), when distension of uterus U is no longer desired, sheath 255 may be re-introduced into the patient through the vagina and the cervix, and a snare 260 may be distally inserted through lumen 253 to grab device 251. Next, as seen in FIG. 10(e), snare 260 and device 251 are then withdrawn proximally through lumen 253, device 251 being compressed by lumen 253.

In another embodiment (not shown), device 251 could be modified to include a tie-line or the like having a first end secured to device 251 and a second end remaining external to the patient. In this manner, instead of using a snare to pull device 251 through lumen 253, one could simply pull proximally on tie-line to pull device 251 through lumen 253.

Figure 11B:
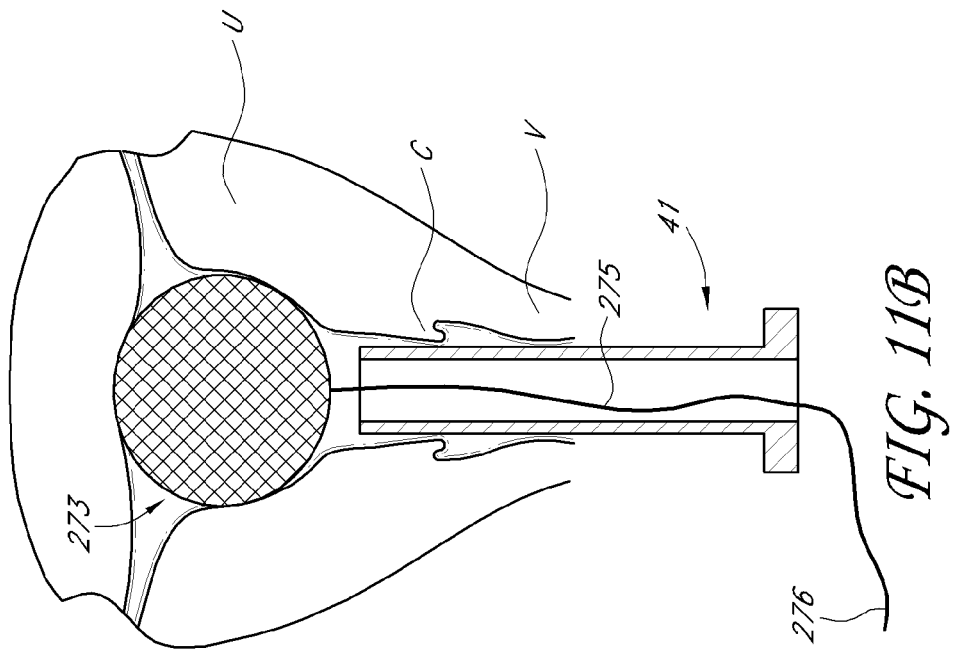
FIGS. 11(a) and 11(b) are top views, partly in section, of still yet another embodiment of a device for distending a gynecological cavity, the device being constructed according to the teachings of the present invention and being shown within a uterus in a compressed state and in an expanded state, respectively.
Figure 11A:
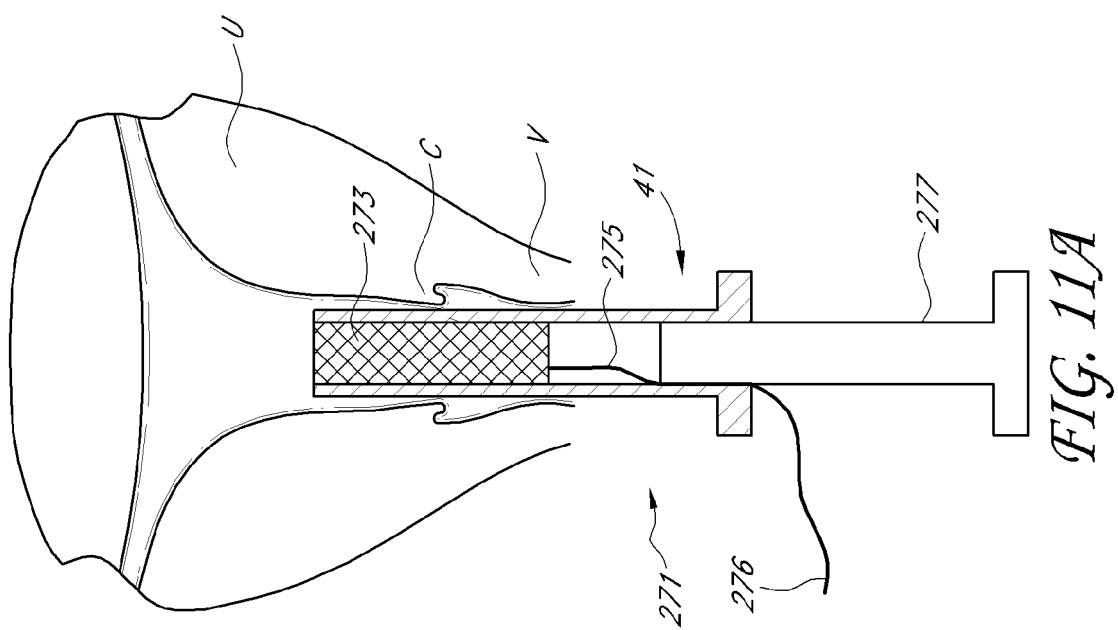

Referring now to FIGS. 11(a) and 11(b), there are shown top views, partly in section, of still yet another embodiment of a device for distending a gynecological cavity, the device being constructed according to the teachings of the present invention and being represented generally by reference numeral 271.

Device 271 is similar in many respects to device 11. One difference between the two devices is that, whereas device 11 includes a basket 21 fixed to distal end 33 of shaft 31, device 271 instead includes a self-expanding basket 273, a tie-line 275 having a proximal end 276 preferably extending proximally from sheath 41 and a distal end fixed to basket 273, and an ejector rod 277 slidably and removably mounted within sheath 41 for ejecting basket 273 distally from sheath 41.

In use, basket 273 may be loaded into sheath 41 or a similar introducer device, with proximal end 276 of line 275 preferably extending proximally from sheath 41. The distal end of the thus-loaded sheath may then be inserted through the vagina V and the cervix C of a patient. Ejector rod 277 may then be inserted distally into sheath 41 until basket 273 is ejected from sheath 41 into the uterus U of the patient, at which time basket 273 self-expands to distend the uterus. Preferably, proximal end 276 of line 275 is held in place while ejector rod is inserted into sheath 41 to ensure that end 276 remains external to sheath 41. With basket 273 thus deployed, ejector rod 277 may then be removed proximally from sheath 41. To remove basket 273 from the uterus U, one may pull line 275 proximally until basket 273 is drawn into sheath 41. Basket 273 and sheath 41 may then be removed from the patient.

As can be appreciated, device 271 may be modified to replace basket 273 with other self-expanding structures that may be compressed and withdrawn from a gynecological cavity by being pulled into sheath 41 or a similar introducer device.

Figures 12A, 12B:
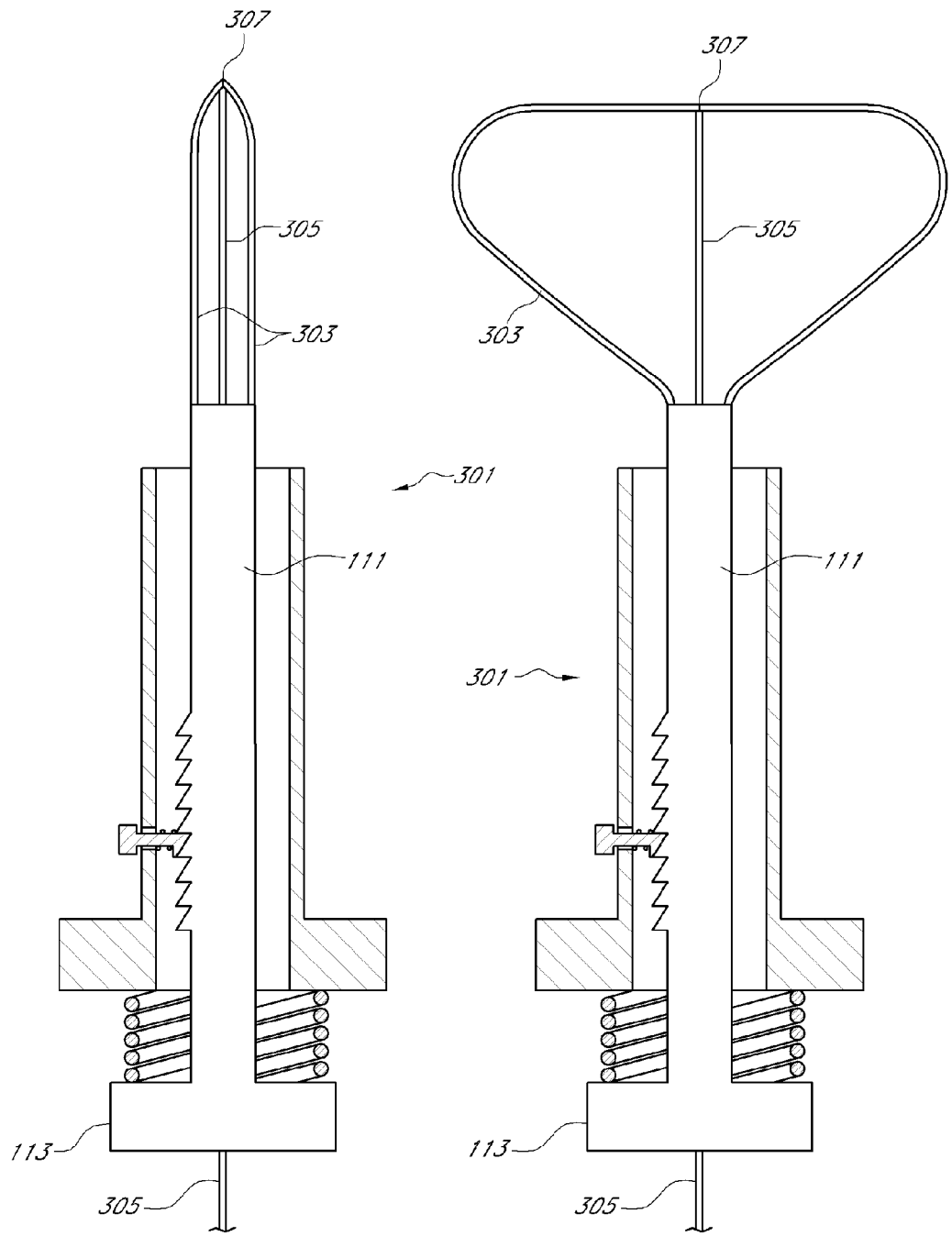
FIGS. 12(a) and 12(b) are top views, partly in section, of still yet another embodiment of a device for distending a gynecological cavity, the device being constructed according to the teachings of the present invention and being shown in a non-expanded state and in an expanded state, respectively.

Although all of the distension devices described above include self-expanding, expandable means, the present invention is not limited to expandable means that are self-expanding and may alternatively include expandable means that are not self-expanding, but rather, are expanded by some other means. An example of such a device is shown in FIGS. 12(a) and 12(b) and is represented generally by reference numeral 301.

Device 301 is similar in many respects to device 151, the principal difference between the two devices being that, whereas device 151 includes a self-expanding loop 153, device 301 includes (i) a mechanically-expandable loop 303 and (ii) a tensioning wire 305. Tensioning wire 305 is fixed at one end to the distal end 307 of loop 303. The opposite end of tensioning wire 305 is passed through a lumen (not shown) in shaft 111 and terminates proximally beyond proximal end 113 of shaft 111.

Device 301 may be used in a fashion similar to that for device 151, the only difference being that, after loop 303 has been inserted into the uterus or other gynecological cavity, loop 303 must be actively expanded by pulling proximally on tensioning wire 305. (Although not shown, device 301 may include a hook or similar structure around which the proximal end of tensioning wire 305 may be wrapped or otherwise fixed in order to maintain a constant amount of tension on wire 305.) Preferably, when loop 303 is expanded, loop 303 distends the uterus to an extent equivalent to that which would be attained using the above-described conventional fluid distension technique at a pressure of at least 40 mm Hg but not greater than 100 mm Hg and preferably at a pressure of approximately 70 mm Hg. When distension of the gynecological cavity is no longer desired, tensioning wire 305 may be moved distally to its original position, thereby restoring loop 303 to its non-expanded state.

One notable attribute of device 301 is that the distending pressure exerted by device 301 may be varied by varying the amount of tension applied to tensioning wire 305.

Figure 13A:
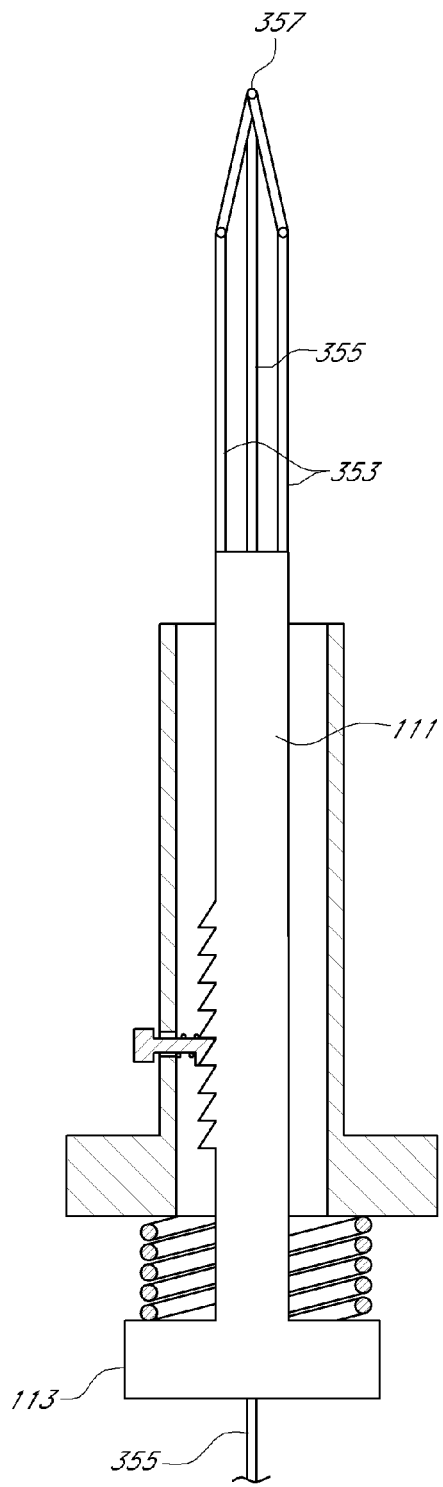
FIGS. 13(a) and 13(b) are top views, partly in section, of still yet another embodiment of a device for distending a gynecological cavity, the device being constructed according to the teachings of the present invention and being shown in a non-expanded state and in an expanded state, respectively.
Figure 13B:
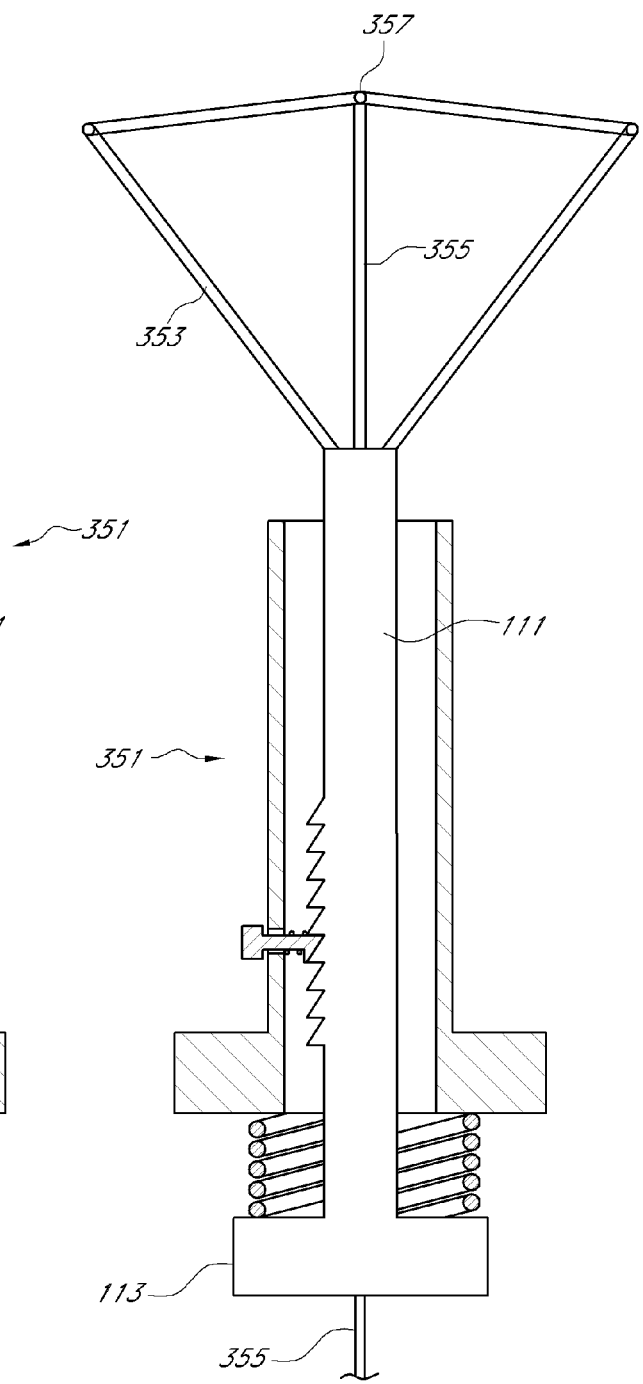

Another example of a device having expandable means that are not self-expanding is shown in FIGS. 13(a) and 13(b) and is represented generally by reference numeral 351.

Device 351 is similar in many respects to device 181, the principal difference between the two devices being that, whereas device 181 includes self-expanding cage 183, device 351 includes (i) a mechanically-expandable cage 353 and (ii) a tensioning wire 355. Tensioning wire 355 is fixed at one end to the distal end 357 of cage 353. The opposite end of tensioning wire 355 is passed through a lumen (not shown) in shaft 111 and terminates proximally beyond proximal end 113 of shaft 111.

Device 351 may be used in a fashion similar to that for device 181, the only difference being that, after cage 353 has been inserted into the uterus or other gynecological cavity, cage 353 must be actively expanded by pulling proximally on tensioning wire 355. (Although not shown, device 351 may include a hook or similar structure around which the proximal end of tensioning wire 355 may be wrapped or otherwise fixed in order to maintain a constant amount of tension on wire 355.) Preferably, when cage 353 is expanded, cage 353 distends the uterus to an extent equivalent to that which would be attained using the above-described conventional fluid distension technique at a pressure of at least 40 mm Hg but not greater than 100 mm Hg and preferably at a pressure of approximately 70 mm Hg. When distension of the gynecological cavity is no longer desired, tensioning wire 355 may be moved distally to its original position, thereby restoring cage 353 to its non-expanded state.

In a manner similar to that described above in connection with device 301, device 351 may be used to exert a variable distending pressure by varying the amount of tension applied to tensioning wire 355.

Figure 14:
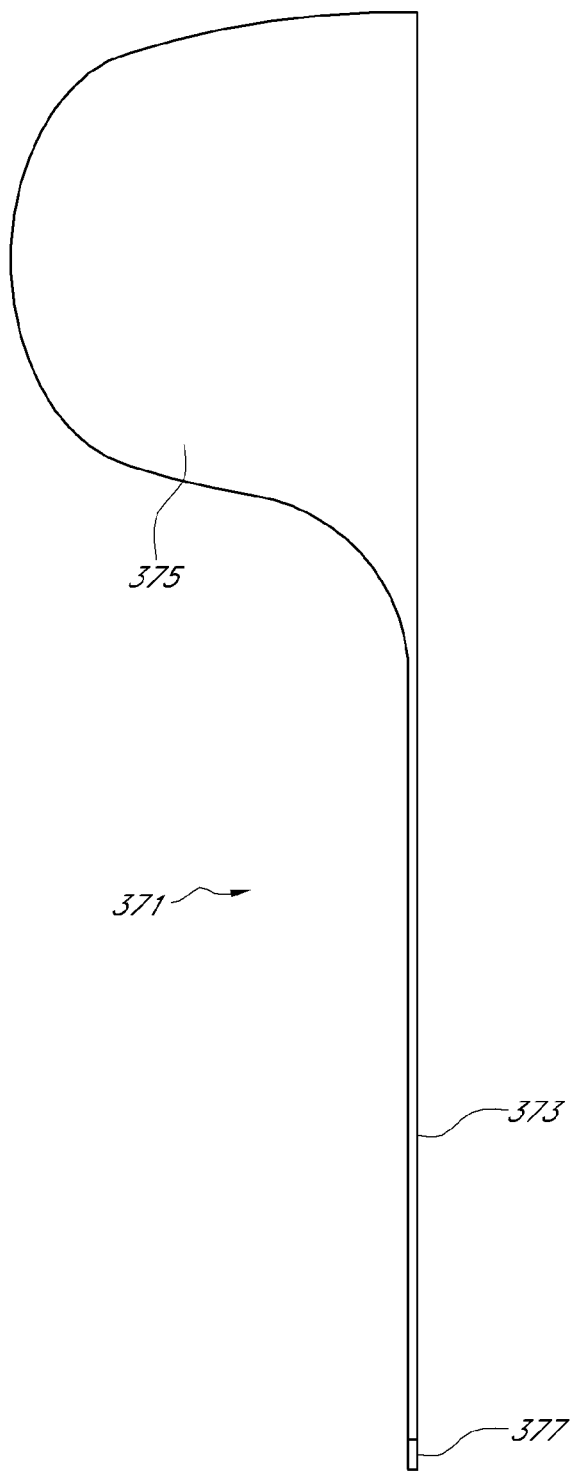
FIG. 14 is a top view of still yet another embodiment of a device for distending a gynecological cavity, the device being constructed according to the teachings of the present invention and being shown in an expanded state.

Referring now to FIG. 14, there is shown a top view of still yet another embodiment of a device for distending a gynecological cavity, the device being constructed according to the teachings of the present invention and being represented generally by reference numeral 371.

Device 371 may comprise a proximal inflation line 373 and a distal balloon portion 375, line 373 and balloon portion 375 being in fluid communication with one another. An inflation valve 377 may be disposed at the proximal end of inflation line 373. In the present embodiment, balloon portion 375 has an asymmetric- or lobed-shape to distend approximately one-half of a uterus or similar gynecological cavity. In this manner, balloon portion 375 may occupy a portion of a uterus while the remaining, unoccupied portion may be left accessible for observation, diagnosis and/or treatment. Balloon portion 375 may be either compliant or non-compliant.

Figures 15A, 15B:
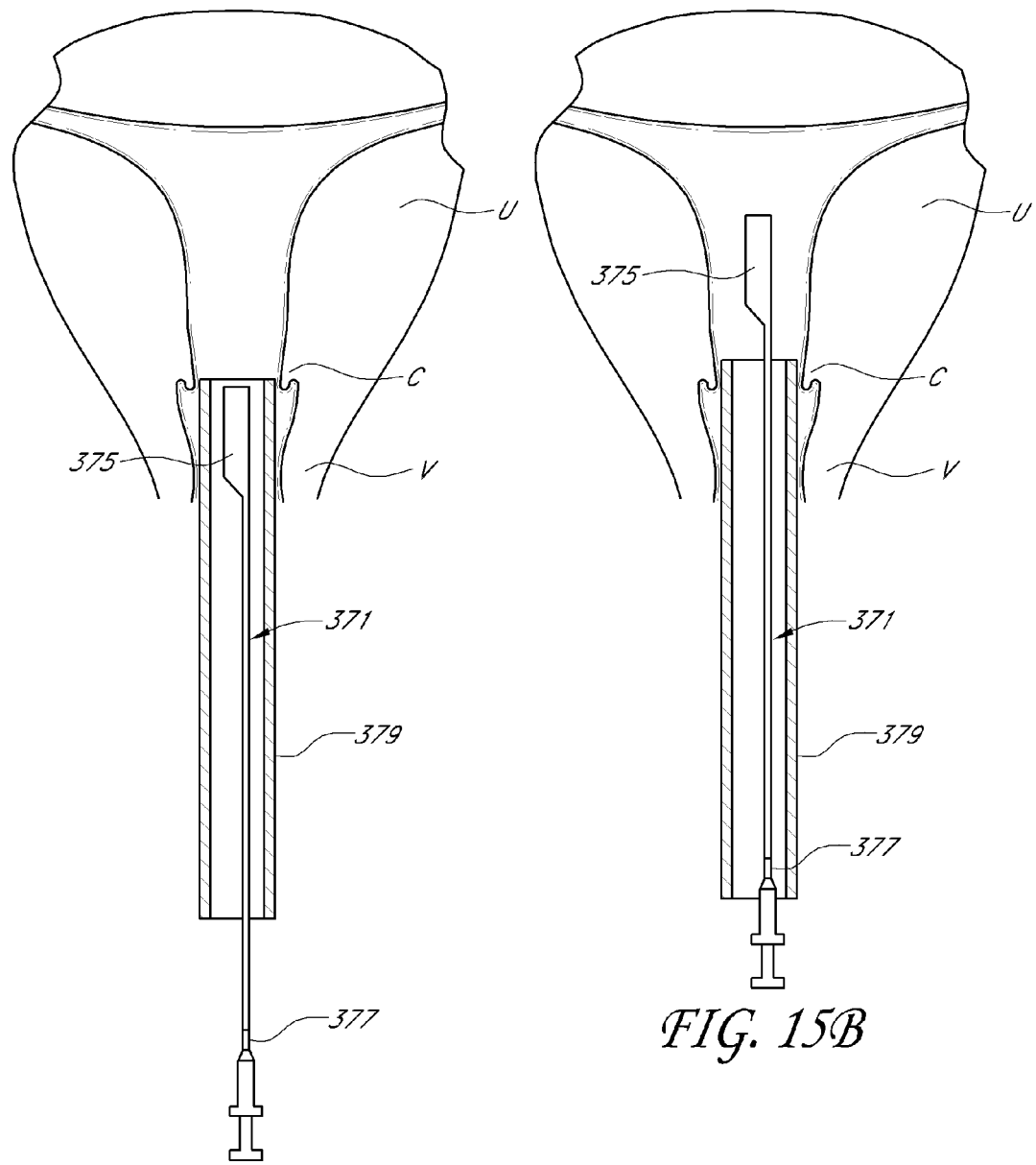
FIGS. 15(a) through 15(e) are schematic top views, partly in section, showing one way in which the device of FIG. 14 may be used to distend a gynecological cavity, such as a uterine cavity.
Figures 15C, 15D:
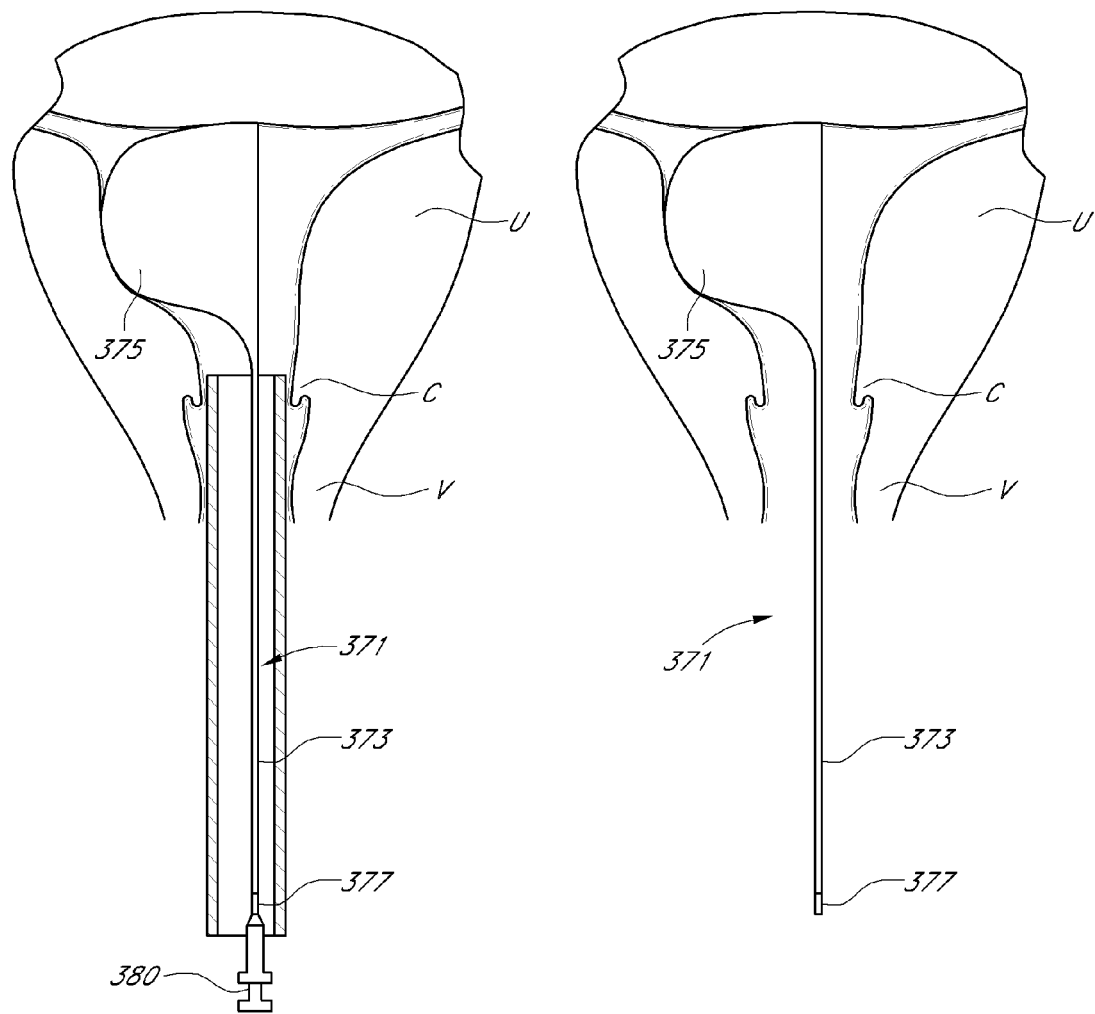
Figure 15E:
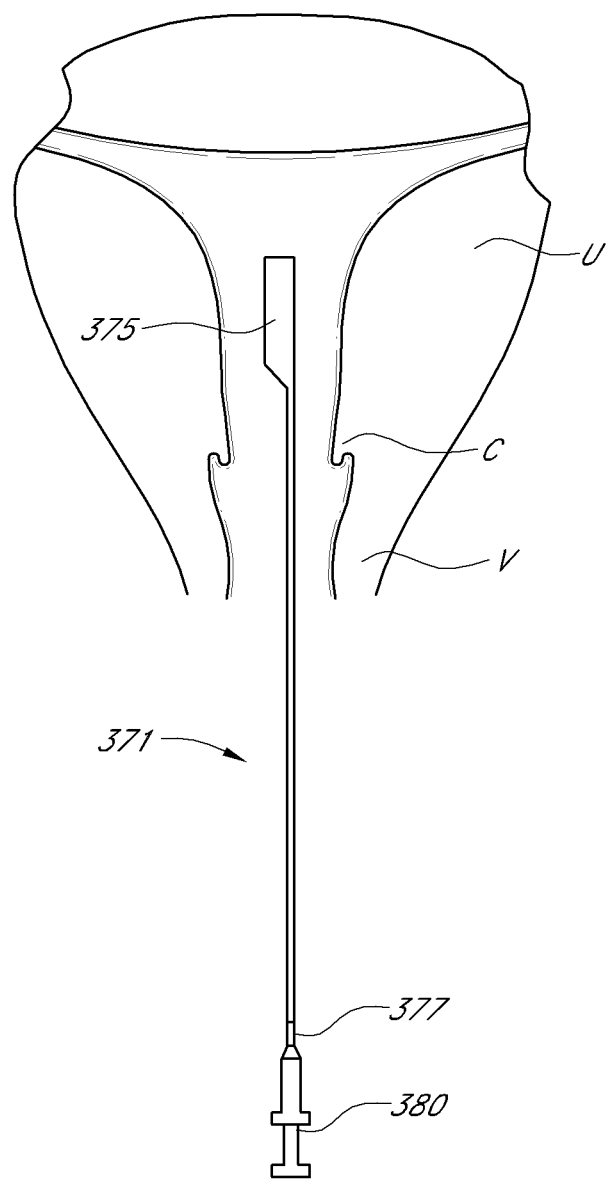

Referring now to FIGS. 15(a) through 15(e), there is schematically shown one way in which device 371 may be used. First, as seen in FIG. 15(a), with balloon portion 375 deflated, the distal end of device 371 may be inserted through the vagina V and the cervix C of the patient through a sheath 379 or similar introducer device. Next, as seen in FIG. 15(b), device 371 may be moved distally relative to sheath 379 so that balloon portion 375 may be positioned within the uterus U. Next, as seen in FIG. 15(c), fluid may be dispensed from syringe 380 through line 373 and into balloon portion 375, thereby causing balloon portion 375 to become inflated and the uterus U to become distended. The fluid dispensed from syringe 380 may be, for example, a gas, such as carbon dioxide, or a liquid, such as a saline solution. Next, as seen in FIG. 15(d), with balloon portion 375 fully inflated, syringe 380 may be removed from device 371. Next, as seen in FIG. 15(e), when distension of the uterus U is no longer desired, syringe 380 may be reattached to device 371 and balloon portion 375 deflated. Device 371 may then be withdrawn from the patient.

Figure 16A:
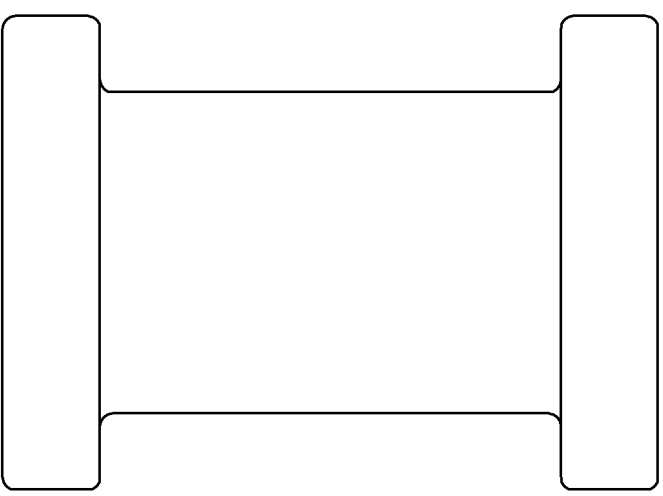
FIGS. 16(a) and 16(b) are fragmentary top and rear views, respectively, of an alternate embodiment to the device shown in FIG. 14, the alternate embodiment being constructed according to the teachings of the present invention and being shown in its expanded state.
Figure 16B:
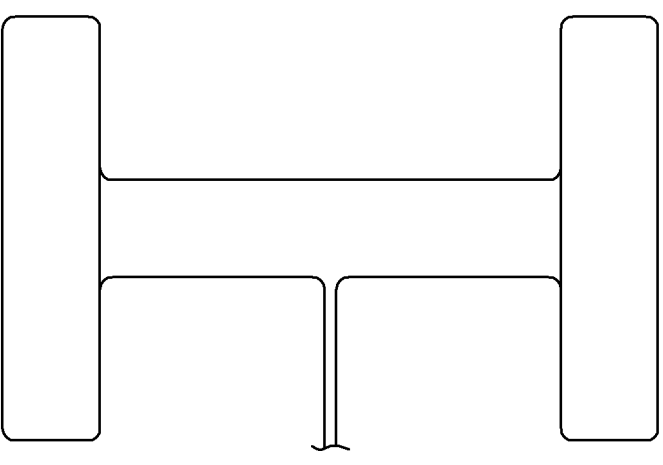

Referring now to FIGS. 16(a) and 16(b), there are shown fragmentary top and rear views, respectively, of an alternate balloon portion to the balloon portion 375 of device 371, the alternate balloon portion being represented by reference numeral 401. As can be seen best in FIG. 16(a), balloon portion 401 has an I-shape and, therefore, may be well-suited for contacting opposing walls of a uterus or similar gynecological cavity in such a way as to keep the cavity distended.

Figure 17A:
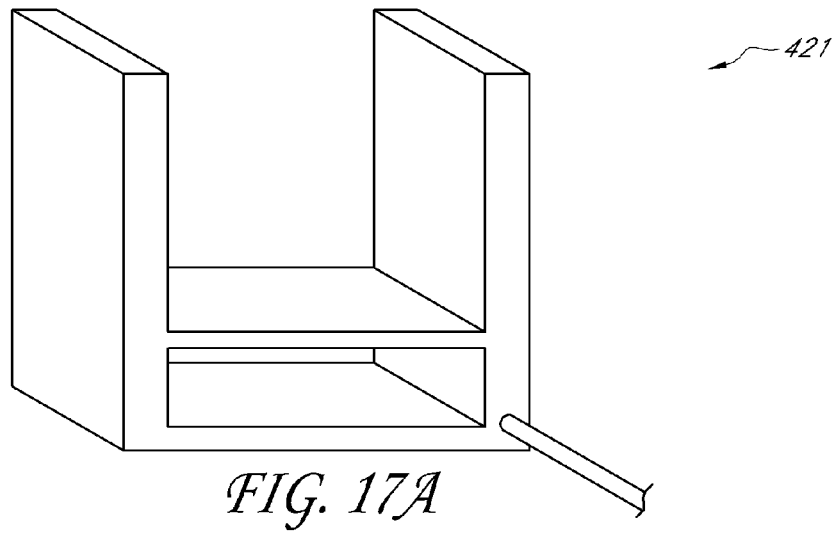
FIGS. 17(a) through 17(c) are perspective views of additional alternate embodiments to the device shown in FIG. 14, the alternate embodiments being constructed according to the teachings of the present invention and being shown in their respective expanded states.
Figure 17B:
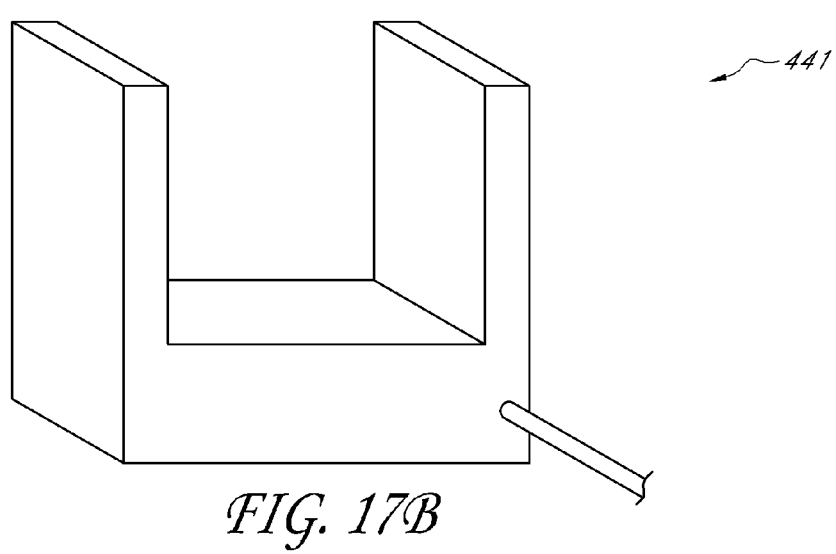
Figure 17C:
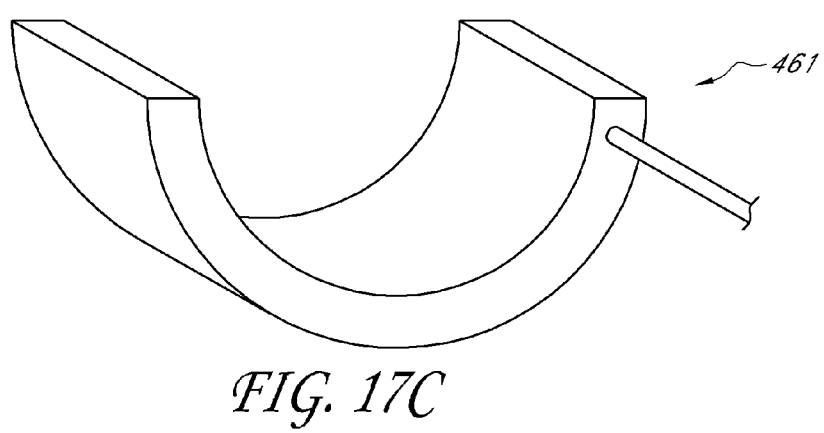

Additional alternate balloon portions are shown in FIGS. 17(a) through 17(c), respectively, and are represented by numerals 421, 441 and 461, respectively. Each of balloon portions 421, 441 and 461 may be dimensioned to contact opposing walls of a uterus or other gynecological cavity in such a way as to keep the cavity distended. Further alternate balloon portions (not shown) may include, for example, annular, annular oval, rectangular, and T-shaped balloon portions.

Referring now to FIGS. 18(a) and 18(b), there are shown section views of still yet another embodiment of a device for distending a gynecological cavity, the device being constructed according to the teachings of the present invention and being represented generally by reference numeral 481.

Device 481 is similar in certain respects to device 371, the principal difference between the two devices being that, whereas device 371 includes a single balloon portion 373, device 481 instead includes two balloon portions 483 and 485. Balloon portion 483 is fluidly connected to an inflation line 487, and balloon portion 485 is fluidly connected to an inflation line 489. Inflation valves 491 and 493 are positioned at the proximal ends of inflation lines 487 and 489, respectively. As can be seen best in FIG. 18(b), because balloon portions 483 and 485 are independently-operable, one may inflate one without inflating the other. Consequently, a desirable attribute of device 481 is that, with a single insertion of device 481 into a patient, one may inflate only one of balloon portions 483 and 485, for example, to create the space necessary to perform a procedure on one side of a gynecological cavity, and then inflate only the other one of balloon portions 483 and 485, for example, to create the space necessary to perform a procedure on the opposite side of the cavity.

Referring now to FIG. 19, there is shown a section view of still yet another embodiment of a device for distending a gynecological cavity, the device being constructed according to the teachings of the present invention and being represented generally by reference numeral 501.

Device 501 is similar in certain respects to device 481, the principal difference between the two devices being that, whereas device 481 includes two independently-operable balloon portions 483 and 485, device 501 includes three independently-operable balloon portions 503, 505 and 507. Balloon portion 503 is fluidly connected to an inflation line 511, balloon portion 505 is fluidly connected to an inflation line 513, and balloon portion 507 is fluidly connected to an inflation line 515. Inflation valves 517, 519 and 521 are positioned at the proximal ends of inflation lines 511, 513 and 515, respectively.

Figures 20A, 20B:
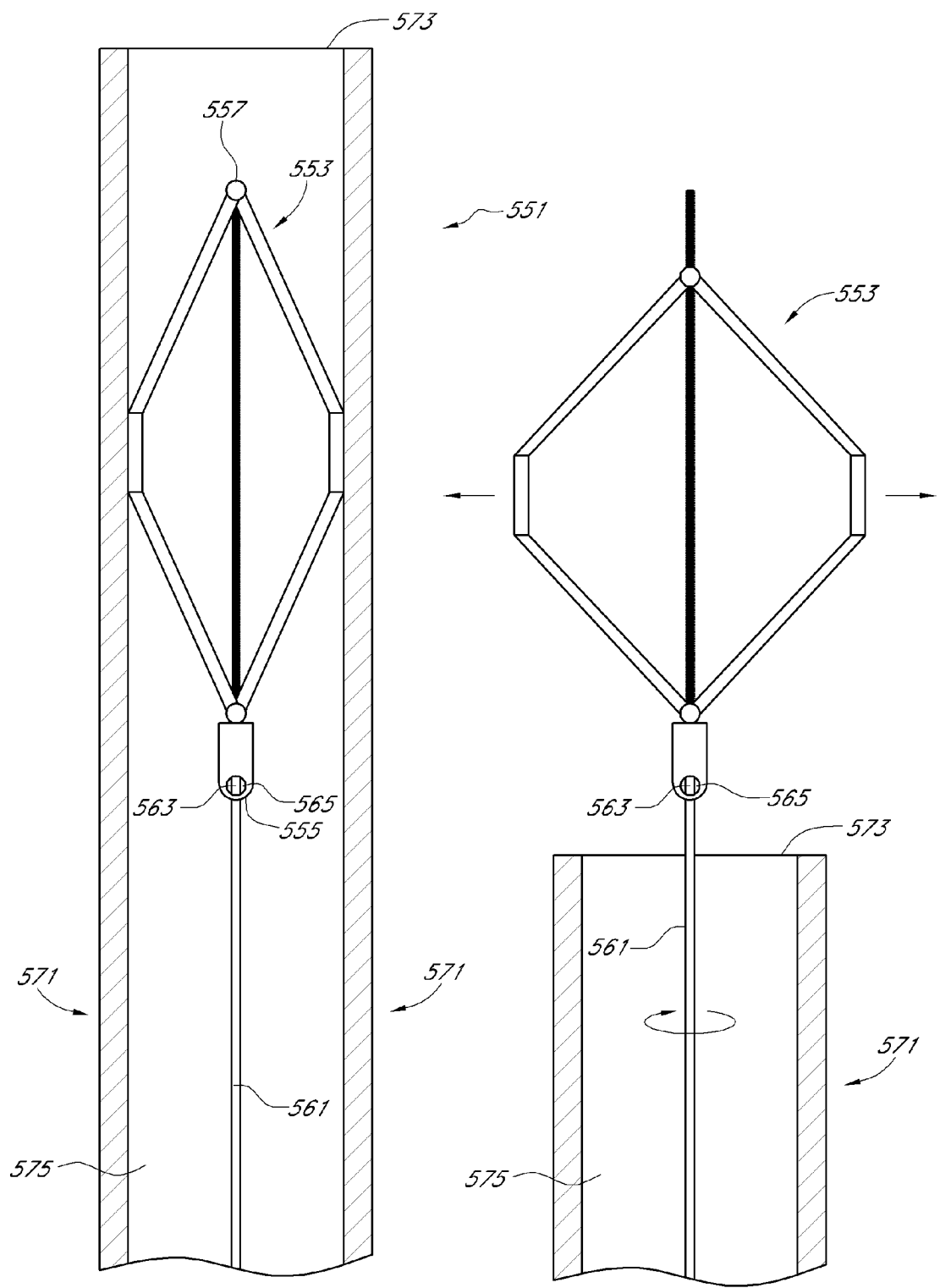
FIGS. 20 (a) and 20(b) are top views, partly in section, of still yet another embodiment of a device for distending a gynecological cavity, the device being constructed according to the teachings of the present invention and being shown in a non-expanded state and in a partially expanded state, respectively.

Referring now to FIGS. 20(a) and 20(b), there are shown top views, partly in section, of still yet another embodiment of a device for distending a gynecological cavity, the device being constructed according to the teachings of the present invention and being represented generally by reference numeral 551.

Device 551 may include a scissor jack 553. Scissor jack 553, which may be conventional in configuration, is preferably dimensioned for use in a gynecological cavity, such as the uterus. Consequently, scissor jack 553 preferably has a maximum length, as measured from proximal end 555 to distal end 557, of about 4-10 cm. In addition, scissor jack 553 is preferably constructed so that, when expanded, jack 553 distends the uterus to an extent equivalent to that which would be attained using the above-described conventional fluid distension technique at a pressure of at least 40 mm Hg but not greater than 100 mm Hg and preferably at a pressure of approximately 70 mm Hg.

Device 551 may additionally include a jack crank 561. Jack crank 561 may have a hook 563 or similar structure at its distal end suitable for mating with a loop 565 at proximal end 555 of jack 553. With crank 561 coupled to jack 553, for example, by inserting hook 563 through loop 565, one may rotate crank 561 about its longitudinal axis to cause jack 553 to expand laterally.

Device 551 may further include a delivery sheath 571. Sheath 571, which may be a unitary tubular member, may be shaped to include a proximal end (not shown), a distal end 573, and a longitudinal lumen 575. Lumen 575 may be dimensioned to permit jack 553 to be passed therethrough, particularly with jack 553 is in its non-expanded state. Distal end 573 may be adapted to be inserted into the uterus transcervically, with the proximal end of sheath 571 remaining external to the patient. To minimize discomfort to the patient, such as by obviating the need for administration of an anesthetic to the patient, the outer diameter of that portion of sheath 571 inserted into the patient is preferably less than about 5.5 mm.

In use, crank 561 may be coupled to jack 553, and jack 553 may then be inserted distally into lumen 575 of sheath 571. Distal end 573 of sheath 571 may then be inserted through the vagina and the cervix of the patient. Next, jack 553 may be moved distally through distal end 573 of sheath 571 and into the uterus of the patient. Next, crank 561 may be rotated about its longitudinal axis, thereby causing jack 553 to expand laterally. Preferably, crank 561 is rotated until jack 553 engages opposing walls of the uterus and distends the uterus to a desired extent. Next, crank 561 may be decoupled from jack 553 and removed proximally from the patient. When, distension of the uterus is no longer desired, one may re-insert crank 561 through shaft 571, re-attach crank 561 to jack 553, and rotate crank 561 in the opposite direction to return jack 553 to its non-expanded state. Thus returned to its non-expanded state, jack 553 and crank 561 may then be withdrawn proximally from the patient through sheath 571.

Although jack 553 and crank 561 may be coupled together in the present embodiment by means of a hook and loop mechanism, jack 553 and crank 561 may be coupled together by other means, such as by magnets.

Figure 21:
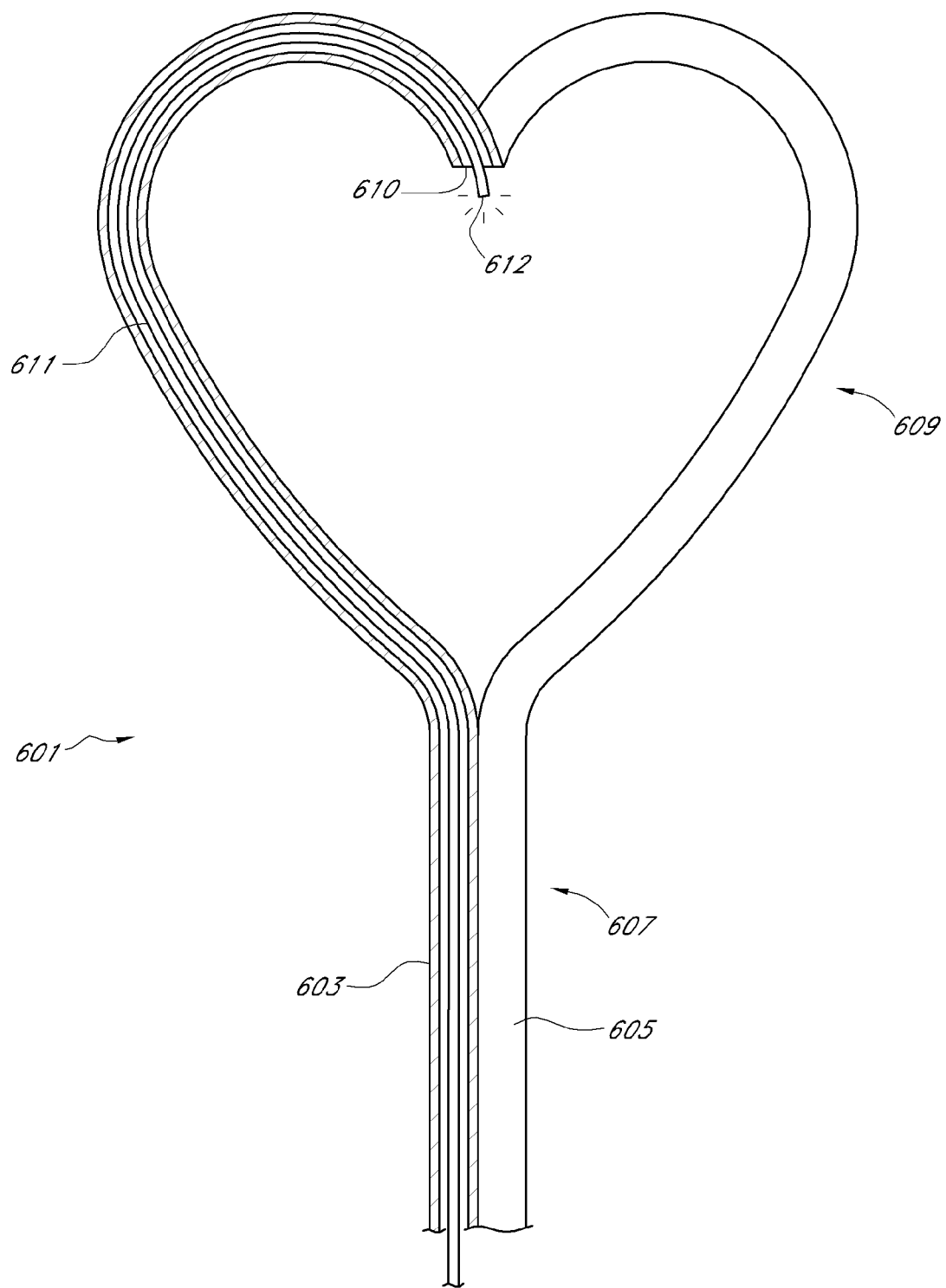
FIG. 21 is a top view, partly in section, of still yet another embodiment of a device for distending a gynecological cavity, the device being constructed according to the teachings of the present invention and being shown in an expanded state with visualization means associated therewith.

In addition to being used to distend the gynecological cavity of a patient, the distension device of the present invention may be designed to perform one or more additional functions. An example of such a multi-purpose device is shown in FIG. 21 and is represented by reference numeral 601.

Device 601, which may be used both to distend a gynecological cavity and to permit observation of the inside of the gynecological cavity, may include elongated, resilient members 603 and 605. Members 603 and 605 may be arranged relative to one another so that their respective proximal portions form a unified shaft 607 and so that their respective distal portions form expandable means. In the present embodiment, said expandable means comprises a self-expanding heart-shaped structure 609. Preferably, when structure 609 expands, structure 609 distends the uterus or other gynecological cavity to an extent equivalent to that which would be attained using the above-described conventional fluid distension technique at a pressure of at least 40 mm Hg but not greater than 100 mm Hg and preferably at a pressure of approximately 70 mm Hg.

Member 603 is a tubular structure having an open proximal end (not shown) and an open distal end 610. In this manner, the distal end 612 of fiber optics 611 may be passed through member 603 and into the gynecological cavity to permit illumination and/or observation of the cavity.

In use, the distal end of device 601 may be inserted into a gynecological cavity, such as a uterus, using an appropriately dimensioned introducer device. (The proximal end of device 601 preferably remains external to the patient.) While positioned within the introducer device, structure 609 is compressed to a small profile. However, once structure 609 passes completely through the introducer device, structure 609 self-expands to its expanded state, where it distends the gynecological cavity. The distal end 612 of fiber optics 611 may then be passed through member 603 and into the distended cavity. (The proximal end of optics 611 preferably remains external to the patient.) When observation of the distended cavity is no longer desired, fiber optics 611 may be withdrawn proximally from member 603. When distension of the cavity is no longer desired, device 601 may be removed from the patient by withdrawing structure 609 through the introducer device, the introducer device serving to compress structure 609.

One desirable attribute of device 601 is that it may be used to visualize the uterus from the vantage point of the uterine fundus, as opposed to the cervical-uterine junction, which would be the case if one merely inserted the fiber optics into the uterus through an introducer device.

Figure 22:
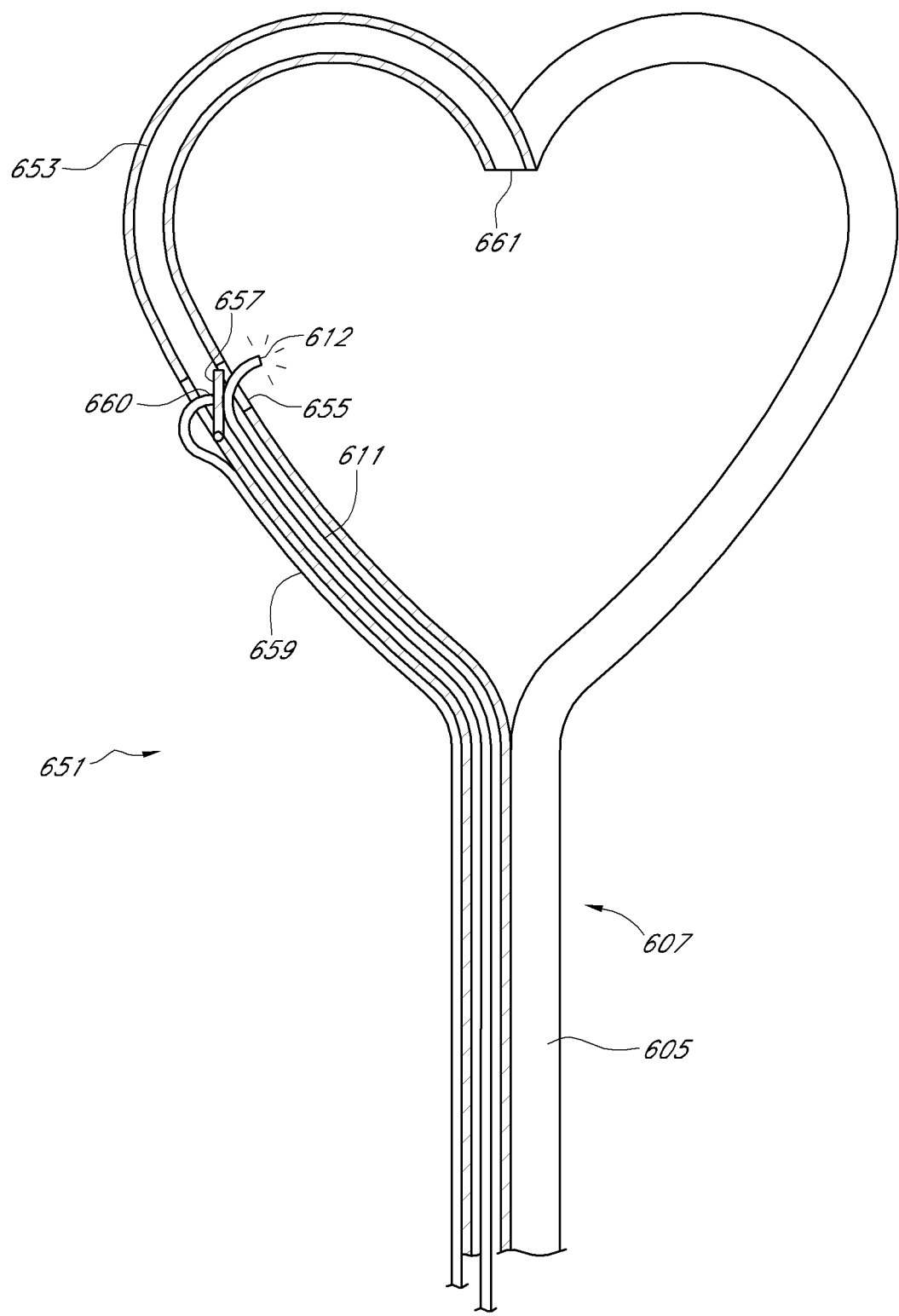
FIG. 22 is a top view, partly in section, of still yet another embodiment of a device for distending a gynecological cavity, the device being constructed according to the teachings of the present invention and being shown in an expanded state with visualization means associated therewith.

Referring now to FIG. 22, there is shown a top view, partly in section, of another embodiment of a multi-purpose device, the multi-purpose device being constructed according to the teachings of the present invention and being represented by reference numeral 651.

Device 651 is similar in most respects to device 601. However, one difference between the two devices is that device 651 may include an elongated, resilient member 653, instead of elongated, resilient member 603. Member 653 differs principally from member 603 in that member 653 may additionally include (i) an inwardly-facing, transverse opening 655 at an intermediate location within its distal portion and (ii) an integrally-formed, hinged deflector 657 for deflecting fiber optics 611 through opening 655. As in the present embodiment, deflector 657 may be biased in the direction of opening 655. Accordingly, device 651 may additionally include a wire 659 fixed at its distal end 660 to deflector 657 so that, by pulling proximally on wire 659, deflector 657 may be pivoted away from opening 655. (The proximal end of wire 659 preferably remains external to the patient.) In this manner, if one wishes to pass distal end 612 of fiber optics 611 through distal end 661 of member 653, one may pull wire 659 sufficiently proximally to cause deflector 657 to be moved out of the lumen of member 653. Alternatively, if one wishes to pass the distal end of fiber optics 611 through opening 655, one would not pull wire 659, and deflector 657 would cause fiber optics 611 to be directed through opening 655.

As can be appreciated, a desirable attribute of device 651 is that it may be used to observe the uterus from a plurality of alternate vantage points.

Figure 23:
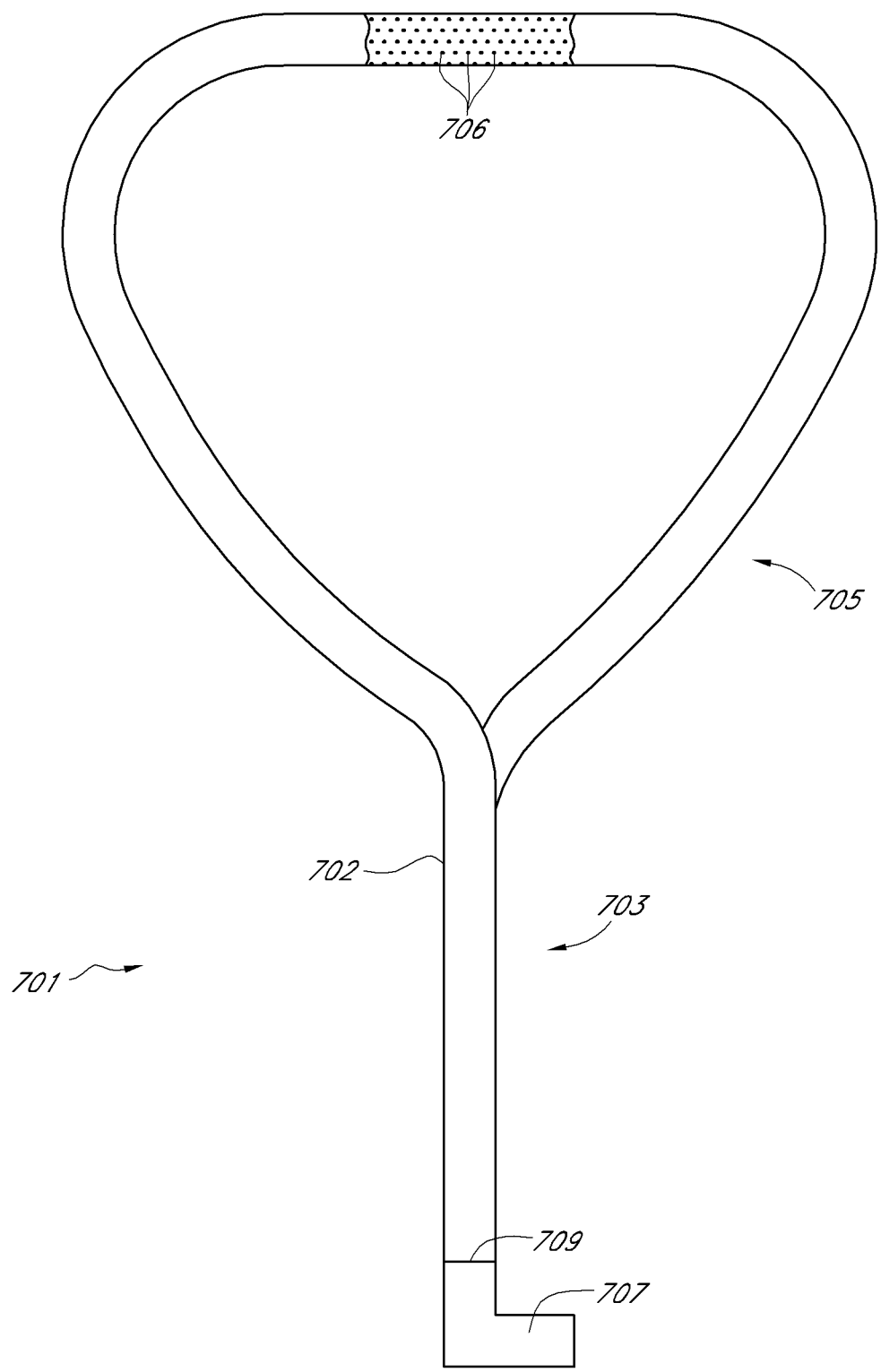
FIG. 23 is a top view, broken away in part, of still yet another embodiment of a device for distending a gynecological cavity, the device being constructed according to the teachings of the present invention and being shown in an expanded state.

Referring now to FIG. 23, there is shown a top view, broken away in part, of another embodiment of a multi-purpose device, the multi-purpose device being constructed according to the teachings of the present invention and being represented by reference numeral 701.

Device 701, which may be used both to distend a gynecological cavity and to illuminate the inside of the gynecological cavity, may include an elongated member 702 shaped to include a proximal shaft portion 703 and distal expandable means. In the present embodiment, said distal expandable means includes a self-expanding loop 705. Preferably, when loop 705 self-expands, loop 705 distends the uterus or other gynecological cavity to an extent equivalent to that which would be attained using the above-described conventional fluid distension technique at a pressure of at least 40 mm Hg but not greater than 100 mm Hg and preferably at a pressure of approximately 70 mm Hg.

To illuminate the gynecological cavity, member 702 may be designed so that light inputted at its proximal end is both transmitted along its length and scattered through its side wall. This may be accomplished, for example, by incorporating particulate matter 706, such as titanium dioxide particles, into a light-conductive material, such as silicone. The light-scattering particles may be located over only a portion of member 702 (for example, only within loop 705) or may be dispersed over the entirety of its length. A light source connector 707 may be disposed at the proximal end 709 of member 702 to permit a light source (not shown) to be coupled to member 702.

In use, the distal end of device 701 may be inserted into a gynecological cavity, such as a uterus, using an appropriately dimensioned introducer device. (The proximal end of device 701 preferably remains external to the patient.) While positioned within the introducer device, loop 705 is compressed to a small profile. However, once loop 705 passes completely through the introducer device, loop 705 self-expands to its expanded state, where it distends the gynecological cavity. A light source may then be connected to connector 707. The input of light into member 702 causes light to be scattered from member 702, thereby illuminating the cavity. When illumination of the distended cavity is no longer desired, the light source may be disconnected from connector 707. When distension of the cavity is no longer desired, device 701 may be removed from the patient by withdrawing loop 705 through the introducer device, the introducer device serving to compress loop 705.

Figure 24:
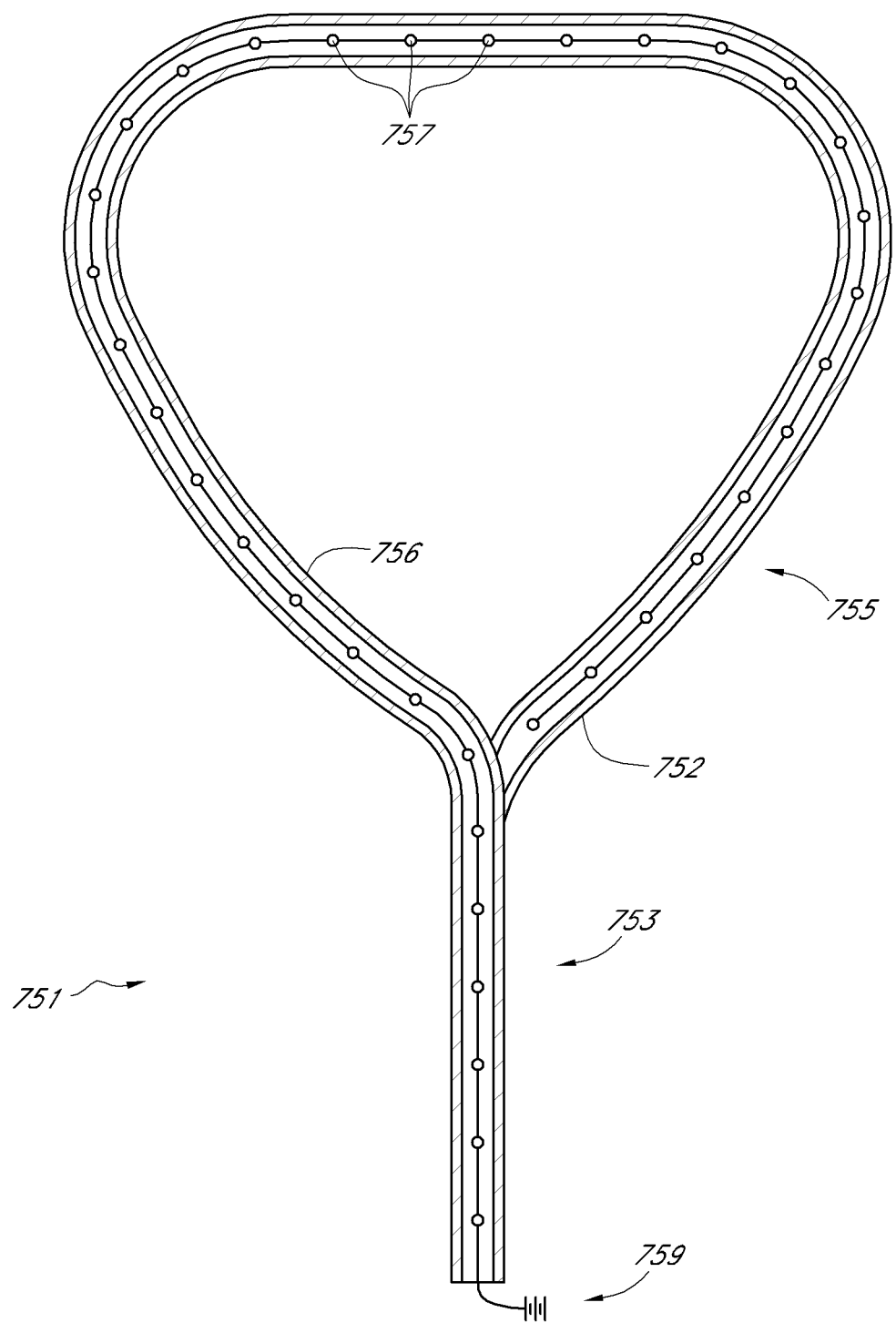
FIG. 24 is a top view, partly in section, of still yet another embodiment of a device for distending a gynecological cavity, the device being constructed according to the teachings of the present invention and being shown in an expanded state.

Referring now to FIG. 24, there is shown a top view, partly in section, of another embodiment of a multi-purpose device, the multi-purpose device being constructed according to the teachings of the present invention and being represented by reference numeral 751.

Device 751, which may be used both to distend a gynecological cavity and to illuminate the inside of the gynecological cavity, may include an elongated member 752 shaped to include a proximal shaft portion 753 and distal expandable means. In the present embodiment, said distal expandable means includes a self-expanding loop 755. Preferably, when loop 755 self-expands, loop 755 distends the uterus or other gynecological cavity to an extent equivalent to that which would be attained using the above-described conventional fluid distension technique at a pressure of at least 40 mm Hg but not greater than 100 mm Hg and preferably at a pressure of approximately 70 mm Hg.

To illuminate the gynecological cavity, member 752 may be a tubular member having a light conductive side wall 756, and device 751 may further include a string of LED's 757 disposed within member 752 and coupled to a power source 759. Although, in the present embodiment, LED's 757 are positioned along substantially the entire length of member 752, one could position LED's 757 over only a portion of the length of member 752 (for example, only within loop 755). Alternatively, instead of using LED's for illumination, member 752 may be filled with a chemiluminescent material that is activated in some manner, such as by heat (e.g., the heat of the patient) or by the self-expansion of loop 755 (e.g., a glow stick activated by breaking a barrier that keeps a chemical reaction from occurring).

In use, the distal end of device 751 may be inserted into a gynecological cavity, such as a uterus, using an appropriately dimensioned introducer device. (The proximal end of device 751 preferably remains external to the patient.) While positioned within the introducer device, loop 755 is compressed to a small profile. However, once loop 755 passes completely through the introducer device, loop 755 self-expands to its expanded state, where it distends the gynecological cavity. Power source 759, which may be a battery or other source of electricity, may then be connected to LED's 757. The light from LED's 757 radiates through side wall 756 and illuminates the cavity. When illumination of the distended cavity is no longer desired, power source 759 may be disconnected from LED's 757. When distension of the cavity is no longer desired, device 751 may be removed from the patient by withdrawing loop 755 through the introducer device, the introducer device serving to compress loop 755.

Figure 25:
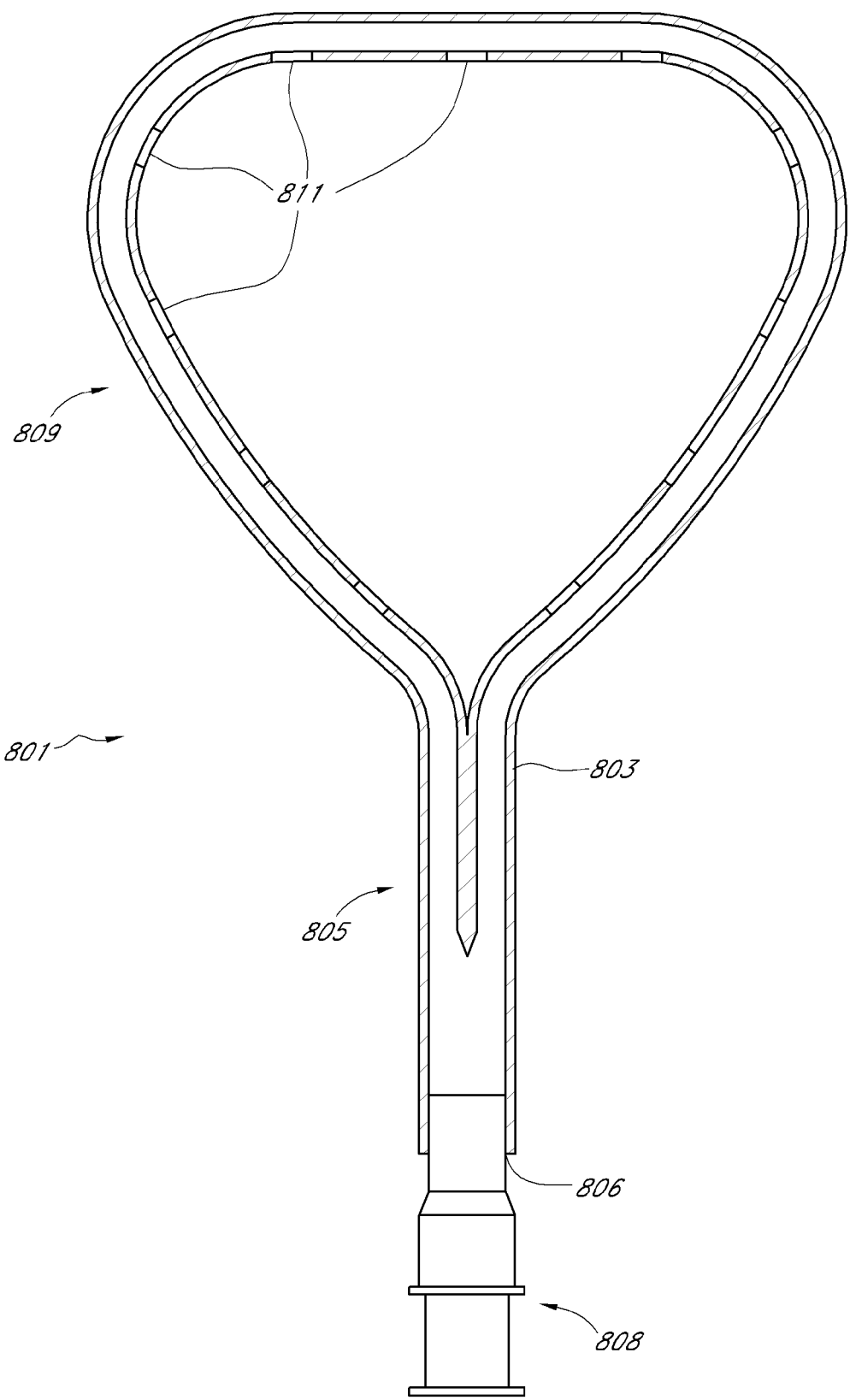
FIG. 25 is a top view, partly in section, of still yet another embodiment of a device for distending a gynecological cavity, the device being constructed according to the teachings of the present invention and being shown in an expanded state with a syringe attached thereto.

Referring now to FIG. 25, there is shown a top view, partly in section, of another embodiment of a multi-purpose device, the multi-purpose device being constructed according to the teachings of the present invention and being represented by reference numeral 801.

Device 801, which may be used both to distend a gynecological cavity and to provide a conduit for fluid to be dispensed into the gynecological cavity, may include an elongated, resilient, tubular member 803 shaped to include a proximal shaft portion 805 and distal expandable means. In the present embodiment, said distal expandable means comprises a self-expanding loop 809. Preferably, when loop 809 expands, loop 809 distends the uterus or other gynecological cavity to an extent equivalent to that which would be attained using the above-described conventional fluid distension technique at a pressure of at least 40 mm Hg but not greater than 100 mm Hg and preferably at a pressure of approximately 70 mm Hg.

Shaft portion 805 may have a proximal opening 806 adapted to receive a syringe 808. One or more transverse openings 811 may be located in loop 809 so that fluid introduced into member 803 by syringe 808 may be dispensed from member 803 through openings 811 into the gynecological cavity. Examples of fluids that may be suitable for dispensing using device 801 include, but are not limited to, pain medications (e.g., analgesics, lidocaine), saline solutions for irrigation, sclerosing agents to stop bleeding, agents to destroy endometrium (e.g., trichloroacetic acid), etc.

In use, the distal end of device 801 may be inserted into a gynecological cavity, such as a uterus, using an appropriately dimensioned introducer device. (The proximal end of device 801 preferably remains external to the patient.) While positioned within the introducer device, loop 809 is compressed to a small profile. However, once loop 809 passes completely through the introducer device, loop 809 self-expands to its expanded state, where it distends the gynecological cavity. A syringe 808 may then be inserted into opening 806, and a desired fluid may be dispensed from syringe 808. The fluid dispensed from syringe 808 into member 803 travels through member 803 and empties into the gynecological cavity at openings 811. When the dispensing of fluid into the gynecological cavity is no longer desired, syringe 808 may be disconnected from member 803. When distension of the cavity is no longer desired, device 801 may be removed from the patient by withdrawing loop 809 through the introducer device, the introducer device serving to compress loop 809.

Figure 26:
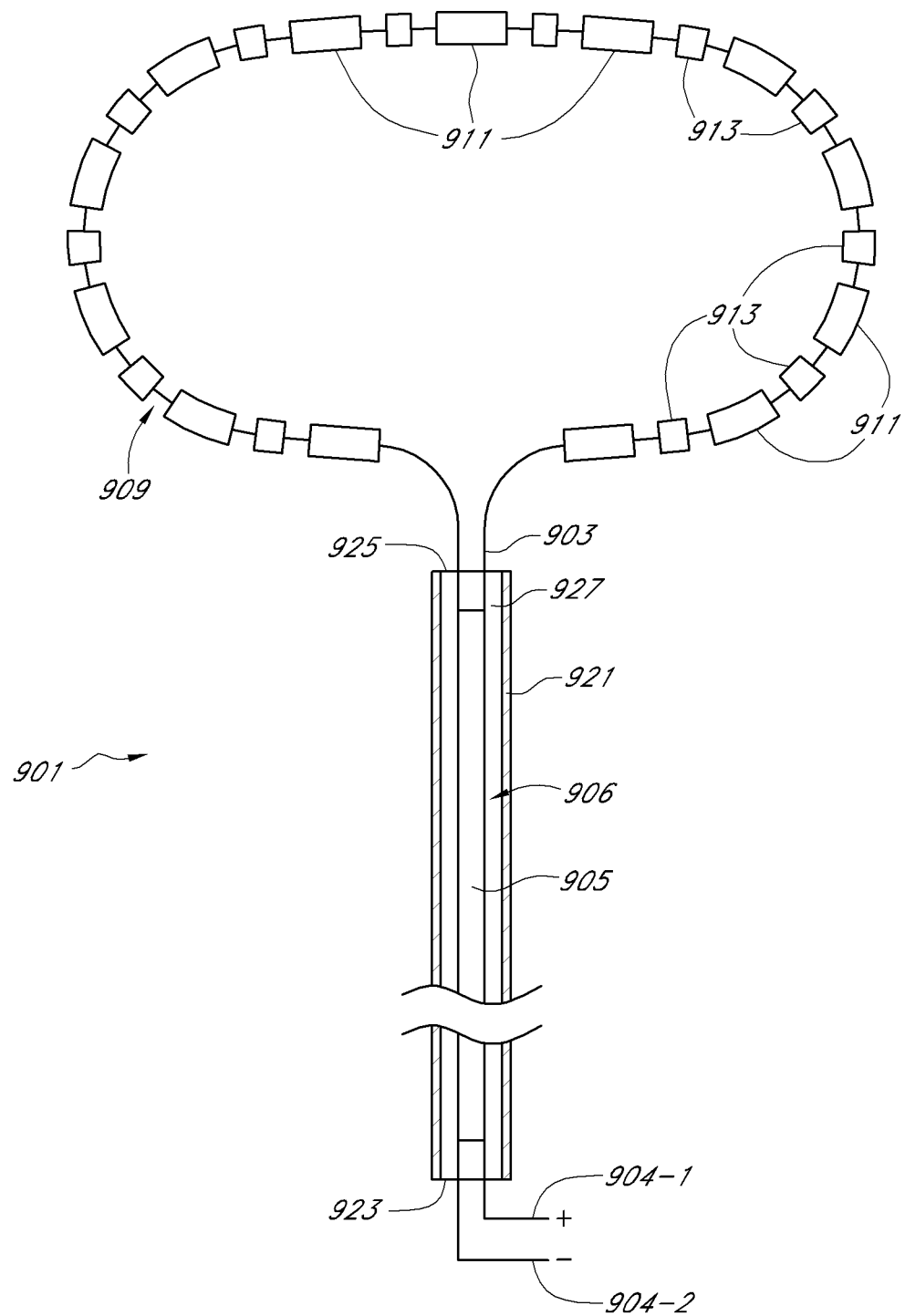
FIG. 26 is a top view, partly in section, of still yet another embodiment of a device for distending a gynecological cavity, the device being constructed according to the teachings of the present invention and being shown in an expanded state.

Referring now to FIG. 26, there is shown a top view, partly in section, of another embodiment of a multi-purpose device, the multi-purpose device being constructed according to the teachings of the present invention and being represented by reference numeral 901.

Device 901, which may be used both to distend a gynecological cavity and to perform an electrocautery ablation of the endometrium of the cavity, may include an elongated, resilient, electrically-conductive member 903 having a first end 904-1 and a second end 904-2. First and second ends 904-1 and 904-2 may be physically coupled together, but electrically separated by an insulating material 905, to form a unified shaft 906. The intermediate portion of member 903 may be configured to form expandable means. In the present embodiment, said expandable means comprises a self-expanding loop 909. Preferably, when loop 909 expands, loop 909 distends the uterus or other gynecological cavity to an extent equivalent to that which would be attained using the above-described conventional fluid distension technique at a pressure of at least 40 mm Hg but not greater than 100 mm Hg and preferably at a pressure of approximately 70 mm Hg.

A plurality of roller cauterizing units 911 are rotatably and coaxially mounted on member 903 within loop 909. Units 911 may be conventional roller cauterizing units, such as those disclosed in U.S. Pat. Nos. 5,634,924, 5,549,605 and 5,669,700, all of which are incorporated herein by reference.

A plurality of electrically insulating members 913 are fixedly mounted on member 903 within loop 909, insulating members 913 being positioned between adjacent cauterizing units 911.

Device 901 may further include a delivery sheath 921 or other introducer device. Sheath 921, which may be a unitary tubular member, may be shaped to include a proximal end 923, a distal end 925, and a longitudinal lumen 927. Lumen 927 may be dimensioned to slidably receive shaft 906 and to maintain loop 909, when positioned therein, in a compressed state. Distal end 925 of sheath 921 may be adapted to be inserted into the uterus transcervically, with proximal end 923 of sheath 921 preferably remaining external to the patient. To minimize discomfort to the patient, such as by obviating the need for administration of an anesthetic to the patient, the outer diameter of that portion of sheath 921 inserted into the patient is preferably less than about 5.5 mm.

In use, loop 909, together with cauterizing units 911 and insulating members 913 mounted thereon, is inserted into lumen 927 of sheath 921 through proximal end 923. Distal end 925 of sheath 921 is then inserted into a gynecological cavity, such as a uterus. (Proximal end 923 of sheath 921 preferably remains external to the patient.) Shaft 906 is pushed distally through lumen 927 until loop 909 passes completely through sheath 921 and into the cavity. No longer compressed by sheath 921, loop 909 immediately self-expands to its expanded state, where it distends the gynecological cavity. A source of electricity may then be connected to the member 903, causing cauterizing units 911 to become actuated. Shaft 906 is then rotated about its longitudinal axis. This causes loop 909 to be correspondingly rotated and causes cauterizing units 911 to be drawn across the walls of the cavity, where units 911 perform an electrocautery ablation of the walls. When further electrocautery ablation of the walls is no longer desired, member 903 may be disconnected from the power source. When distension of the cavity is no longer desired, loop 909 may be removed from the patient by withdrawing loop 909 through sheath 921, sheath 921 serving to compress loop 909.

Figure 27:
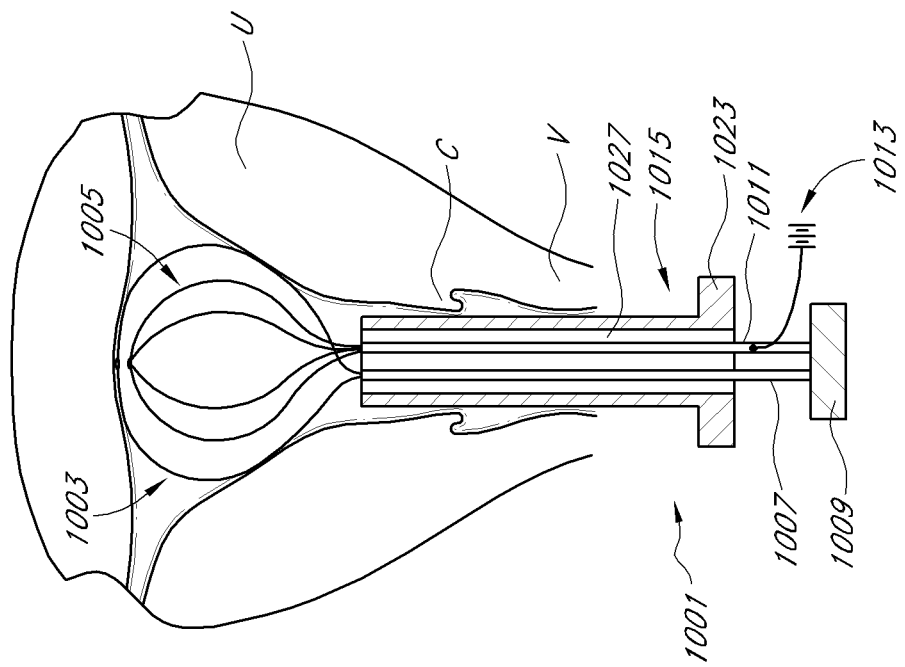
FIG. 27 is a top view, partly in section, of still yet another embodiment of a device for distending a gynecological cavity, the device being constructed according to the teachings of the present invention and being shown in an expanded state.

Referring now to FIG. 27, there is shown a top view, partly in section, of another embodiment of a multi-purpose device, the multi-purpose device being constructed according to the teachings of the present invention and being represented by reference numeral 1001.

Device 1001, which may be used both to distend a gynecological cavity and to perform a resection, may include a larger diameter expandable member 1003 and a smaller diameter expandable member 1005, smaller diameter expandable member 1003 being nested within larger diameter expandable member 1005. In the present embodiment, each of expandable member 1003 and expandable member 1005 comprises a self-expanding whisk-like structure. Larger expandable member 1003, which is preferably used for distension, may be fixed at its proximal end to a positioning wire 1007, which, in turn, may be fixed at its proximal end to a handle 1009. Smaller expandable member 1005, which is preferably used for resection, may be fixed at its proximal end to a positioning wire 1011, which, in turn, may be fixed at its proximal end to handle 1009. Wire 1011 may also be electrically connected to a power source 1013 to provide electricity to expandable member 1003.

Device 1001 may further include a sheath 1015 or other introducer device. Sheath 1015, which may be a unitary tubular member, may be shaped to include a proximal end 1023, a distal end 1025, and a longitudinal lumen 1027. Distal end 1025 may be adapted to be inserted into the uterus transcervically, with proximal end 1023 preferably remaining external to the patient. To minimize discomfort to the patient, such as by obviating the need for administration of an anesthetic to the patient, the outer diameter of sheath 1015 (or at least that portion of sheath 1015 inserted into the patient) is preferably less than about 5.5 mm. Wires 1007 and 1011 may be slidably disposed within sheath 1015 so that, by appropriately positioning wires 1007 and 1011 relative to sheath 1015, expandable members 1003 and 1005 may be positioned within sheath 1015, where they are maintained in a compressed state by sheath 1015, or may be positioned distally relative to sheath 1015, where they are free to expand to their expanded states.

Figure 28:
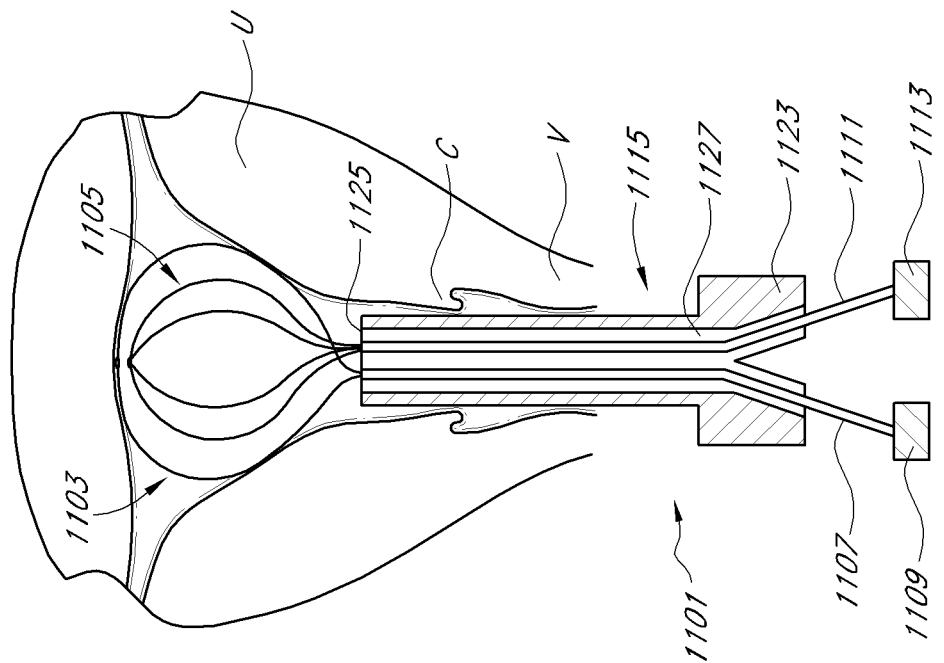
FIG. 28 is a top view, partly in section, of still yet another embodiment of a device for distending a gynecological cavity, the device being constructed according to the teachings of the present invention and being shown in an expanded state.

Referring now to FIG. 28, there is shown a top view, partly in section, of another embodiment of a multi-purpose device, the multi-purpose device being constructed according to the teachings of the present invention and being represented by reference numeral 1101.

Device 1101, which may be used to distend a gynecological cavity and to grab or otherwise manipulate tissue, may include a larger diameter expandable member 1103 and a smaller diameter expandable member 1105, smaller diameter expandable member 1103 being nested within larger diameter expandable member 1105. In the present embodiment, each of expandable member 1103 and expandable member 1105 comprises a self-expanding whisk-like structure. Larger expandable member 1103, which is preferably used for distension, may be fixed at its proximal end to a positioning wire 1107, which, in turn, may be fixed at its proximal end to a handle 1109. Smaller expandable member 1105, which is preferably used for grabbing or snaring, may be fixed at its proximal end to a positioning wire 1111, which, in turn, may be fixed at its proximal end to a handle 1113. As can be appreciated, because wires 1107 and 1111 are attached to different handles, expandable members 1103 and 1105 are independently operable.

Device 1101 may further include a sheath 1115 or other introducer device. Sheath 1115, which may be a unitary tubular member, may be shaped to include a proximal end 1123, a distal end 1125, and a longitudinal lumen 1127. Distal end 1125 may be adapted to be inserted into the uterus transcervically, with proximal end 1123 preferably remaining external to the patient. To minimize discomfort to the patient, such as by obviating the need for administration of an anesthetic to the patient, the outer diameter of sheath 1115 (or at least that portion of sheath 1115 inserted into the patient) is preferably less than about 5.5 mm. Wires 1107 and 1111 may be slidably disposed within sheath 1115 so that, by appropriately positioning wires 1107 and/or 1111 relative to sheath 1115, one or both of expandable members 1103 and 1105, respectively, may be positioned within sheath 1115, where they are maintained in a compressed state by sheath 1115, or one or both of expandable members 1103 and 1105 may be positioned distally relative to sheath 1115, where they are free to expand to their expanded states.

In the various embodiments discussed above, non-fluid mechanical means are used to distend the gynecological cavity. According to a further aspect of the invention, fluid means are used initially to distend the cavity, and non-fluid mechanical means are thereafter used to maintain the cavity in its distended state. As can be appreciated, this two-part distension technique may make use of many, if not all, of the devices described above. An illustration of this two-part technique is shown in FIGS. 29(a) and 29(b). More specifically, in FIG. 29(a), a distension device 1201 has been inserted into a patient, and a quantity of a distension medium has been dispensed from a fluid reservoir 1203 through an introducer device 1205 and into the uterus, causing the uterus to be distended. In FIG. 29(b), a shaft 1207 is moved distally relative to introducer device 1205, causing a self-expanding basket 1207 to be ejected from introducer device 1205 into the uterus, where it immediately self-expands to maintain the uterus in its distended state.

Figure 30:
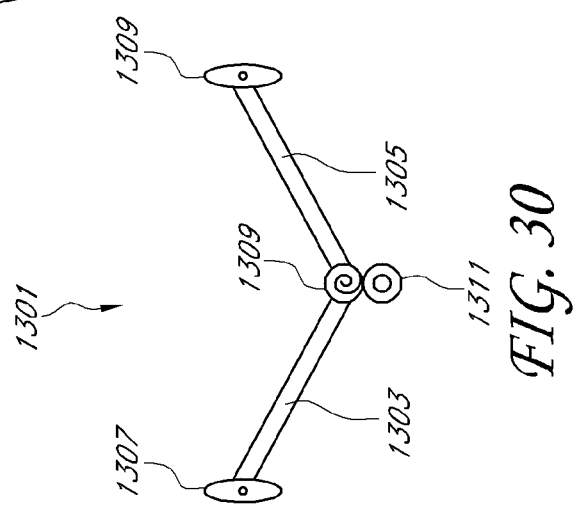
FIG. 30 is a top view of an alternate device for use in practicing the two-part distension method illustrated in FIGS. 29(a) and 29(b)

Referring now to FIG. 30, there is shown a top view of an alternate device to device 1201 for use in practicing the two-part distension method illustrated in FIGS. 29(a) and 29(b), the alternate device being constructed according to the teachings of the present invention and being represented generally by reference numeral 1301.

Device 1301 may comprise a pair of arms 1303 and 1305. A pressure pad 1307 may be mounted on the outer end of arm 1303, and a pressure pad 1309 may be mounted on the outer end of arm 1305. The inner ends of arms 1303 and 1305 may be joined to a spring 1309 that biases arms 1303 and 1305 away from one another. A loop 1311, whose purpose will become apparent below, may be positioned adjacent to spring 1309.

Figure 31B:
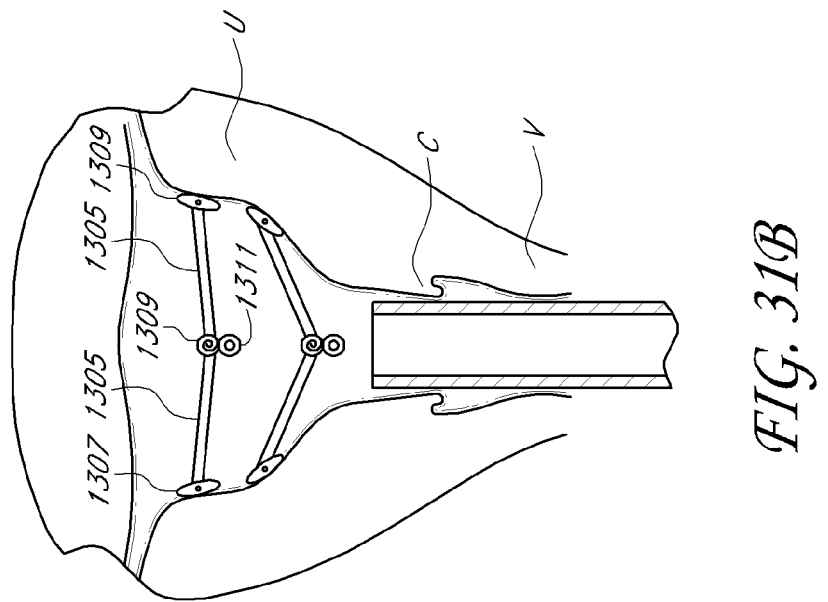
FIGS. 31(a) and 31(b) are top views, partly in section, showing one way in which the device of FIG. 30 may be used to practice the two-part method of FIGS. 29(a) and 29(b)
Figure 31A:
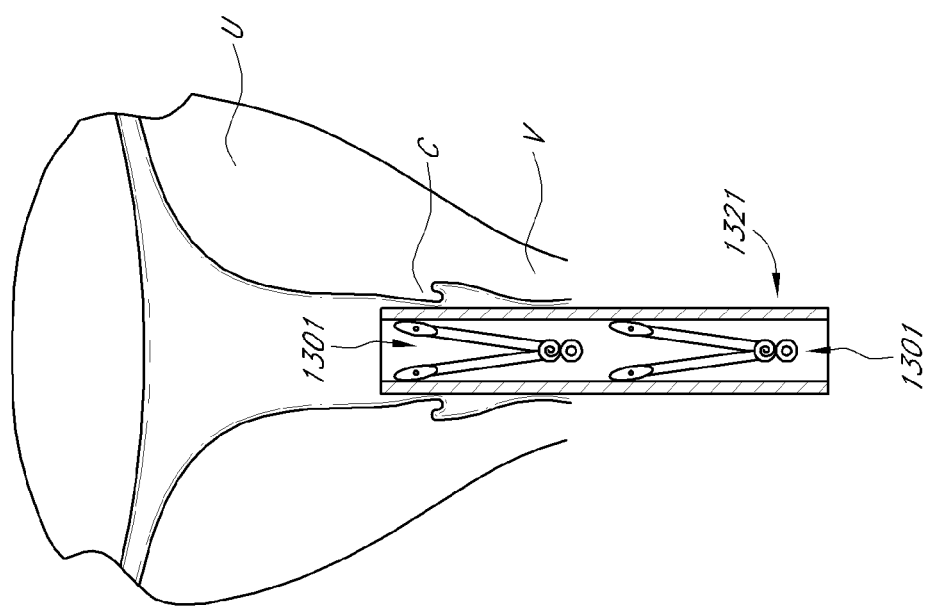

Referring now to FIGS. 31(a) and 31(b), there is shown one way in which device 1301 may be used to distend a gynecological cavity. In FIG. 31(a), a pair of devices 1301 are shown loaded into an introducer device 1321, the introducer device 1321 having been inserted into a patient. The uterus of the patient is shown distended with a distension fluid. Devices 1301 may be ejected from introducer device 1321 by an ejector rod (not shown). In FIG. 31(b), devices 1301 are shown deployed in the uterus to maintain the uterus in its already distended state. When distension of the uterus is no longer desired, devices 1301 may be removed from the uterus by inserting a hook or similar structure into loop 1311 and then pulling device 1301 into introducer device 1321.

Figure 32B:
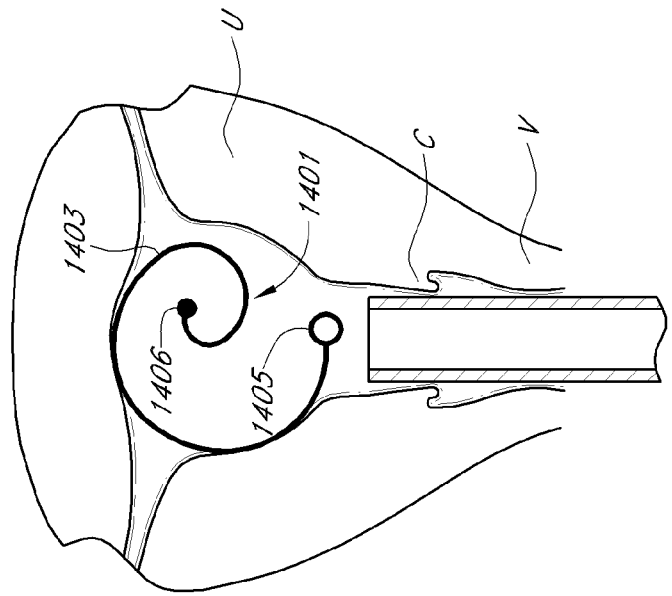
FIGS. 32(a) and 32(b) are top views, partly in section, showing an alternate device being used to practice the two-part method of FIGS. 29(a) and 29(b).
Figure 32A:
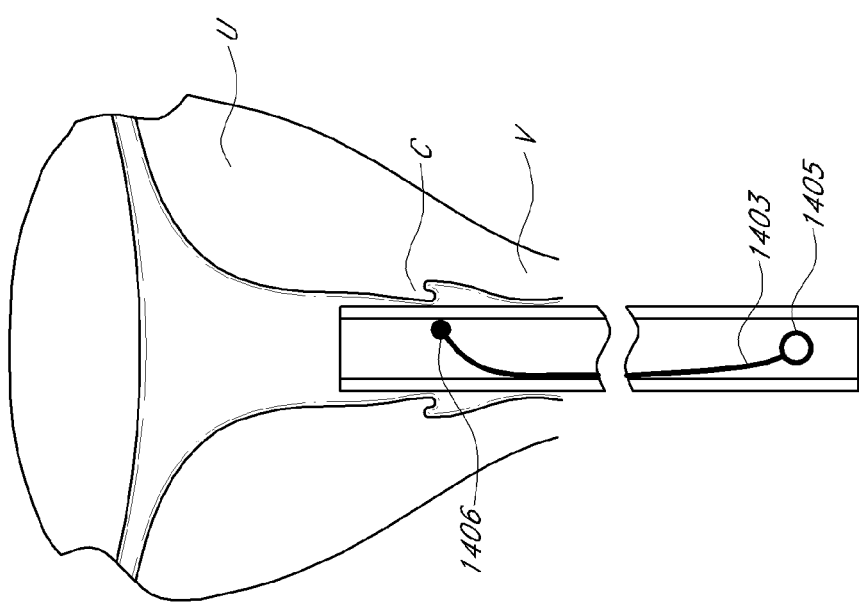

Referring now to FIGS. 32(a) and 32(b), there are shown top views, partly in section, of a second alternate device to device 1201 for use in practicing the two-part distension method illustrated in FIGS. 29(a) and 29(b), the second alternate device being constructed according to the teachings of the present invention and being represented generally by reference numeral 1401.

Device 1401 may comprise a coiled wire 1403 having a loop 1405 at its proximal end and a ball 1406 at its distal end. Device 1401 may be used in a fashion analogous to that described above in connection with device 1301.

Referring now to FIGS. 33(a) and 33(b), there are shown top views, partly in section, illustrating an alternate embodiment for distending a uterus or gynecological cavity using an inflatable bladder or balloon cage 3301. The inflatable bladder or balloon cage 3301 is dimensioned to contact at least a portion of the wall of a uterus or other gynecological cavity to maintain distension of the cavity. In the illustrated embodiment, the inflatable bladder or balloon cage 3301 is delivered to the target or surgical area through a delivery tube 3303. The inflatable bladder or balloon cage 3301 is tethered to a fill tube 3305, which is used to fill the inflatable bladder or balloon cage 3301 with air, liquid, gel, or the like during the inflation of the bladder or balloon cage 3301. The tether is also used to remove the air, liquid, gel, or the like during the deflation of the bladder or balloon cage 3301, and the tether or a separate pull wire or grasper may be used to draw the bladder or balloon cage 3301 back into the delivery tube 3303.

As illustrated in FIG. 33(b), the delivery tube 3303 has been proximally retracted to expose the balloon cage 3301. Balloon cage 3301 has been inflated, to define a working space. The balloon cage 3301 comprises at least a first strut 3307 and a second strut 3309 oriented in an arcuate configuration to provide a hemispherical construct. The first strut 3307 and second strut 3309 are in communication with the fill tube 3305 by way of a third strut 3311. At least two or three or four or more struts may be provided, depending upon the desired performance of the cage 3301. In addition, the inflated configuration of the cage 3301 may be hemispherical as illustrated, spherical, elliptical, or any of a variety of three dimensional configurations depending upon the desired shape of the resulting working space. The struts will generally define at least one window 3313 there between, through which tissue will be exposed and potentially prolapsed, to be treated using the therapeutic or diagnostic devices described elsewhere herein. The treatment device may be advanced axially through the delivery tube 3303, or in parallel outside of the delivery tube 3303 depending upon the desired instrument configuration.

Figure 34B:
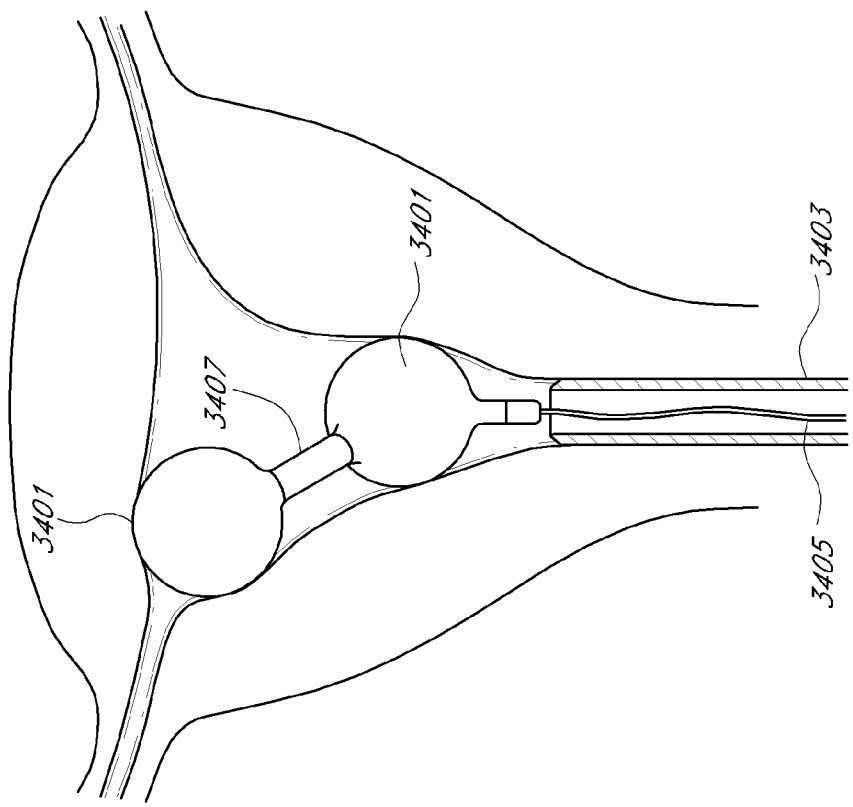
FIGS. 34(a) and 34(b) are top views, partly in section, illustrating an alternate embodiment for distending a gynecological cavity using a restricted balloon.
Figure 34A:
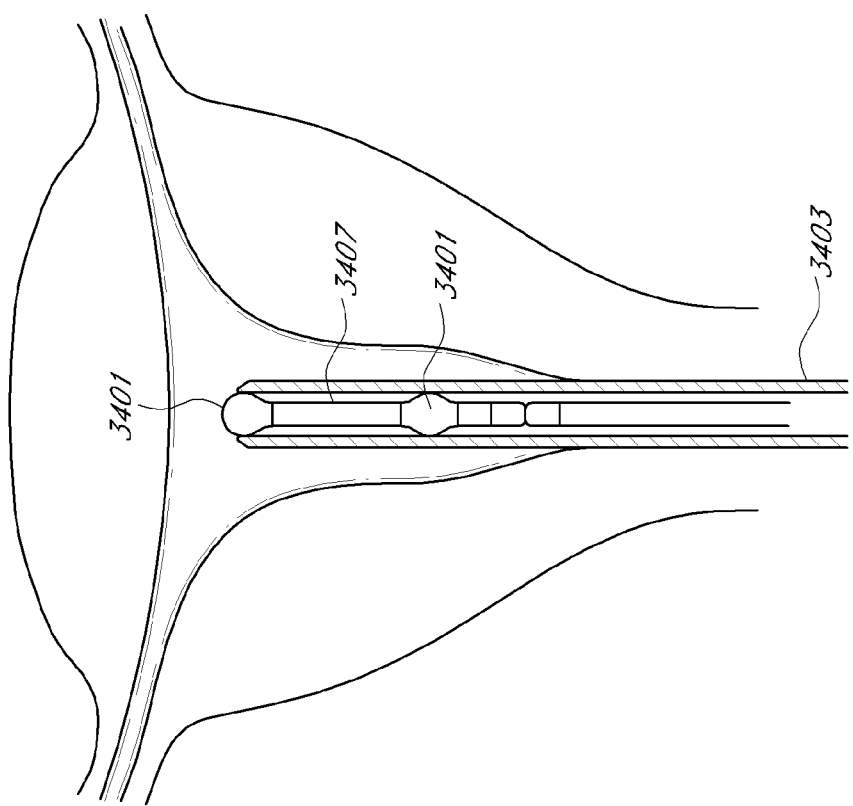

Referring to FIGS. 34(a) and 34(b), there are top views, partly in section, illustrating an alternate embodiment for distending a gynecological cavity using dual balloons or a restricted balloon 3401. In the illustrated embodiment, the inflatable restricted balloon 3401 is delivered to the target or surgical area through a delivery tube 3403. The restricted balloon 3401 is tethered to a fill tube 3405, which is used to fill the restricted balloons 3401 with air, liquid, gel, or the like during the inflation of the restricted balloon 3401. The tether is also used to remove the air, liquid, gel, or the like during the deflation of the restricted balloon 3401, and the tether or a separate pull wire or grasper is used to draw the restricted balloon 3401 back into the delivery tube 3403. To localize the distension of the gynecological cavity, the restriction device 3407 is customizable to adjust the shape and form of the restricted balloon 3401.

The balloon 3401 will generally comprise at least a first lobe spaced apart from a second lobe to create a working space in between. The first and second lobes may be proximal and distal ends of a common balloon, having a central portion necked down to the catheter shaft such as by the use of an external restraining band or by internal adhesive bonding. Alternatively, two separate balloons may be provided spaced apart along a shaft, and which may be inflated through a common inflation lumen or through two distinct inflation lumens if it is desirable to inflate the lobes sequentially. Any of a variety of materials may be utilized for any of the inflatable embodiments disclosed herein, such as materials well known in the angioplasty balloon arts including Nylon, PET, and various polyesters and densities of polyethylene. Alternatively, more elastic materials such as silicone or latex may be utilized, depending upon the desired functionality.

Figure 35B:
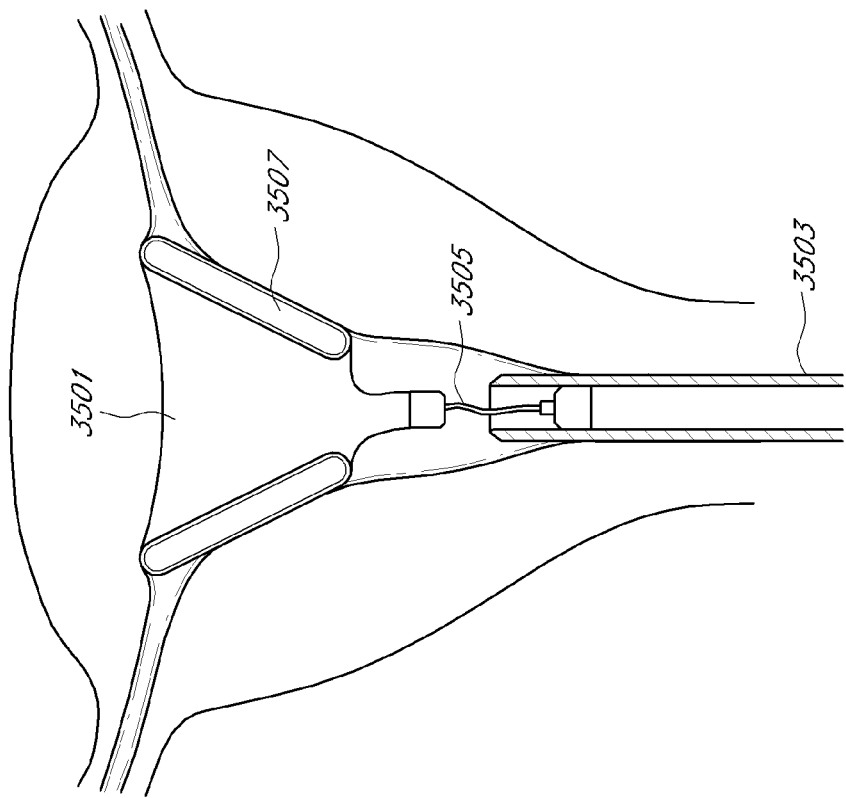
FIGS. 35(a) and 35(b) are top views, partly in section, illustrating an alternate embodiment for distending a gynecological cavity using a film air bladder having a pre-shaped structure.
Figure 35A:
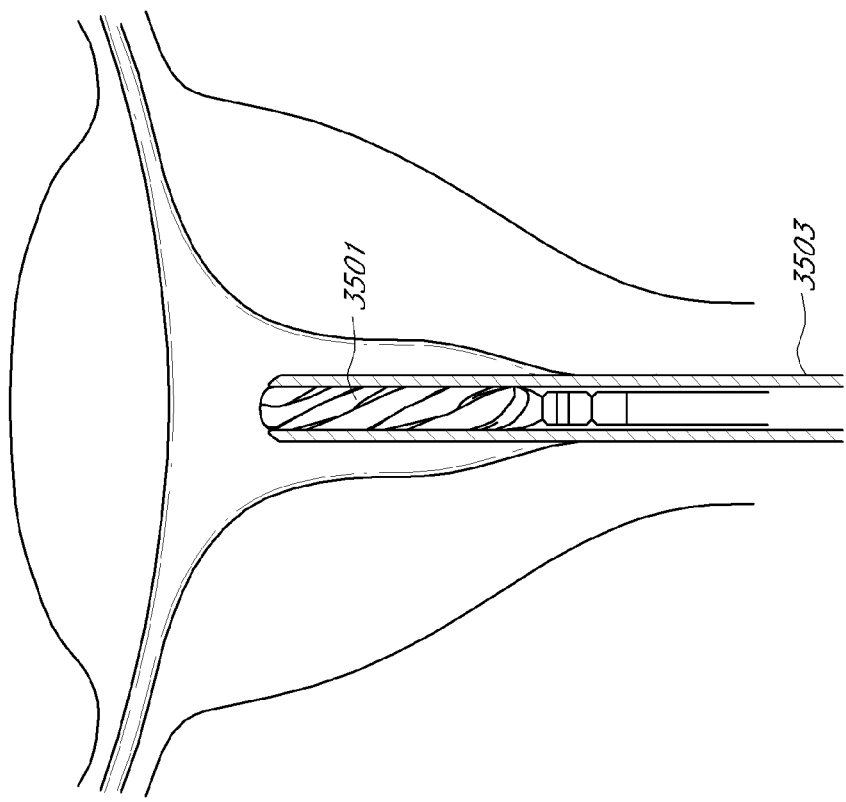

Referring to FIGS. 35(a) and 35(b), there are top views, partly in section, illustrating an alternate embodiment for distending a gynecological cavity using a conical air bladder 3501 having a pre-shaped structure. In the illustrated embodiments, the air bladder 3501 is delivered to the target or surgical area through a delivery tube 3503. The bladder 3501 is tethered to a fill tube 3505, which is used to fill the balloon 3501 with air, liquid, gel, or the like during the inflation of the balloon 3501. The tether may also be used to remove the air, liquid, gel, or the like during the deflation of the balloon 3501, and the tether is used to draw the balloon 3501 back into the delivery tube 3503.

In the illustrated embodiment, the balloon 3501 is configured in a generally frusto conical shape, having a relatively small diameter proximal end and a relatively larger diameter distal end for exposing a working site on the wall of the uterus or other organ. A single continuous annular balloon chamber 3507 may be defined within the balloon 3501. Alternatively, a plurality of discrete chambers may be provided in the wall of the balloon 3501.

Any of a variety of steering mechanisms such as pull wires and push wires may extend through the delivery tool 3503 and attach to the balloon 3501, to allow lateral inclination of the longitudinal axis of the balloon 3501 to access treatment sites which are displaced laterally from the longitudinal axis of the delivery tube 3503.

In some embodiments, the film utilized to construct balloon 3501 comprises Mylar, or other polyester films, or other materials disclosed herein or known in the art.

Figure 36B:
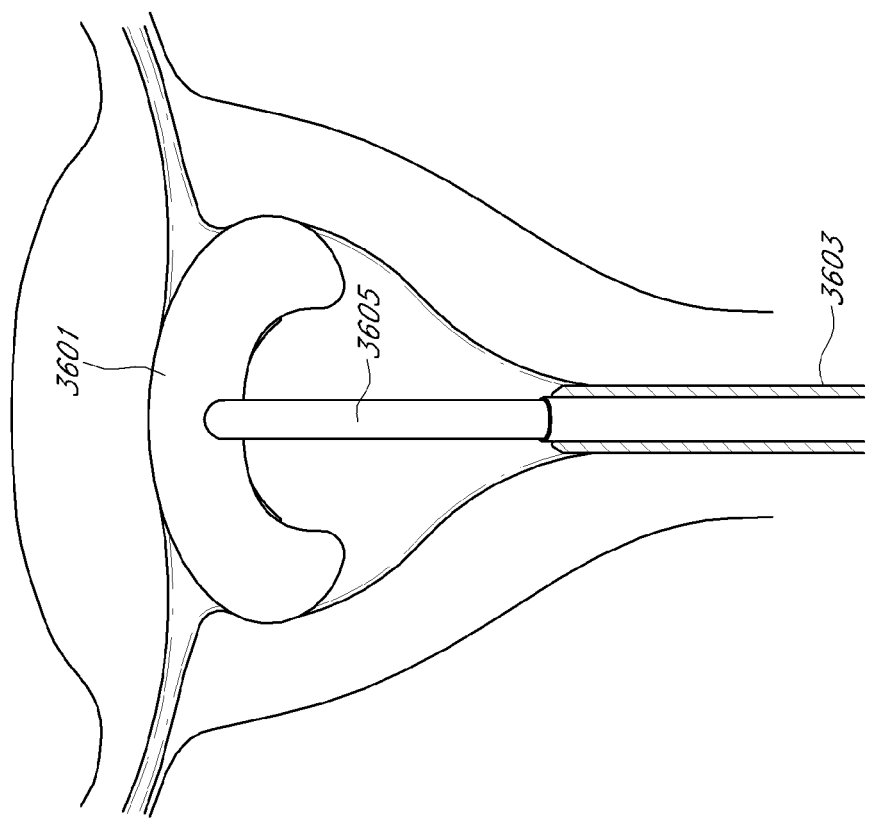
FIGS. 36(a) and 36(b) are top views, partly in section, illustrating an alternate embodiment for distending a gynecological cavity using a spring mesh.
Figure 36A:
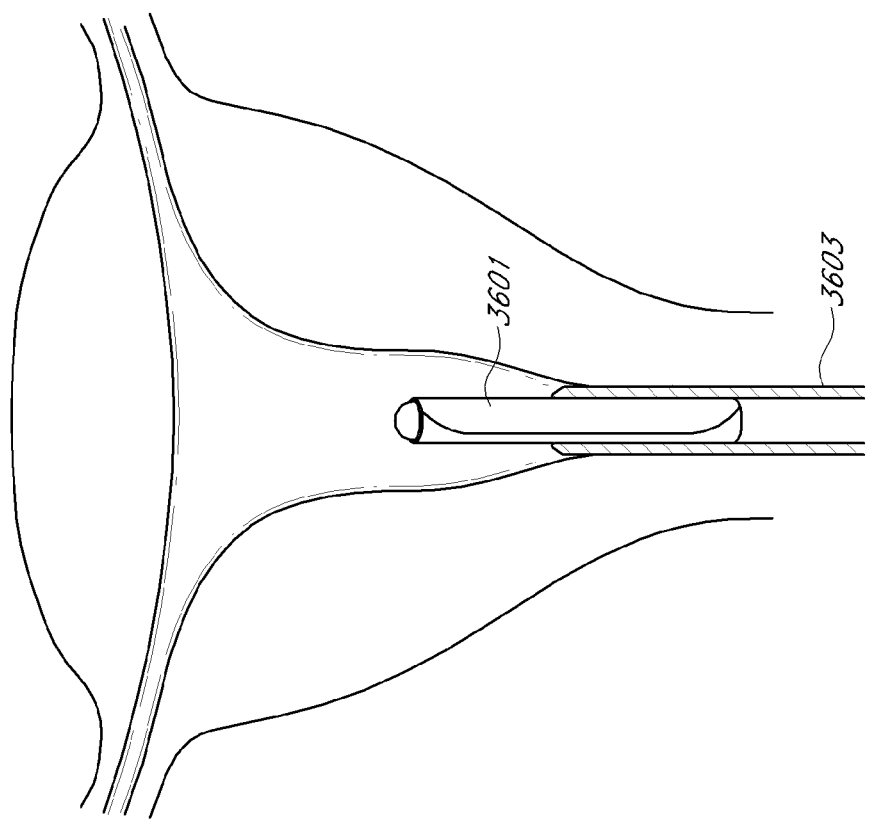

Referring to FIGS. 36(a) and 36(b), there are top views, partly in section, illustrating an alternate embodiment for distending a gynecological cavity using a spring mesh 3601. In the illustrated embodiments, the spring mesh 3601 is delivered to the target or surgical area through a delivery tube 3603. Once deployed in the cavity, the spring mesh 3601 unravels or otherwise enlarges under spring force. The spring mesh 3601 is tethered to a tether tube or cable 3605, which is configured to retract the mesh into the delivery tube 3603 for removal. To localize the distension of the gynecological cavity, the structure of the spring mesh 3601, in some embodiments, is customizable so as to adjust the shape and form of the spring mesh 3601. In some embodiments, the spring mesh comprises nitinol or other similar materials.

Figure 37B:
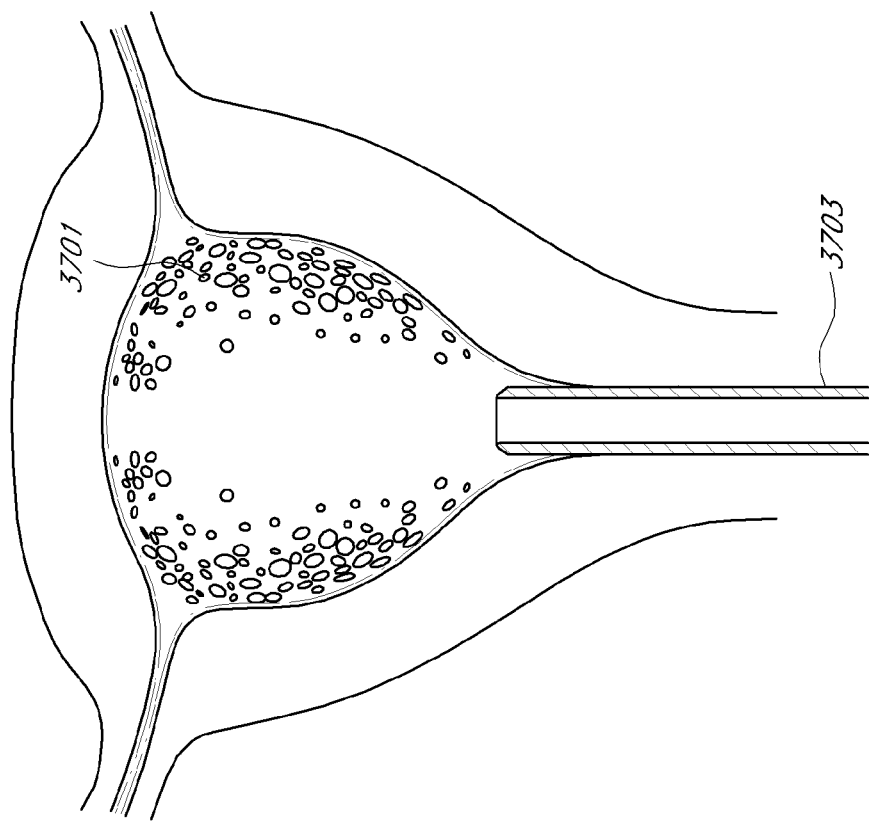
FIGS. 37(a) and 37(b) are top views, partly in section, illustrating an alternate embodiment for distending a gynecological cavity using an expandable foam pill.
Figure 37A:
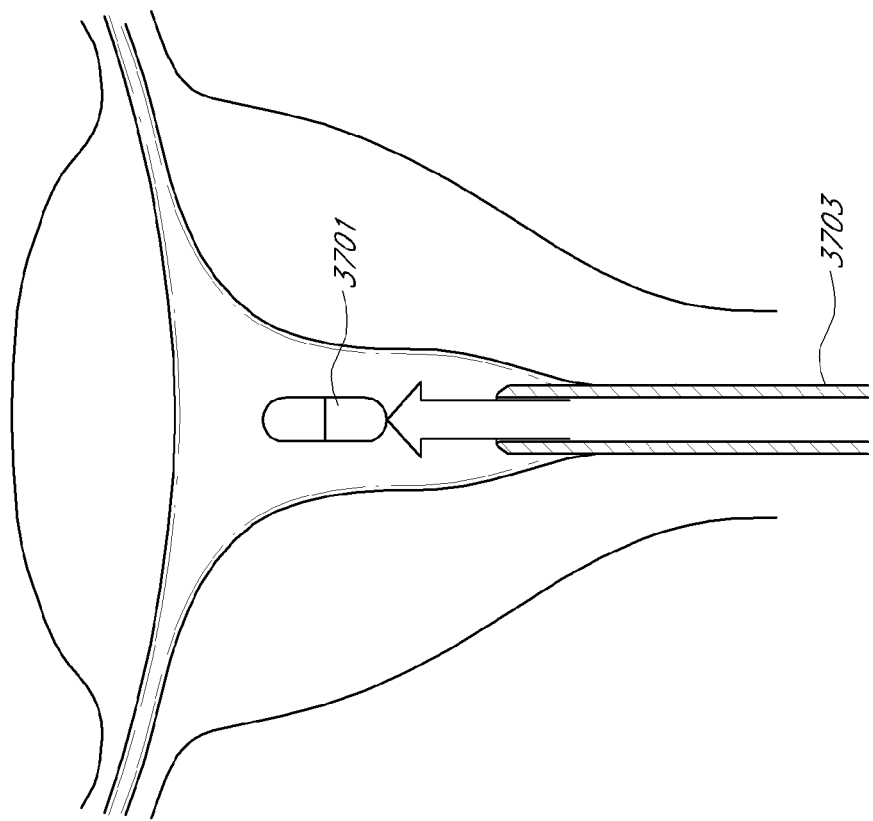

Referring to FIGS. 37(a) and 37(b), there are top views, partly in section, illustrating an alternate embodiment for distending a gynecological cavity using an expandable foam, which may be delivered in the form of a pill 3701. In the illustrated embodiments, the foam pill 3701 is delivered to the target or surgical area through a delivery tube 3703. In other embodiments, the foam pill 3701 is in the form of two liquids that are injected, pumped, or inserted into the cavity. After the foam pill 3701 or the liquids are inserted into the cavity, a chemical reaction occurs to create a pressurized solidified clear foam or gel that a probe or morcellator can pass through. In certain embodiment, the foam or gel is time dissolvable and is either absorbed by the body or passed out of the cavity over time. In other embodiments, the foam or gel is aspirated out of the cavity using delivery tube 3703 or other device. The foam or gel comprises any number of chemicals or materials known to a person of skill in the art.

Referring to FIG. 38, there is a top view, partly in section, illustrating an alternate embodiment for distending a gynecological cavity using magnet blocks 3801. In the illustrated embodiment, the magnetic building blocks 3801 are delivered to the target or surgical area through a delivery tube 3803. Each building block 3801 is configured to bond to opposing poles to build a structure capable of distending the gynecological cavity. To remove the structure from the cavity, the structure would be pulled apart using a grasper and drawn into the delivery tube 3803 one block at a time.

Referring to FIG. 39, there is top view, partly in section, illustrating an alternate embodiment for distending a gynecological cavity using internal magnets 3901 and/or external magnets 3905. In the illustrated embodiment, the internal magnets 3901 are delivered to and are placed at the target or surgical area through a delivery tube 3903. After the internal magnets 3901 have been positioned, the external magnet 3905 is positioned outside the cavity or the body to attract and engage the internal magnets 3901. Once engaged, the external magnet 3905 is pulled away from the body or increased in strength such as by increasing the supply voltage to an electromagnet to distend the cavity. To remove the internal magnets 3901 from the cavity, the internal magnets 3901 are drawn into the delivery tube 3903, such as by a grasper or by the use of a magnetic wand.

Figure 40B:
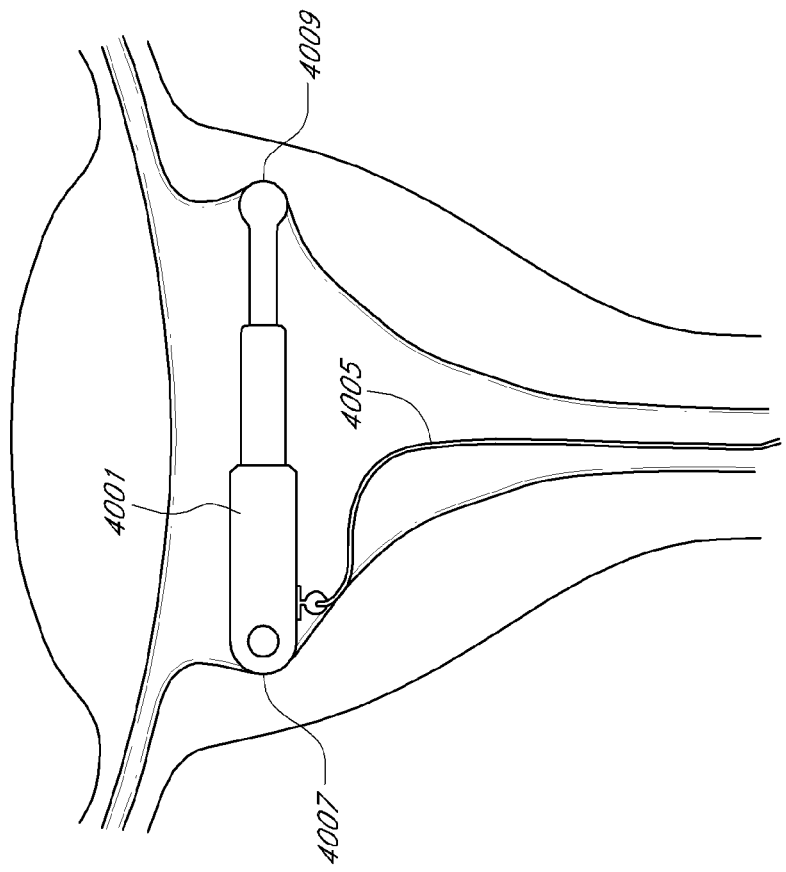
FIGS. 40(a) and 40(b) are top views, partly in section, illustrating an alternate embodiment for distending a gynecological cavity using an extendible piston.
Figure 40A:
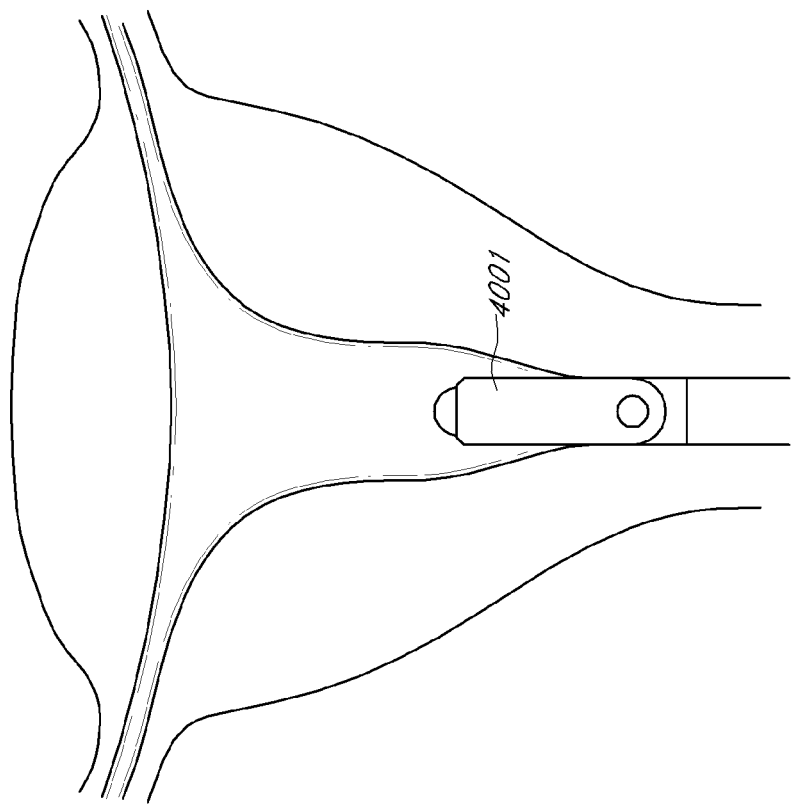

Referring to FIGS. 40(a) and 40(b), there are top views, partly in section, illustrating an alternate embodiment for distending a gynecological cavity using an extendible piston 4001. In the illustrated embodiment, the extendible piston 4001 is a hydraulic piston that is delivered through the cervix and to the target or surgical area. In certain embodiments, the extendible piston 4001 is positioned at a substantially 90° angle with respect to the longitudinal axis of the uterus. The extendible piston 4001 is tethered to a fill tube or tether 4005, which is used to fill the extendible piston 4001 with air, liquid, gel, or the like to extend the extendible piston 4001 using pressure from the air, liquid, gel, or the like. The tether is also used to remove the air, liquid, gel, or the like to reduce the size of the extendible piston 4001. To remove the extendible piston 4001 from the cavity, the pressure inside the extendible piston 4001 is removed to reduce the size of the piston, and the piston is pulled through the cervix using the tether 4005.

The extendable piston 4001 may be pivotably connected to a control wire, and provided with one or two or more pull wires to manipulate the piston 4001 from an axial orientation as seen in FIG. 40(*a*) to a transverse orientation as seen in FIG. 40(*b*). The piston 4001 is provided with at least a first surface 4007 and a second surface 4009 for contacting first and second positions on adjacent tissue. Actuation of the piston 4001 moves the first surface 4007 and the second surface 4009 farther apart from each other, to create a space.

Figure 41B:
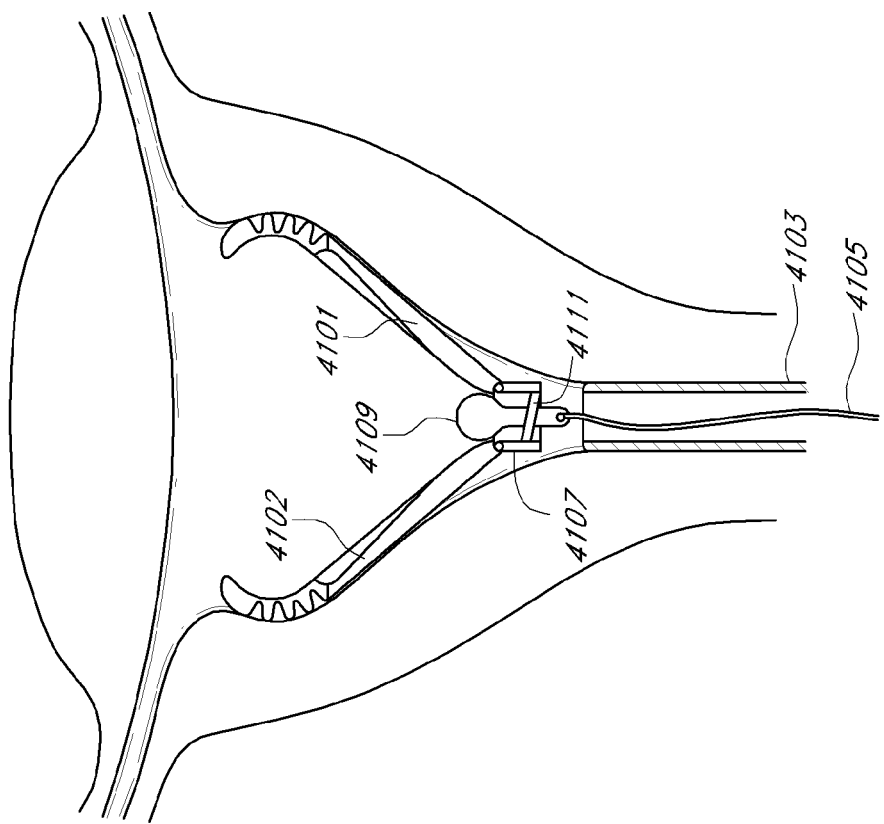
FIGS. 41(a) and 41(b) are top views, partly in section, illustrating an alternate embodiment for distending a gynecological cavity using a device with expandable arms.
Figure 41A:
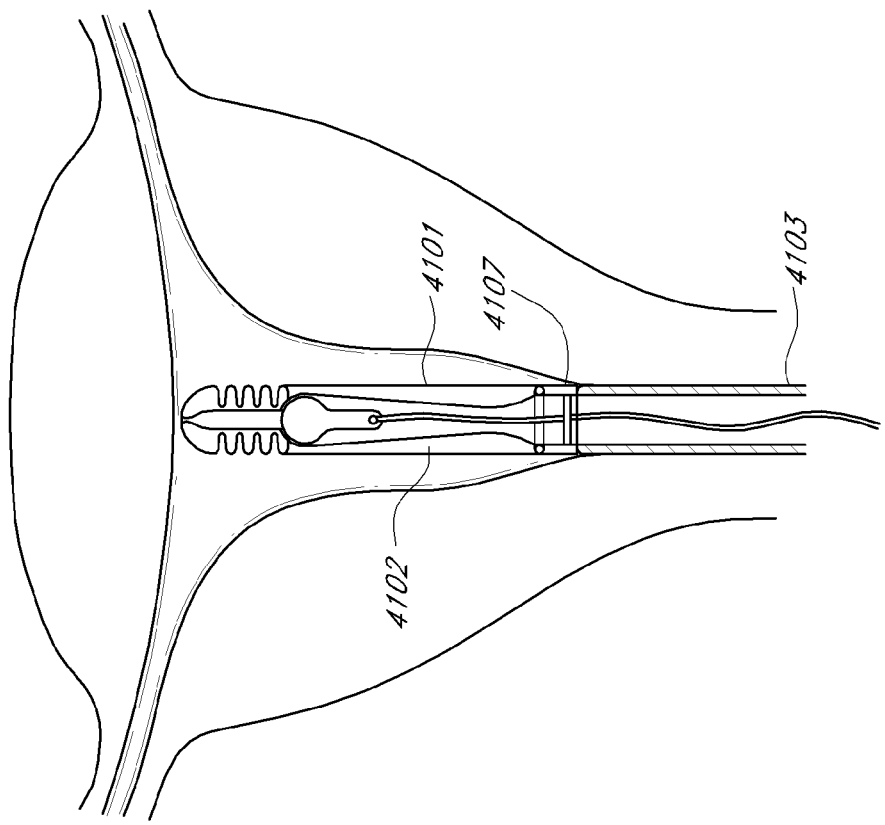

Referring to FIGS. 41(*a*) and 41(*b*), there are top views, partly in section, illustrating an alternate embodiment for distending a gynecological cavity using a device with expandable arms 4101 and 4102. In the illustrated embodiment, the expandable arms 4101 and 4102 are pivotably connected to an inner delivery tube 4107 that is axially moveably carried within an outer delivery tube 4103. In certain embodiments, the expandable arms comprise flexible atraumatic tips so as to further distend the cavity wall without causing injury or puncture to the wall. After the expandable arms 4101 are positioned in the cavity, the expandable arms 4101 and 4102 are expanded to distend the gynecological cavity when wedge portion 4109 is proximally retracted until the wedge portion 4109 is locked in position by drive brake 4111. To remove the expandable arms 4101 and 4102, the tether 4105 is released and the brake 4111 is released thereby freeing the wedge portion 4109. The expandable arms 4101 and 4102 are allowed to compress as the inner delivery tube 4107 pulls the expandable arms 4101 back into the outer tube 4103.

Various embodiments disclosed herein illustrate a first and a second arm or tine, such as the embodiment illustrated in FIGS. 41(*a*) and 41(*b*). In each of these embodiments, a third arm or tine is preferably also included, so that a first and second arm are able to open in a first plane, and the third arm is able to advance laterally with respect to the first plane, to create a three dimensional working space. A forth or a fifth or additional arms may also be included, depending upon the specific device design. The arms are movable throughout a range sufficient to create a working space having a cross sectional dimension of at least about 2 mm, and preferably at least about 3 mm or 4 mm or more. In general, the working space will have a transverse dimension of less than about 15 mm, and usually less than about 8 mm or 10 mm.

Figure 42B:
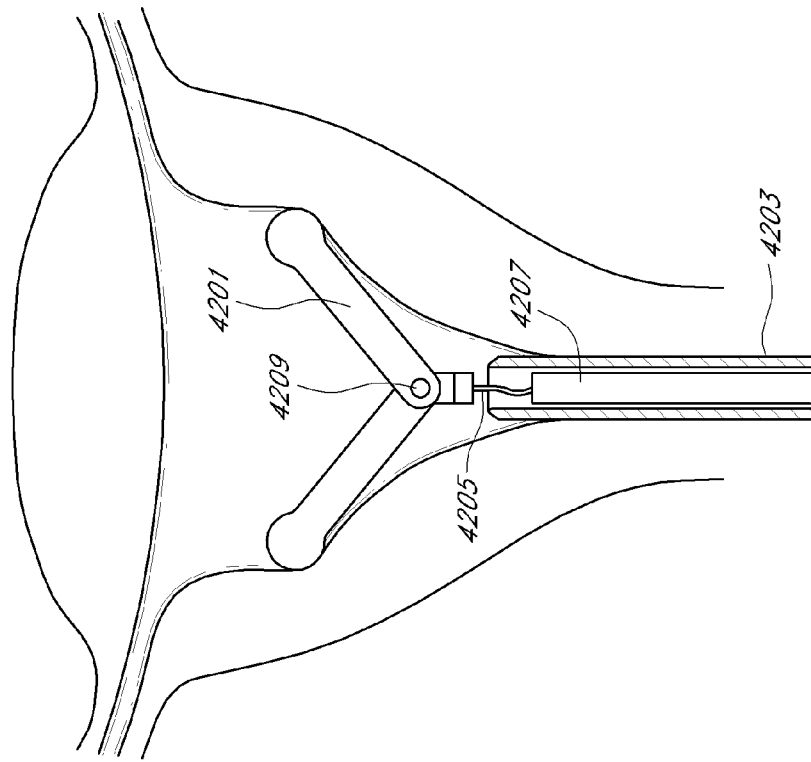
FIGS. 42(a) and 42(b) are top views, partly in section, illustrating an alternate embodiment for distending a gynecological cavity using expandable hinged bars.
Figure 42A:
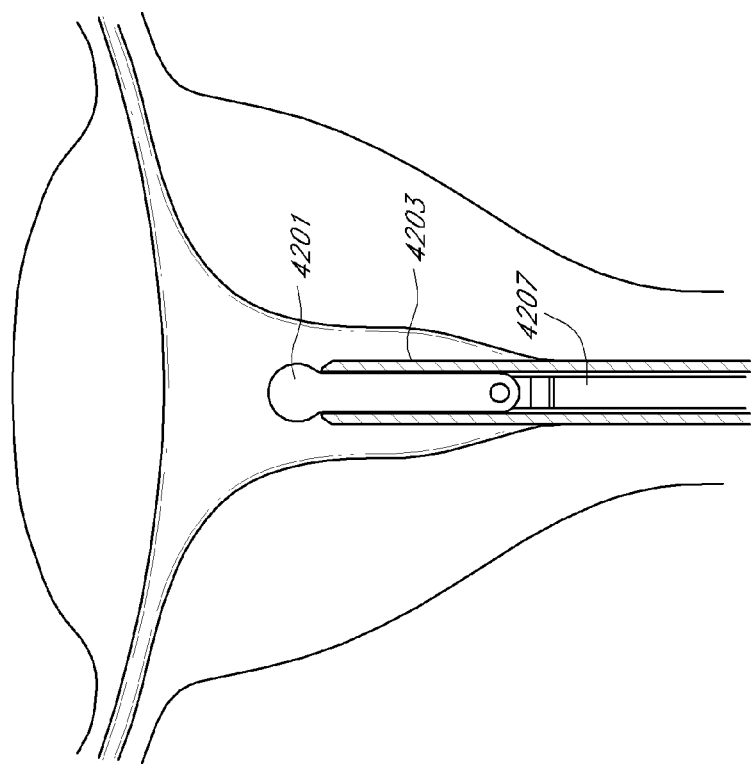

Referring to FIGS. 42(*a*) and 42(*b*), there are top views, partly in section, illustrating an alternate embodiment for distending a gynecological cavity using expandable hinged bars 4201. In the illustrated embodiment, the expandable hinged bars 4201 are deployed when an inner tube 4207 pushes the expandable hinged bars 4201 from an outer tube 4203 thereby allowing the spring loaded hinged bars 4201 to expand and distend the gynecological cavity. To remove the expandable hinged bars 4201, a tether 4205 is used to draw the expandable hinged bars 4201 into the outer tube 4203 thereby collapsing the hinged bars 4201.

In the embodiment illustrated in FIGS. 42(*a*) and 42(*b*), along with a number of other embodiments disclosed herein, the mechanical distension structure may be left in place in the expanded configuration such as illustrated in FIG. 42(*b*), and the inner tube 4207 and/or outer tube 4203 may be proximally retracted from the patient, leaving the tether 4205 in place. This provides working space for diagnostic or therapeutic instrumentation to be introduced to the treatment site. Once the procedure has been completed, a removal tube may be advanced over the tether 4205 until the distal end of the removal tube is in the vicinity of the expansion structure. The expansion structure may thereafter be retracted proximally into the removal tube such as by pulling on the tether 4205 or other removal tool which has been connected to the expansion device.

Figure 43B:
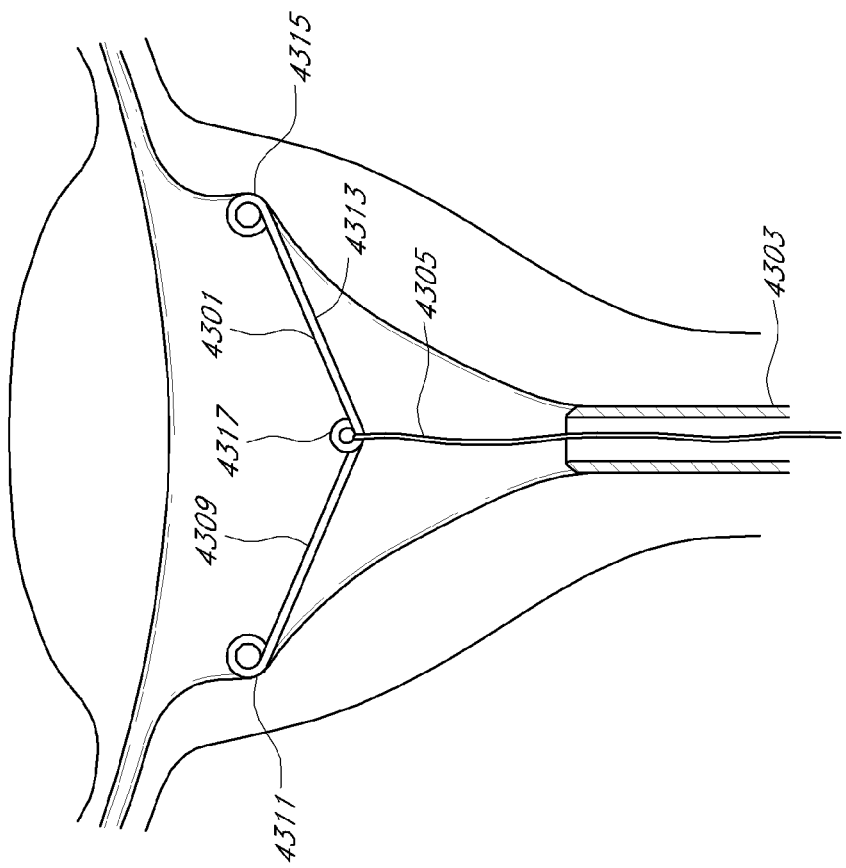
FIGS. 43(a) and 43(b) are top views, partly in section, illustrating an alternate embodiment for distending a gynecological cavity using an expandable clip.
Figure 43A:
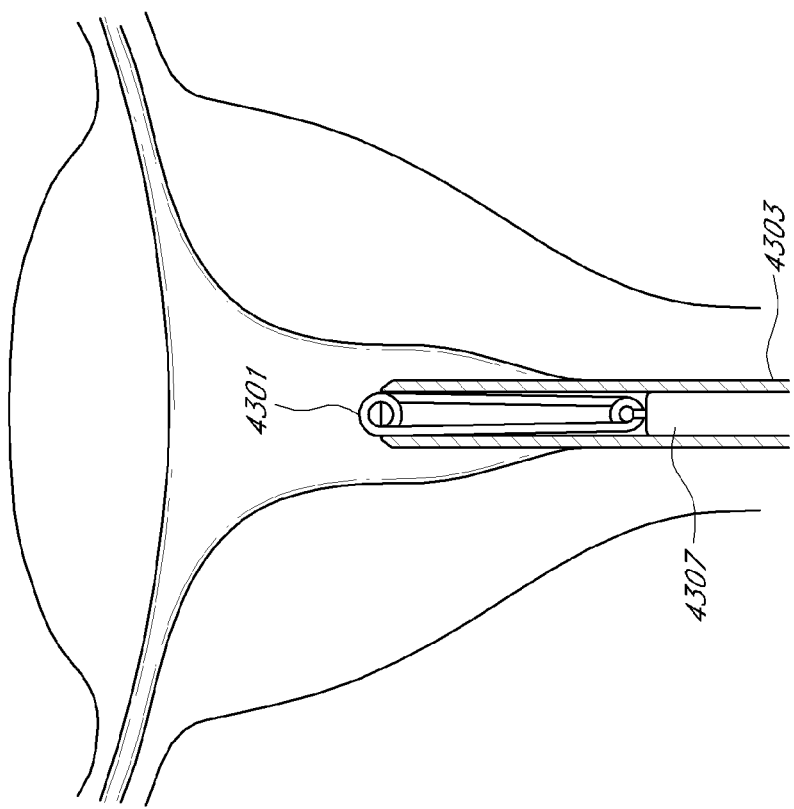

Referring to FIGS. 43(*a*) and 43(*b*), there are top views, partly in section, illustrating an alternate embodiment for distending a gynecological cavity using an expandable clip 4301. In the illustrated embodiment, the expandable clip 4301 performs similarly to the expandable hinged bars illustrated in FIGS. 42(*a*) and 42(*b*) in that the expandable clip 4301 is deployed when an inner tube 4307 pushes expandable clip 4301 from an outer tube 4303 thereby allowing the spring loaded expandable clip 4301 to expand and distend the gynecological cavity. To remove the expandable clip 4301, a tether 4305 is used to draw the expandable clip 4301 into the outer tube 4303 thereby collapsing the expandable clip 4301.

In the illustrated embodiment, the expandable clip 4301 comprises at least a first strut 4309 carrying at least one tissue contacting surface 4311. At least a second strut 4313 carries at least a second tissue contacting surface 4315. Spring bias from the clip 4301 urges the first tissue contacting surface 4311 away from the second tissue contacting surface 4315. One or two or more loops 4317 may be provided, to increase the spring force of the clip as will be understood by those of skill in the art.

Figure 44B:
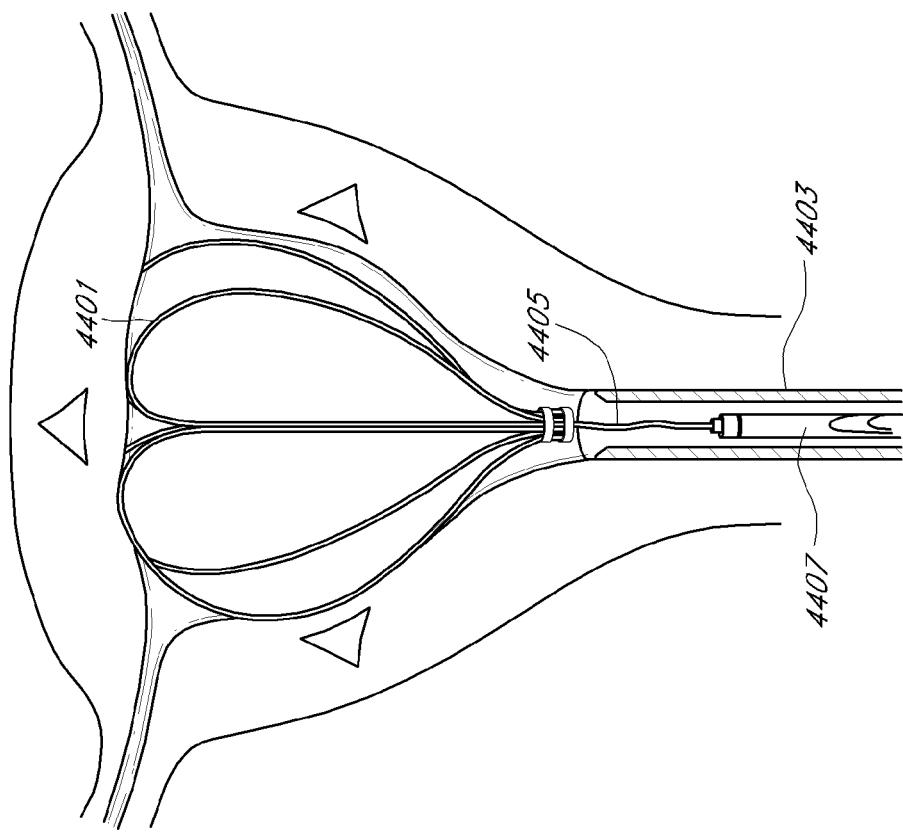
FIGS. 44(a) and 44(b) are top views, partly in section, illustrating an alternate embodiment for distending a gynecological cavity using expandable wires, and in certain embodiments the wires are formed into a wisp or cage configuration.
Figure 44A:
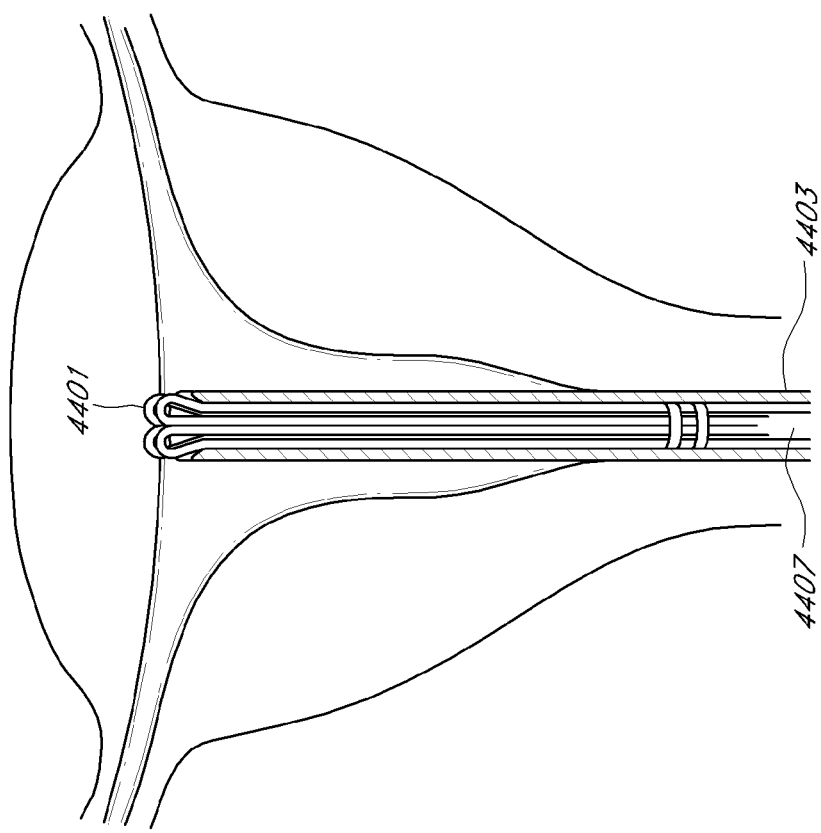

Referring to FIGS. 44(*a*) and 44(*b*), there are top views, partly in section, illustrating an alternate embodiment for distending a gynecological cavity using a plurality of wires 4401, carried by the distal end of a support structure such as an inner tube 4407. The wires have a first collapsed state and second expanded state wherein the wires form a wisp or other laterally enlarged configuration. In the illustrated embodiment, the wires 4401 are deployed when an outer tube 4403 is proximally retracted thereby exposing the wires 4401 and allowing the wires 4401 to self-expand and distend the gynecological cavity. To remove the wires 4401, a tether 4405 is used to draw the wires 4401 into the outer tube 4403 thereby collapsing the wires 4401. In some embodiments, the wires 4401 comprises nitinol or other similar materials.

The wires 4401 may be in the form of two or three or four or six or more loops such as illustrated in FIG. 44(*b*). This allows the wire loops, when in the expanded configuration, to form a three dimensional cage structure to enable sites specific distension at a desired treatment site.

Figure 45B:
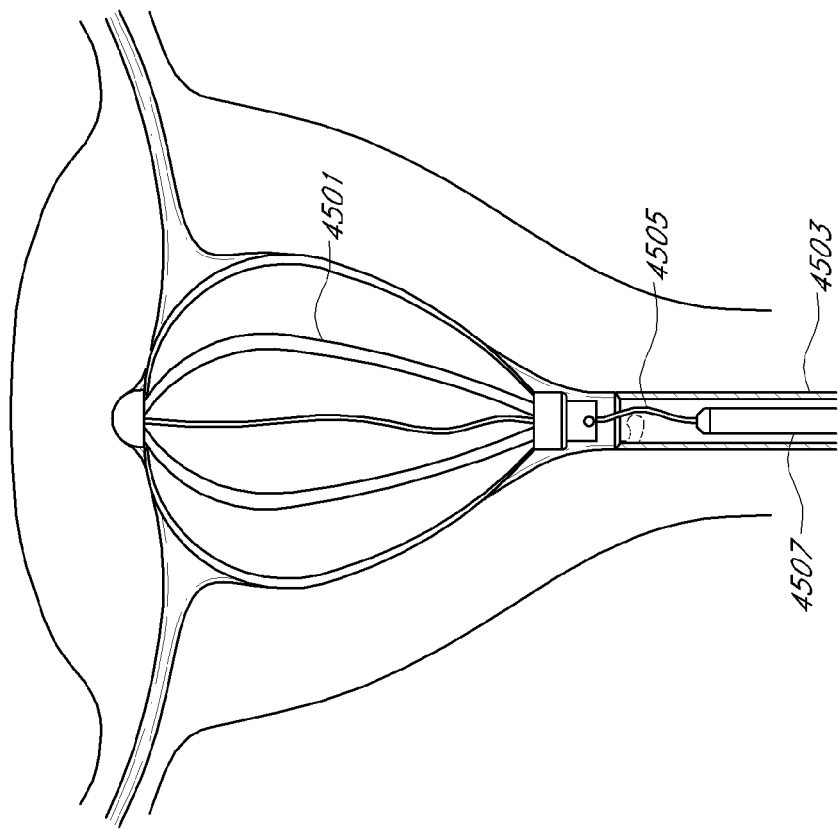
FIGS. 45(a) and 45(b) are top views, partly in section, illustrating an alternate embodiment for distending a gynecological cavity using expandable bands.
Figure 45A:
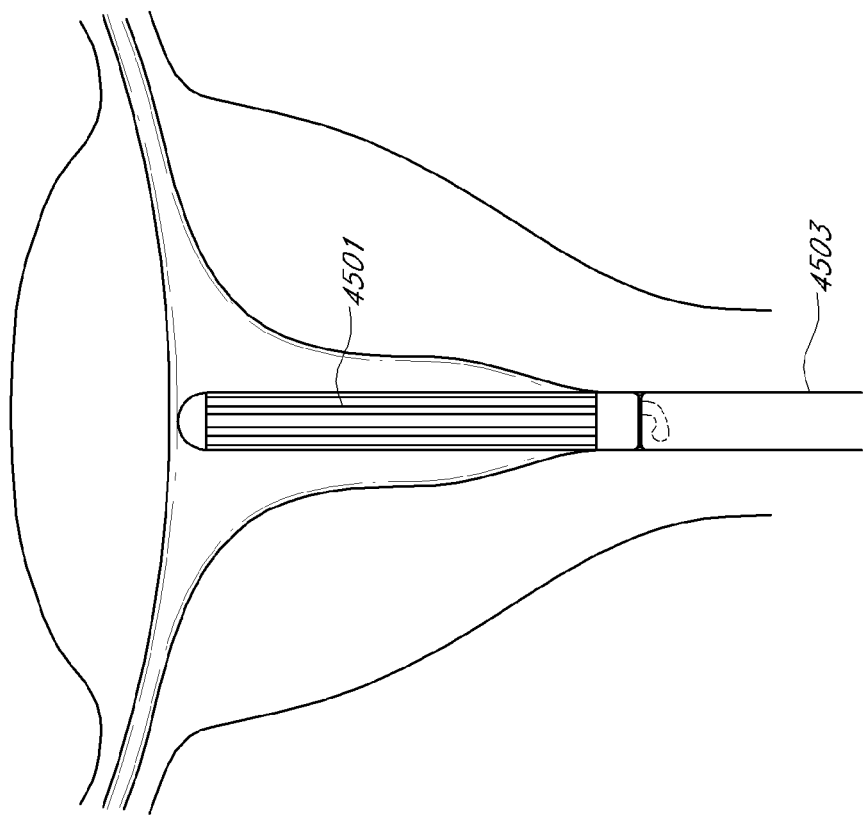

Referring to FIGS. 45(*a*) and 45(*b*), there are top views, partly in section, illustrating an alternate embodiment for distending a gynecological cavity using expandable bands 4501. In the illustrated embodiment, the expandable bands 4501 perform similarly to the wires 4401 illustrated in FIGS. 44(*a*) and 44(*b*) in that the expandable bands 4501 are deployed when an outer tube 4503 is proximally retracted relative to an inner tube 4507 thereby allowing the bands 4501 to self-expand to an unstressed state thereby distending the gynecological cavity. To remove the bands 4501, a tether 4505 or other pull element is used to draw the bands 4501 into the outer tube 4503 thereby collapsing the wires 4501.

Figure 46B:
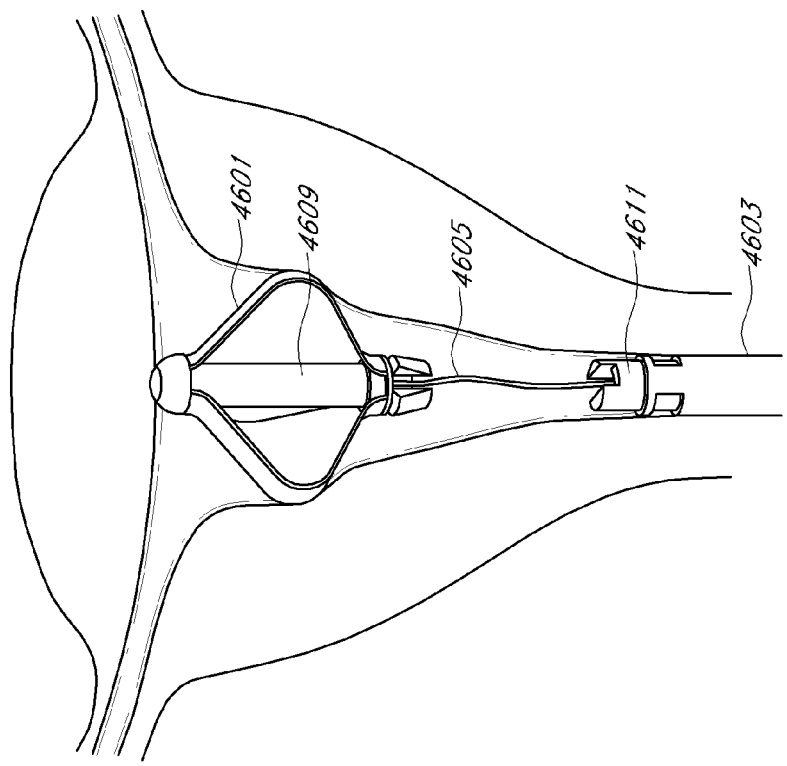
FIGS. 46(a) and 46(b) are top views, partly in section, illustrating an alternate embodiment for distending a gynecological cavity using expandable bands having a central drive shaft.
Figure 46A:
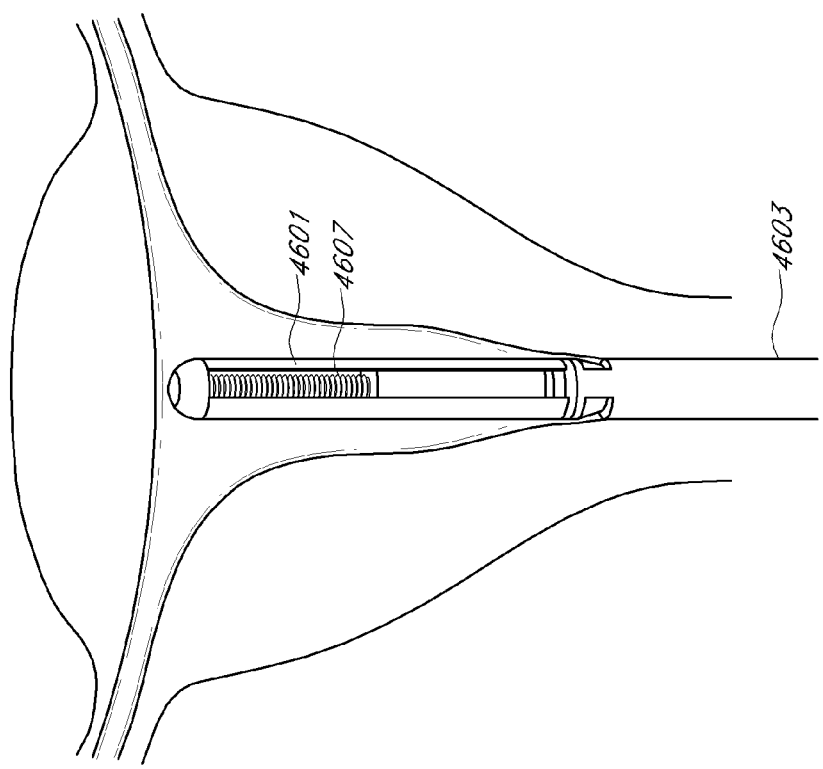

Referring to FIGS. 46(a) and 46(b), there are top views, partly in section, illustrating an alternate embodiment for distending a gynecological cavity using bands 4601 having a central drive shaft 4609. In the illustrated embodiment, the bands 4601 are deployed using outer delivery tube 4603. After the bands 4601 are positioned at the target site, a threaded rod 4607 within the drive shaft 4609 is rotated by an inner tube 4611, thereby axially shortening the distension element and causing the bands 4601 to expand laterally and distend the gynecological cavity. To remove the bands 4601, the inner tube 4611 rotates the drive shaft 4609 in the opposite direction to axially lengthen the distension element and laterally collapse the bands 4601. A tether 4605 may then be used to draw the bands 4601 into the outer delivery tube 4603.

Figure 47B:
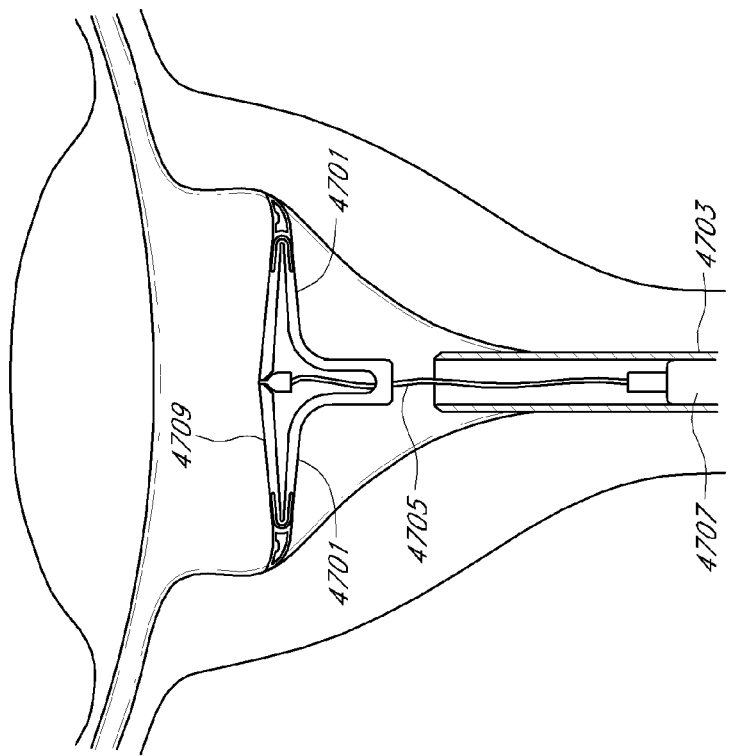
FIGS. 47(a) and 47(b) are top views, partly in section, illustrating an alternate embodiment for distending a gynecological cavity using expandable arms.
Figure 47A:
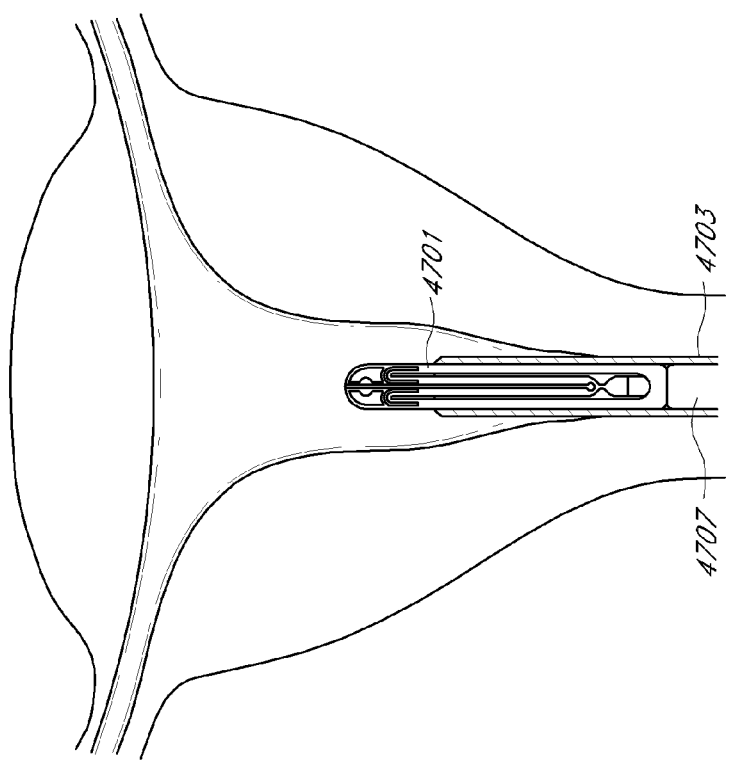

Referring to FIGS. 47(a) and 47(b), there are top views, partly in section, illustrating an alternate embodiment for distending a gynecological cavity using an expandable over center arm 4709. In the illustrated embodiment, the arms 4701 are deployed when an inner tube 4707 pushes the arms 4701 from an outer tube 4703 thereby allowing the self-expanding arms 4701 to expand and distend the gynecological cavity. To remove the expandable arms 4701, a tether 4705 is connected to at least one over center arm 4709 configured to collapse the arms 4701 when the tether 4705 is drawn proximally into the outer tube 4703. After the arms 4701 are collapsed, the tether 4705 is used to pull the arms 4701 into the outer tube 4703 for removal.

Figure 48B:
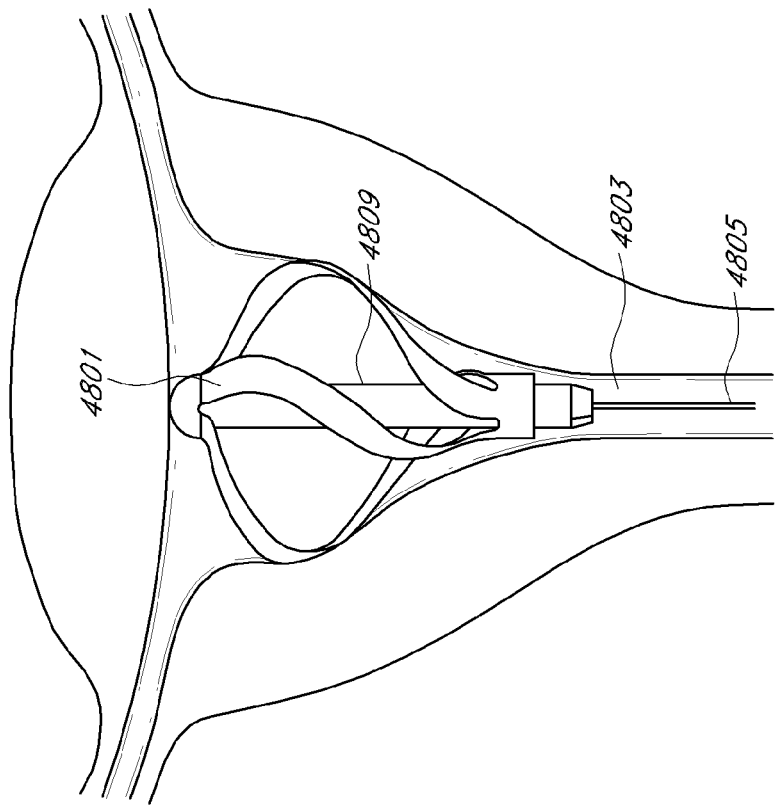
FIGS. 48(a) and 48(b) are top views, partly in section, illustrating an alternate embodiment for distending a gynecological cavity using a helical deformable anchor.
Figure 48A:
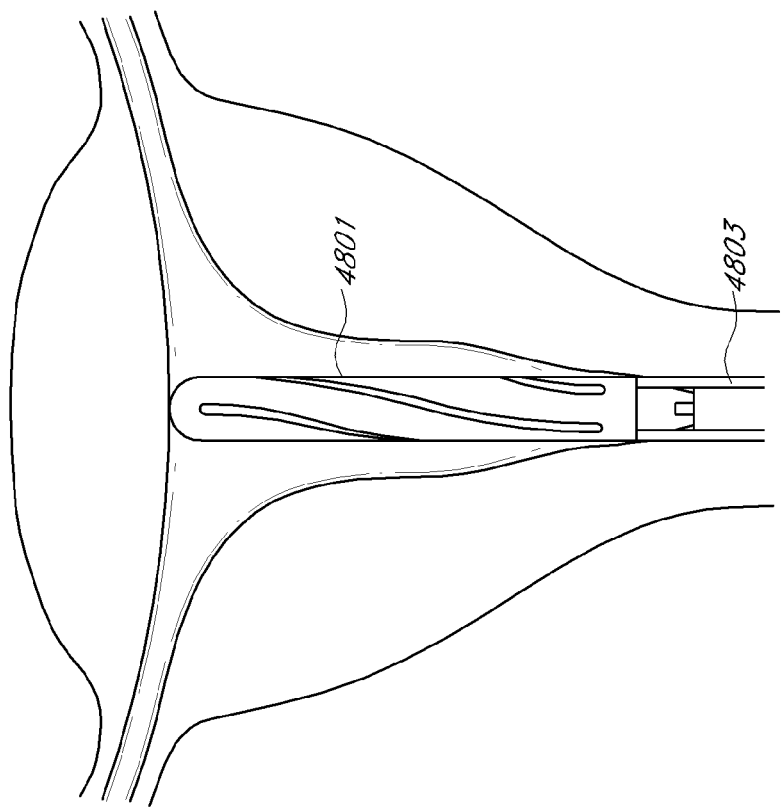

Referring to FIGS. 48(a) and 48(b), there are top views, partly in section, illustrating an alternate embodiment for distending a gynecological cavity using helical ribbon 4801. In the illustrated embodiment, the helical ribbon 4801 is exposed by proximally retracting outer delivery tube 4803. After the helical ribbon 4801 is positioned at the target site, a threaded rod within the drive shaft 4809 is rotated to cause the helical ribbon 4801 to twist and expand, thereby distending the gynecological cavity. To remove the ribbon 4801, the drive shaft 4809 is rotated in the opposite direction to collapse the helical ribbon 4801, and a tether 4805 is used to draw the collapsed helical ribbon 4801 into the outer delivery tube 4803 for removal. Two or three or four or more helical ribbons may be provided on the distension device.

Figure 49B:
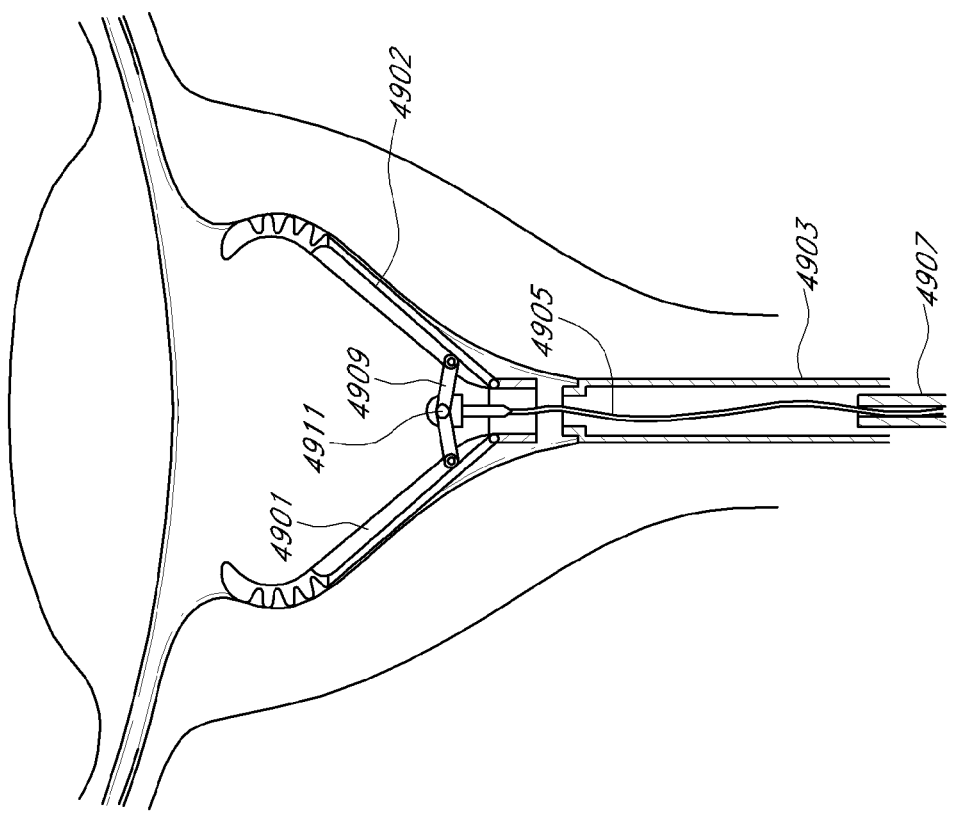
FIGS. 49(a) and 49(b) are top views, partly in section, illustrating an alternate embodiment for distending a gynecological cavity using expandable arms having an over center linkage.
Figure 49A:
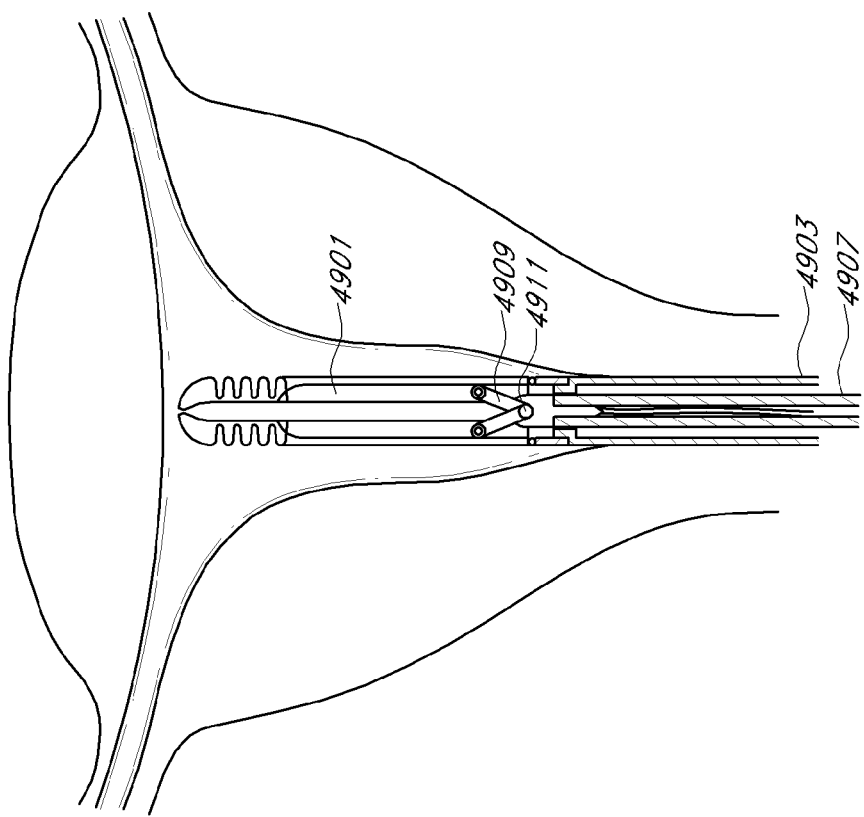

Referring to FIGS. 49(a) and 49(b), there are top views, partly in section, illustrating an alternate embodiment for distending a gynecological cavity using expandable arms 4901 and 4902 having an over center linkage 4909. In the illustrated embodiment, the expandable arms 4901 and 4902 are deployed using outer delivery tube 4803. After the expandable arms are positioned at the target site, an over center linkage 4909 is configured to laterally pivot the expandable arms 4901 and 4902 to distend the gynecological cavity. This may be accomplished by spring bias, or by axial proximal retraction or distal advance of a central pivot point 4911 on linkage 4909 using a pull wire or push wire as will be understood by those of skill in the art. To remove the expandable arms 4901, a tether 4905 or push wire may be connected to the over center linkage 4909. When the tether 4905 is drawn into outer delivery tube 4803 the over center linkage 4909 causes the expandable arms 4901 to collapse.

Figure 50C:
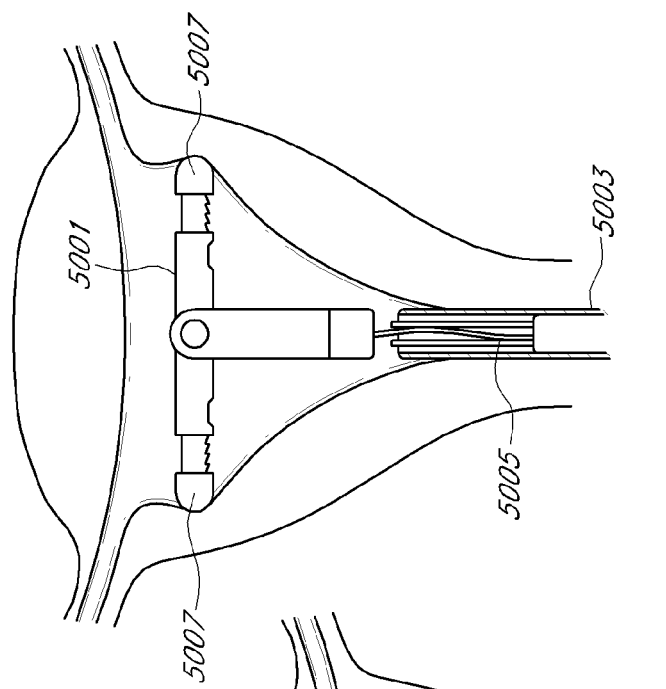
FIGS. 50(a), 50(b), and 50(c) are top views, partly in section, illustrating an alternate embodiment for distending a gynecological cavity using an expandable T-bar.
Figure 50B:
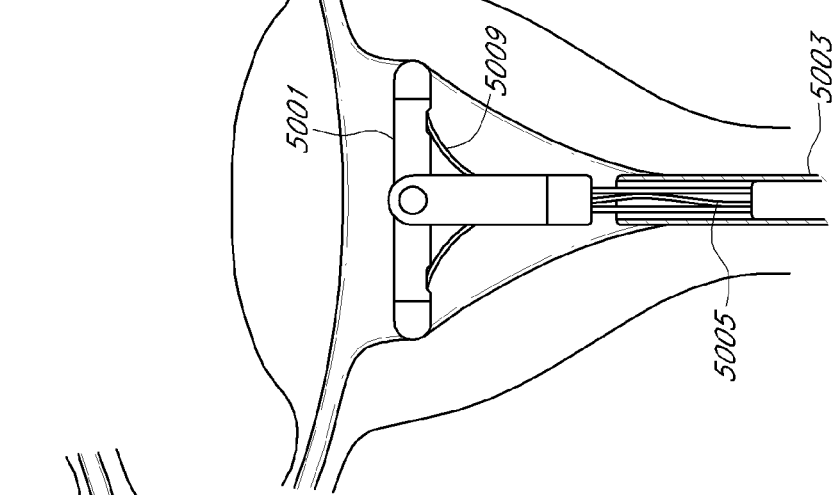
Figure 50A:
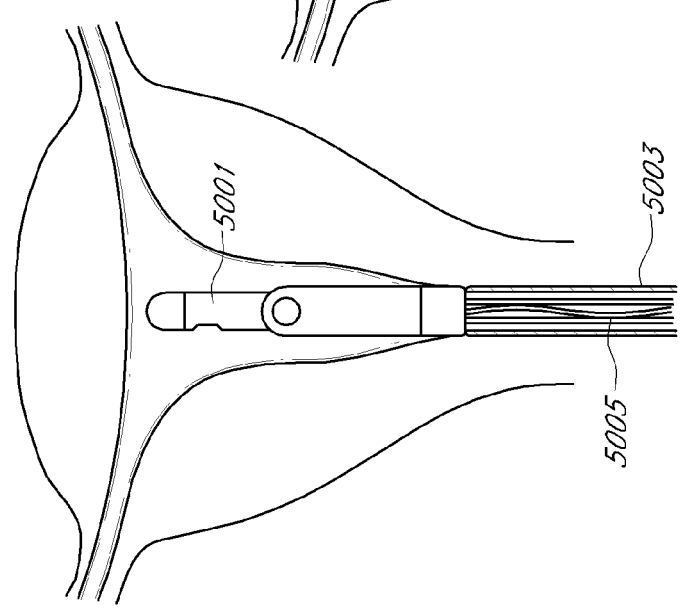

Referring to FIGS. 50(a), 50(b), and 50(c), there are top views, partly in section, illustrating an alternate embodiment for distending a gynecological cavity using expandable T-bar 5001. In the illustrated embodiment, the expandable T-bar 5001 is deployed using outer delivery tube 5003. After the expandable T-bar 5001 is positioned at the target site, the T-bar 5001 is rotated 90° degrees to engage the walls of the gynecological cavity. Wires 5009 are connected to ends 5007. When wires 5009 are actuated, the ends 5009 are ratcheted outward to distend the gynecological cavity wall. To remove the T-bar 5001, an inner delivery tube comprises an actuator to release the ratcheted ends 5007 and rotate the T-bar 5001 back 90° degrees so as to withdraw the T-bar 5001 from the gynecological cavity.

Referring to FIGS. 51(a) and 51(b), there are top views, partly in section, illustrating an alternate embodiment for distending a gynecological cavity using a segmented spine linkage 5101. In the illustrated embodiment, the spine linkage 5101 is deployed from the distal end of outer delivery tube 5103. After the spine linkage 5101 is positioned at the target site, an actuation cable 5103 is actuated such as by releasing tension so as to cause the spine linkage 5101 to form into a substantially rigid spiral or hoop shape configured to distend the gynecological cavity walls. To remove the spine linkage 5101, the actuation cable 5103 is actuated such as by proximal retraction to cause the spine linkage 5101 to be flexible and not rigid. The flexible spine linkage 5101 is then proximally withdrawn into outer delivery tube 5103. In other embodiments, the spine linkage 5101 is actuated by proximal retraction on the actuation cable 5103 to form a substantially rigid spiral or hoop, and the actuation cable 5103 is released to allow the spine linkage 5101 to be flexible.

Figure 52B:
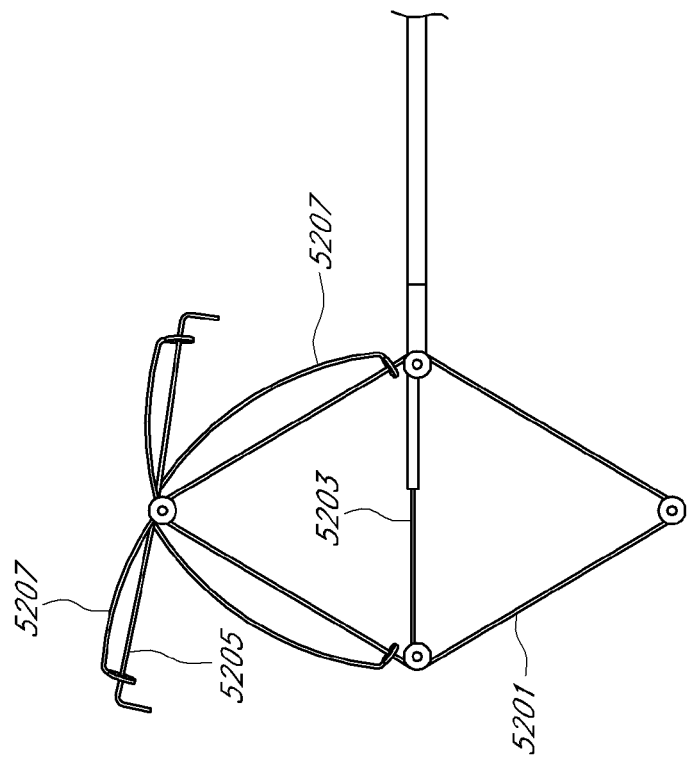
FIGS. 52(a) and 52(b) are top views, partly in section, illustrating an alternate embodiment for distending a gynecological cavity using linked bars having springs and an actuation rod.
Figure 52A:
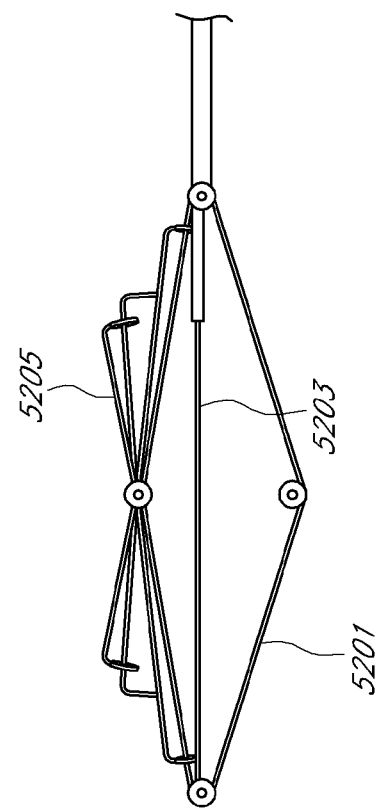

Referring to FIGS. 52(a) and 52(b), there are top views, partly in section, illustrating an alternate embodiment for distending a gynecological cavity using linked bars 5201 having springs 5207 and an actuation rod 5203. In the illustrated embodiment, the linked bars 5201 are deployed using a delivery tube. After the linked bars are positioned at the target site, an actuation rod 5203 pulled into the delivery tube to cause the linked bars to enter into a laterally expanded state capable of distending the gynecological cavity wall. To collapse and remove the linked bars 5201, the actuation rod 5203 is released or pushed out of the delivery tube. Springs 5207 bias the linked bars 5201 toward the collapsed state. In certain embodiments, the linked bars 5201 also comprise expansion arms 5205 that expand to further distend the gynecological cavity wall. Springs 5207 bias the expansion arms 5205 toward the expanded state.

Referring to FIGS. 53(a) and 53(b), there are top views, partly in section, illustrating an alternate embodiment for distending a gynecological cavity using nitinol wire 5301 having one or two or more pivots 5303. In the illustrated embodiment, the nitinol wire 5301 is deployed through a delivery tube. After the nitinol wire 5301 is positioned at the target site, an actuation rod 5305 is released and may be pulled into the delivery tube to cause the nitinol wire 5301 to enter into an expanded state configured to distend the gynecological cavity wall. To collapse and remove the nitinol wire 5301, the actuation rod 5305 is released and/or pushed through the delivery tube to cause the nitinol wire 5301 to enter into a collapsed state. The collapsed nitinol wire 5301 is then drawn into the delivery tube to be removed.

Referring to FIGS. 54(a), 54(b), 54(c), and 54(d), there are top views, partly in section, illustrating an alternate embodiment for distending a gynecological cavity using a bellows device 5401, which comprises bellows 5409 and an elastomeric restraint 5411 that provides tension as the bellows expands axially. In the illustrated embodiment, the bellows device 5401 is deployed through a delivery tube 5403 and is pushed out of the delivery tube 5403 and into the gynecological cavity by inner push tube 5407. After the bellows device 5401 is positioned at the target site, a fluid, gel, gas, or the like is introduced into the bellows 5409 by way of a supply tube 5405, thereby causing the bellows to expand along an axis transverse to the longitudinal axis of the delivery tube and distend the gynecological cavity wall. During the expansion of the bellows, the restraint 5411 provides tension on the bellows 5409 so as to prevent the bellows 5409 from shifting or falling over during expansion.

To collapse and remove the bellows device 5401, a negative pressure is applied to the supply tube 5405 to remove the fluid, gel, gas, or the like from the bellows 5409, thereby allowing the bellows 5409 to collapse due to the tension provided by restraint 5411. In the collapsed state, the bellows device 5401 is drawn into the delivery tube 5403 by pulling the supply tube 5405. In certain embodiments, multiple bellows devices 5401 can be used simultaneously to distend the gynecological cavity.

Referring to FIGS. 55(*a*), 55(*b*), 55(*c*), 55(*d*), and 55(*e*) are top views, partly in section, illustrating an alternate embodiment for distending a gynecological cavity using an umbrella device. In the illustrated embodiment, the collapsed umbrella device 5501 comprises at least two or three or four or more arms 5515 which may be biased to be in a collapsed state. The umbrella device 5501 is deployed through a delivery tube 5503 and is pushed out of the delivery tube 5503 using a central support 5505. Tension cables 5507 are connected to the proximal ends 5512 of the umbrella device 5501 and are wrapped around pulley hubs 5509 and are positioned along central support 5505 into the delivery tube 5503 wherein a user can pull or release the tension cables 5507.

After the distal end 5513 of the collapsed umbrella device 5501 is positioned in the fundus of the uterus, tension cables 5507 are pulled proximally into the delivery tube 5503 thereby causing the arms 5515 of the umbrella device 5501 to expand and distend the gynecological cavity wall. In the expanded state, the tension cables 5507 are locked into position to maintain distension of the gynecological cavity wall. In certain embodiments, the tension cables 5507 are locked into position by a locking means near the proximal end of umbrella device 5501. In other embodiments, the tension cables 5507 are locked into position by a locking means positioned outside the patient's body. It will be understood by those skilled in the art that various locking means could be employed to secure the position of the tension cables.

To collapse and remove the umbrella device 5501, the user releases the tension cables 5507, thereby allowing the arms 5515 to enter into the collapsed state for removal through the delivery tube 5503. In certain embodiments, the umbrella device 5501 comprises at least two arms 5515, and in other embodiments the umbrella device 5501 comprises at least four arms 5515 for distending the gynecological cavity wall.

Alternatively, the umbrella 5501 may be radially expanded under a distal compression force rather than a proximal tension. This may be accomplished by providing an axially moveable push wire within or concentrically around the central support 5505. A distal end of the push wire is mechanically linked such as by a strut to each of the proximal ends 5512 of the arms 5515. Distal axial advance of the push wire will cause the struts and thus arms 5515 to advance radially outwardly to create a working space.

Figure 56C:
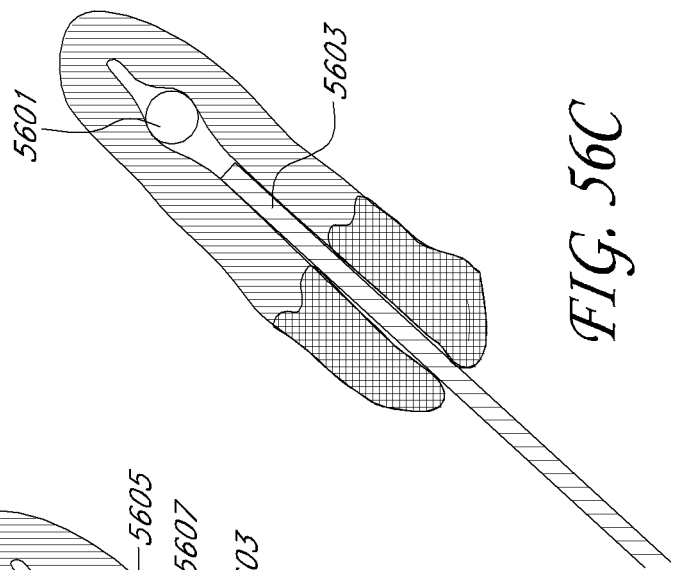
FIGS. 56(a), 56(b), and 56(c) are top views, partly in section, illustrating an alternate embodiment for distending a gynecological cavity using an inflatable balloon.
Figure 56B:
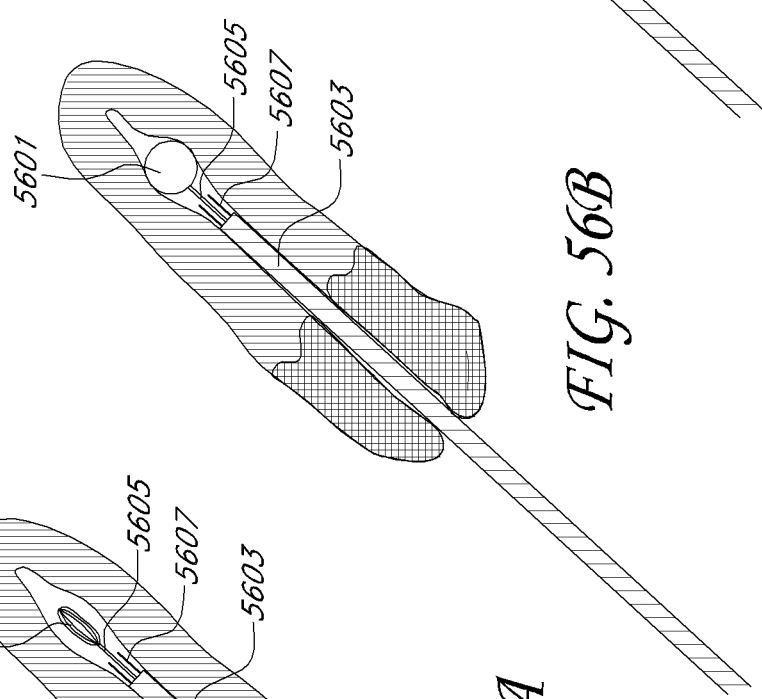
Figure 56A:
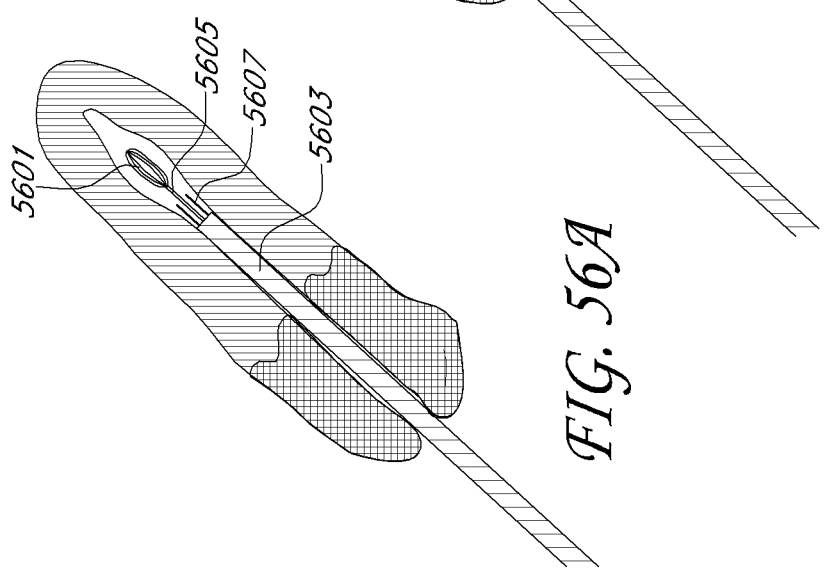

Referring to FIGS. 56(*a*), 56(*b*), and 56(*c*) are top views, partly in section, illustrating an alternate embodiment for distending a gynecological cavity using a non-elastic balloon 5601. In the illustrated embodiment, the collapsed balloon 5601 is deployed through a delivery tube 5603 and is pushed out of the delivery tube 5603 by push tube 5607. After the collapsed balloon 5601 is positioned at the target site, a fluid, gel, gas, or the like is introduced into the balloon 5601 by way of a supply tube 5605, thereby causing the balloon to expand to the given shape of the balloon. The expansion of the balloon, which comprises semi-rigid walls, provides sufficient force to distend the gynecological cavity wall.

To collapse and remove the balloon 5601, a negative pressure is applied to supply tube 5605 to remove the fluid, gel, gas, or the like from the balloon 5601, thereby allowing the balloon 5601 to collapse. In the collapsed state, the balloon 5601 is removed from the gynecological cavity by pulling the supply tube 5605 into the delivery tube 5603. In certain embodiments, the balloon comprises polyetheretherketones (PEEK), polyethylene terephthalates (PET), or other like composite materials that have minimal stretch characteristics.

In general, the mechanical distension device is thus any of a wide variety of structures which are capable of transluminal introduction through the working channel in a first, reduced cross sectional profile and transformation to a second, enlarged cross sectional profile once in the vicinity of the treatment site. The second, enlarged cross sectional profile creates a sufficient space at the site to allow manipulation of diagnostic or therapeutic tools necessary for the intended procedure. This may be, for example, equivalent to at least the volume of the cavity created by 70 to 80 mm Hg of fluid distension.

Typically, the distension provided by a fluid or gas is diffuse in nature. Rather than creating a discrete working space at the desired treatment site, the media expands the associated cavity without preference. In the case of uterine distension, a fluid pressure of 35 to 60 mm Hg typically produces a cavity of 10 to 50 cc in total volume. But the volume of the distension media is distributed evenly throughout the entire uterus, so that the effective working space provided in the immediate vicinity of any particular treatment site is relatively small compared to the total volume of the cavity. The addition of additional pressure that can reach 100 to 120 mm Hg does provide additional cavity volume but at the risk of fluid intravasation and greater pain for the patient.

One particular advantage of the mechanical distension structures in accordance with the present invention is the ability to create a specific working space at a desired site, while leaving other parts of the cavity in its collapsed configuration. By localizing the distension to the desired site, the size of the working cavity at that site can be optimized while minimizing the total volume of the distension and the associated pain for the patient.

For example, it may be desirable to provide a working space in the immediate vicinity of a treatment site having dimensions that would approximate a 10 cc sphere. To create that same working space by infusion of distension media, the infused volume may need to be at least about 40 cc or 50 cc or more. Thus, in accordance with the present invention, the working space created at the desired site is at least about 50%, often at least about 70% and preferably at least about 85% of the enclosed volume of the expandable portion of the distension device. The working space may be approximately equal to the volume of the expanded device, which may be less than about 50%, often less than about 35% and preferably less than about 25% of the volume of distension media which would be necessary to achieve a similar working volume at the treatment site.

The expansion device may be permanently attached to the distal end of an operating shaft, permanently attached to the distal end of a tether, or detachable at the treatment site. Any of a wide variety of detachable expansion structures may be subsequently removed by advancing a grasper down the working channel and grasping the device under endoscopic visualization. The device may be thereafter be proximally retracted into the working channel and reduced in cross section for removal.

In general, the tissue distension structure will have at least a first surface for contacting a first tissue zone and a second surface for contacting a second tissue zone. Activation of the distension structure advances the first and second surfaces away from each other, to enlarge the distance between the first and second tissue zones. In some embodiments, for example, the tissue distension structure opens such that it resides substantially within a single plane which contains the longitudinal axis of the device. In alternative embodiments, the tissue distension structure may open in two transverse planes having an intersection along the longitudinal axis of the device, or such that the distension structure opens into a more complex three dimensional configuration, including spherical, elliptical, and other geometric forms of rotation about an axis. In each instance, the tissue distension device preferably includes at least one opening in a side or end wall thereof, to permit access to the target tissue.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method of performing a transcervical surgical procedure in a uterus, comprising:
    transcervically positioning an expandable support structure within the uterus using a deployment tool releasably attached to the support structure;
    expanding the support structure into a three-dimensional configuration including an upper portion and a lower portion spaced apart from the upper portion, wherein expanding the support structure delivers an expansion force against opposing walls of the uterus to thereby create a three-dimensional void within the uterus between the upper and lower portions of the expanded support structure through non-fluid mechanical distention of the uterus;
    detaching the deployment tool from the expanded support structure;
    removing the deployment tool from the uterus, leaving the expanded support structure in place;
    after removal of the deployment tool from the uterus, introducing a surgical instrument into the uterus so that a distal end of the surgical instrument is located in the void between the upper and lower portions of the expanded support structure;
    using the surgical instrument to perform a surgical procedure in the uterus by advancing the surgical instrument through an opening in the expanded support structure while the expanded support structure distends the uterus through non-fluid mechanical distention, the surgical procedure including removal of uterine wall tissue through the opening;
    removing the surgical instrument from the uterus upon completion of the surgical procedure,
    collapsing the support structure within the uterus after removal of the surgical instrument from the uterus; and
    removing the collapsed support structure from the uterus.

2. The method as in claim 1, further comprising coupling the support structure to a removal tool before collapsing and removing the support structure from the uterus.

3. The method as in claim 1, wherein the procedure is surgical removal of fibroid tissue.

4. The method as in claim 1, wherein expanding the support structure delivers an expansion force of at least about 0.5 lbs to mechanically distend the uterus.

5. The method as in claim 1, wherein expanding the support structure delivers an expansion force of at least about 1.0 lbs to mechanically distend the uterus.

6. The method as in claim 1, wherein expanding the support structure delivers an expansion force of at least about 5.0 lbs to mechanically distend the uterus.

7. The method as in claim 1, wherein expanding the support structure achieves an equivalent distension of the uterus to that achieved by introduction of a liquid distension media at a pressure of at least about 40 mm Hg.

8. The method as in claim 1, wherein expanding the support structure achieves an equivalent distension of the uterus to that achieved by introduction of a liquid distension media at a pressure of about 70 mm Hg.

9. The method as in claim 1, the uterus having a fundus, wherein the expanded support structure contacts a surface of the fundus.

10. A method of performing a procedure in a uterus of a patient, the uterus having a cervix at a proximal end and a fundus at a distal end, comprising:
    positioning a deployment tool in at least inside the cervix;
    delivering an expandable support structure through the deployment tool and into the uterus;
    expanding the support structure into a three-dimensional configuration including an upper portion and a lower portion spaced apart from the upper portion, wherein expanding the support structure delivers an expansion force against opposing walls of the uterus to thereby create a three-dimensional void within the uterus between the upper and lower portions of the expanded support structure through non-fluid mechanical distention of the uterus;
    removing the deployment tool from inside the patient, leaving the expanded support structure in place within the uterus;
    after removal of the deployment tool from the patient, introducing a surgical instrument into the uterus so that a distal end of the surgical instrument is located in the void between the upper and lower portions of the expanded support structure;
    using the surgical instrument to perform a surgical procedure in the uterus by advancing the surgical instrument through an opening in the expanded support structure while the expanded support distends the uterus through non-fluid mechanical distention, the surgical procedure including removal of uterine wall tissue through the opening;
    removing the surgical instrument from the uterus upon completion of the surgical procedure,
    collapsing the support structure within the uterus after removal of the surgical instrument from the uterus; and
    removing the collapsed support structure from the uterus.

11. The method as in claim 10, the uterus having a fundus, wherein the expanded support structure contacts a surface of the fundus.

12. The method as in claim 10, further comprising coupling the expandable support structure to a removal tool before removing the expandable support structure from the uterus.

13. The method as in claim 10, wherein the procedure is surgical removal of fibroid tissue.

14. A method of performing a transcervical procedure in a uterus of a patient, comprising:
    transcervically positioning an expandable support structure within the uterus using a deployment tool that is inserted into the patient to access the uterus, the deployment tool being releasably attached to the support structure, the support structure comprising a three-dimensional array of filaments, with adjacent filaments of the array defining windows there between;

expanding the support structure, wherein expanding the support structure delivers an expansion force against opposing walls of the uterus so that the expanded filament array defines a three-dimensional interior void within the uterus through non-fluid mechanical distention of the uterus, thereby providing access to uterine wall tissue from within the interior void of the expanded support structure through the windows of the expanded support structure;

detaching the deployment tool from the expanded support structure;

removing the deployment tool from the patient, while leaving the expanded support structure in the patient's uterus;

after removing the deployment tool from the patient, introducing a surgical instrument into the uterus so that a distal end of the surgical instrument is located in the interior void of the expandable support structure defined by the filament array; and using the surgical instrument to remove uterine wall tissue through one or more windows defined by adjacent filaments of the expanded support structure while the support structure distends the uterus through non-fluid mechanical distention.

15. The method as in claim 14, further comprising coupling the support structure to a removal tool, and removing the support structure from the uterus.

16. The method as in claim 14, wherein the uterine wall tissue comprises fibroid tissue.

17. The method as in claim 14, wherein expanding the support structure delivers an expansion force of at least about 5.0 lbs to mechanically distend the uterus.

18. The method as in claim 14, wherein expanding the support structure achieves an equivalent distension of the uterus to that achieved by introduction of a liquid distension media at a pressure of at least about 40 mm Hg.

19. The method as in claim 14, the uterus having a fundus, wherein the expanded support structure contacts a surface of the fundus.

* * * * *